United States Patent [19]

Niigata et al.

[11] Patent Number: 5,643,931
[45] Date of Patent: Jul. 1, 1997

[54] BISOXADIAZOLIDINE DERIVATIVE

[75] Inventors: Kunihiro Niigata, Saitama; Takumi Takahashi, Ibaraki; Tatsuya Maruyama, Ibaraki; Takayuki Suzuki, Ibaraki; Kyoichi Maeno, Ibaraki; Kenichi Onda, Ibaraki; Toru Kontani, Ibaraki; Osamu Noshiro, Ibaraki; Reiko Koike, Ibaraki; Akiyoshi Shimaya, Ibaraki; Jun Irie, Ibaraki, all of Japan

[73] Assignee: Yamanouchi Pharmaceutical Co., Ltd., Tokyo, Japan

[21] Appl. No.: 537,907

[22] PCT Filed: Apr. 26, 1994

[86] PCT No.: PCT/JP94/00696

§ 371 Date: Oct. 26, 1995

§ 102(e) Date: Oct. 26, 1995

[87] PCT Pub. No.: WO94/25448

PCT Pub. Date: Nov. 10, 1994

[30] Foreign Application Priority Data

Apr. 30, 1993 [JP] Japan ................................. 5-127898
Dec. 29, 1993 [JP] Japan ................................. 5-350209

[51] Int. Cl.$^6$ ........................ C07D 413/14; A61K 31/41
[52] U.S. Cl. ........................ 514/364; 546/269.1; 548/132
[58] Field of Search ........................... 548/132; 546/277; 514/364

[56] References Cited

U.S. PATENT DOCUMENTS

| | | | |
|---|---|---|---|
| 4,598,153 | 7/1986 | United States | 546/229 |
| 5,420,146 | 5/1995 | Malamas | 514/364 |

FOREIGN PATENT DOCUMENTS

| | | |
|---|---|---|
| 0597102A1 | 5/1994 | European Pat. Off. . |
| WO9303021 | 2/1993 | Japan . |
| WO9203425 | 3/1992 | WIPO . |
| WO9218475 | 10/1992 | WIPO . |

OTHER PUBLICATIONS

Journal of Medicinal Chemistry, vol. 34, No. 5, May 1991 Washington, D.C., US, pp. 1538–1544, R. L. Dow, et al.

*Primary Examiner*—Robert Gerstl
*Attorney, Agent, or Firm*—Sughrue, Mion, Zinn, Macpeak & Seas

[57] ABSTRACT

A bisoxadiazolidine dione derivative represented by the following general formula (I) or a pharmaceutically acceptable salt thereof, which is useful as an insulin sensitivity-increasing drug, and a pharmaceutical composition thereof.

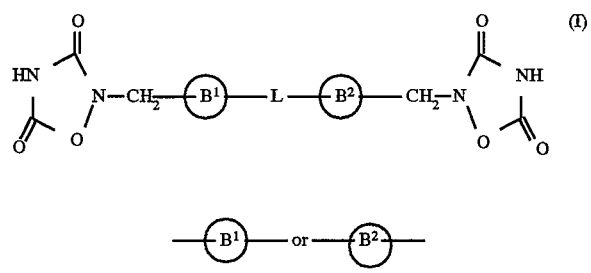

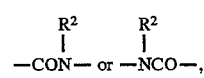

each represents a phenylene group

L:

(1) an oxygen, (2) a

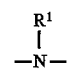

(3) a —S(O)$_n$—, (4) a —CO—, (5) a $$\underset{|}{\overset{R^2}{-}}\text{CON}- \text{ or } \underset{|}{\overset{R^2}{-}}\text{NCO}-,$$

(6) an alkylene group or an alkenylene group which may respectively be interrupted with an oxygen atom and/or a sulfur atom.

10 Claims, No Drawings

BISOXADIAZOLIDINE DERIVATIVE

This application is a 371 of PCT/JP9400696 filed Apr. 26, 1994.

TECHNICAL FIELD

This invention relates to a novel bisoxadiazolidine derivative and pharmaceutically acceptable salts thereof which are useful as medicines, particularly as a hypoglycemic drug (insulin sensitivity-increasing drug) and to a pharmaceutical composition containing the same.

BACKGROUND ART

Sulfonylurea compounds and biguanide compounds are currently used clinically as synthetic hypoglycemic drugs for the treatment of diabetes. Biguanide compounds, however, are rarely used because it induces lactic acidosis and their application is therefore restricted. On the other hand, sulfonylurea compounds show secure hypoglycemic action and hardly generate side effects, but it is necessary to take great caution in using them because they sometimes cause hypoglycemia.

In recent years, insulin sensitivity-increasing drugs capable of showing hypoglycemic action by increasing insulin sensitivity in peripheral tissues have been drawing attention as a successor for the aforementioned synthetic hypoglycemic drugs.

Compounds having the insulin sensitivity-increasing action have been synthesized as disclosed, for example, in International Patent Publication No. 92/03425 pamphlet (1992).

Under such circumstances, the inventors of the present invention have previously found that a bisoxa or thiazolidine derivative has excellent insulin sensitivity-increasing action and have filed a patent application [cf. International Patent Publication No. 93/03021 pamphlet (1993)].

DISCLOSURE OF THE INVENTION

The inventors of the present invention conducted intensive studies on substances having insulin sensitivity-increasing action and found that a bisoxadiazolidine derivative represented by the following general formula (I) has excellent insulin sensitivity-increasing action, hence resulting in the accomplishment of the present invention.

That is, according to the present invention, there is provided a bisoxadiazolidine derivative represented by a general formula (I)

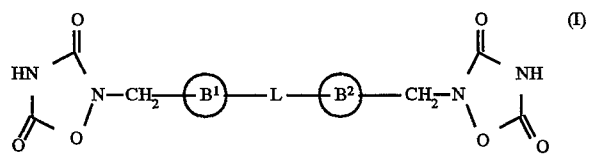

[symbols in the formula represent the following meanings;

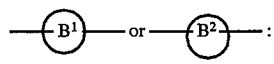

the same or different from each other and each represents a phenylene group which may be substituted,

L:

(1) an oxygen atom, (2) a group represented by the formula

(3) a group represented by the formula —S(O)$_n$—,
(4) a group represented by the formula —CO—,
(5) a group represented by the formula

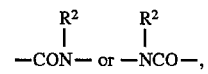

(6) an alkylene group or an alkenylene group which may respectively be interrupted with an oxygen atom and/or a sulfur atom and which may respectively be substituted, or (7) a group represented by a formula

$R^1$: a hydrogen atom or a lower alkyl group,
n: 0, 1 or 2,
$R^2$: a hydrogen atom or a lower alkyl group,
$L^1$ and $L^2$: the same or different from each other and each represents (1) an oxygen atom,
(2) a group represented by the formula

($R^1$ is as defined in the foregoing), (3) a group represented by the formula —S(O)$_n$— (n is as defined in the foregoing),
(4) a group represented by the formula —CO—,
(5) a group represented by the formula

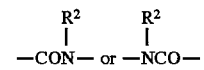

($R^2$ is as defined in the foregoing), or (6) an alkylene group, an alkenylene group or a pyridinediyl group which may respectively be interrupted with an oxygen atom and/or a sulfur atom and which may respectively be substituted, and

a cycloalkanediyl group, an arylene group or a pyridinediyl group, which may respectively be substituted], or a pharmaceutically acceptable salt thereof.

The compound of the present invention is a novel compound whose structure is entirely different from any prior art compounds having insulin sensitivity-increasing action, because it has a unique chemical structure as a bis form in which (1,3,4-oxadiazolidine-3,5-dione-2-yl)methyl groups are linked to both ends of a connecting group

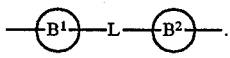

The following describes the compound of the present invention in detail.

Unless otherwise noted, the term "lower" as used herein in the definition of the general formulae means a straight or branched carbon chain having 1 to 6 carbon atoms.

In consequence, illustrative examples of the "lower alkyl group" include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and the like.

The term "an alkylene group or an alkenylene group which may respectively be interrupted with an oxygen atom and/or a sulfur atom and which may respectively be substituted" means all of unsubstituted alkylene groups, unsubstituted alkenylene groups, substituted alkylene groups, substituted alkenylene groups, unsubstituted alkylene groups interrupted with an oxygen atom and/or a sulfur atom, unsubstituted alkenylene groups interrupted with an oxygen atom and/or a sulfur atom, substituted alkylene groups interrupted with an oxygen atom and/or a sulfur atom and substituted alkenylene groups interrupted with an oxygen atom and/or a sulfur atom, and the term "interrupted with an oxygen atom and/or a sulfur atom" means not only the groups in which an oxygen atom and/or sulfur atom is present between alkylene or alkenylene chains, such as $-L^3-X^1-L^4-$, $-L^3-X^1-L^4-X^2-L^5-$ and the like (in these formulae, $X^1$ and $X^2$ may be the same or different from each other and each represents an oxygen atom or a sulfur atom, and $L^3$, $L^4$ and $L^5$ may be the same or different from one another and each represents an alkylene group or an alkenylene group), but also the groups in which an oxygen atom and/or sulfur atom is directly linked to the

ring, such as $-X^1-L^3-$, $-L^3-X^1-$, $-X^1-L^3-X^2-L^4-$, $-L^3-X^1-L^4-X^2-$, $-X^1-L^3-X^2-L^2-X^3-$ and the like (in these formulae, $X^1$, $X^2$, $L^3$ and $L^4$ are as defined above, and $X^3$ may be the same as or different from $X^1$ and $X^2$ and represents an oxygen atom or a sulfur atom).

Preferably, these alkylene and alkenylene groups are straight chain groups having 1 (2 in the case of alkenylene groups) to 12 carbon atoms or branched-chain groups substituted with a lower alkyl group, and illustrative examples of such alkylene groups include methylene, ethylene, methylmethylene, trimethylene, 1-methylethylene, 2-methylethylene, tetramethylene, 1-methyltrimethylene, 2-methyltrimethylene, 3-methyltrimethylene, 1-ethylethylene, 2-ethylethylene, propylmethylene, isopropylmethylene, pentamethylene, 1, 2, 3 or 4-methyltetramethylene, 1, 2 or 3-ethyltrimethylene, 1,1-, 1,2-, 1,3-, 2,2-, 2,3- or 3,3-dimethyltrimethylene, hexamethylene, 1, 2, 3, 4 or 5-methylpentamethylene, 1, 2, 3 or 4-ethyltetramethylene, 1,1-, 1,2-, 1,3-, 1,4-, 2,2-, 2,3-, 2,4-, 3,3-, 3,4- or 4,4-dimethyltetramethylene, heptamethylene, 1, 2, 3, 4, 5 or 6-methylhexamethylene, octamethylene, 1, 2, 3, 4, 5, 6 or 7-methylheptamethylene, nonamethylene, 1, 2, 3, 4, 5, 6, 7 or 8-methyloctamethylene, decamethylene, 1, 2, 3, 4, 5, 6, 7, 8 or 9-methylnonamethylene, undecamethylene, 1, 2, 3, 4, 5, 6, 7, 8, 9 or 10-methyldecamethylene, dodecamethylene, 1, 2, 3, 4, 5, 6, 7, 8, 9, 10 or 11-methylundecamethylene and the like, and illustrative examples of alkenylene groups include vinylene, propenylene, 2-propenylene, 1-methylvinylene, 2-methylvinylene, butenylene, 2-butenylene, 3-butenylene, 1,3-butadienylene, 1-methylpropenylene, 1-methyl-2-propenylene, pentenylene, 1-methylbutenylene, 1-methyl-2-butenylene, 1-methyl-3-butenylene, 1,1-dimethyl-2-propenylene, hexenylene, 2-hexenylene, 3-hexenylene, 4-hexenylene, 5-hexenylene, 1,3-hexadienylene, 1,3,5-hexatrienylene, 1-methyl-2-pentenylene, 1-methyl-3-pentenylene, 1,1-dimethyl-2-butenylene, 1,1-dimethyl-3-butenylene, heptenylene, 2-heptenylene, 3-heptenylene, 4-heptenylene, 5-heptenylene, 6-heptenylene, 1,1-dimethyl-2-pentenylene, 1,1-dimethyl-3-pentenylene, 1,1-dimethyl-4-pentenylene, 2-octenylene, 4-octenylene, 7-octenylene, 1,3,5,7-octatetraenylene, 1,1-dimethyl-2-hexenylene, 1,1-dimethyl-3-hexenylene, 1,1-dimethyl-5-hexenylene, 2-nonenylene, 4-nonenylene, 5-nonenylene, 8-nonenylene, 1,1-dimethyl-2-heptenylene, 1,1-dimethyl-3-heptenylene, 1,1-dimethyl-4-heptenylene, 1,1-dimethyl-6-heptenylene, 2-decenylene, 5-decenylene, 9-decenylene, 1,1-dimethyl-2-octenylene, 1,1-dimethyl-4-octenylene, 1,1-dimethyl-7-octenylene, 2-undecenylene, 5-undecenylene, 6-undecenylene, 10-undecenylene, 1,1-dimethyl-2-nonenylene, 1,1-dimethyl-4-nonenylene, 1,1-dimethyl-5-nonenylene, 1,1-dimethyl-8-nonenylene, 2-dodecenylene, 6-dodecenylene, 11-dodecenylene, 1,1-dimethyl-2-decenylene, 1,1-dimethyl-5-decenylene, 1,1-dimethyl-9-decenylene and the like.

Preferred substituents which may substituted on these alkylene and alkenylene groups are halogen atoms, and illustrative examples of such halogen atoms include fluorine, chlorine, bromine, iodine and the like. One or two substituents may be contained.

The term "a cycloalkanediyl group, an arylene group or a pyridinediyl group which may respectively be substituted" represented by

means all of unsubstituted cycloalkanediyl groups, unsubstituted arylene groups, unsubstituted pyridinediyl groups, substituted cycloalkanediyl groups, substituted arylene groups and substituted pyridinediyl groups, preferred examples of cycloalkanediyl groups including those having 3 to 7 carbon atoms, such as cyclobutanediyl, cyclopentanediyl, cyclohexanediyl, cycloheptanediyl and the like, and each of these cycloalkanediyl groups may have 1 or 2 lower alkyl groups as its preferred substituents, and such lower alkyl groups include those described in the foregoing as illustrative examples of lower alkyl groups.

Examples of arylene groups include aromatic carbon ring divalent groups such as phenylene, naphthalenediyl, anthracenediyl, phenanthrenediyl and the like.

Substituents which may be substituted on arylene groups, pyridinediyl groups or the arylene group of

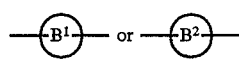

are not particularly limited, provided that they are used in the art as substituents of aromatic carbon rings and pyridine rings, and their preferred examples include a halogen atom, a lower alkyl group, a halogeno-lower alkyl group, a lower alkoxy group, a cyano group, a nitro group and the like, as well as an amino group or a carbamoyl group which may respectively be substituted with a lower alkyl group.

Illustrative examples of the "halogen atom" and "lower alkyl group" are those defined in the foregoing, and the term "halogeno-lower alkyl group" means a group in which optional hydrogen atom(s) of the aforementioned lower alkyl group are substituted with 1 or more halogen atoms. When a fluorine atom is used as an example of the halogen atom, illustrative examples of the halogeno-lower alkyl group include fluoromethyl, difluoromethyl, trifluoromethyl, 2,2,2-trifluoroethyl, pentafluoroethyl, 3,3,3-trifluoropropyl and the like.

Illustrative examples of the "lower alkoxy group" include methoxy, ethoxy, propoxy, isopropoxy, butoxy, isobutoxy, sec-butoxy, tert-butoxy, pentyloxy (amyloxy), isopentyloxy, tert-pentyloxy, neopentyloxy, 2-methylbutoxy, 1,2-dimethylpropoxy, 1-ethylpropoxy, hexyloxy and the like.

The term "amino group which may be substituted with a lower alkyl group" means unsubstituted amino group and amino groups mono- or di-substituted with the aforementioned illustrative lower alkyl groups, and illustrative examples of the lower alkyl-substituted amino group include mono-lower alkyl amino groups such as methylamino, ethylamino, propylamino, isopropylamino, butylamino, isobutylamino, sec-butylamino, tert-butylamino, pentyl (amyl)amino, isopentylamino, neopentylamino, tert-pentylamino, hexylamino and the like and symmetric or asymmetric di-lower alkyl amino groups such as dimethylamino, diethylamino, dipropylamino, diisopropylamino, dibutylamino, diisobutylamino, ethylmethylamino, methylpropylamino and the like.

Also, the term "carbamoyl group which may be substituted with a lower alkyl group" means unsubstituted carbamoyl group and carbamoyl groups mono- or di-substituted with the aforementioned illustrative lower alkyl groups, and illustrative examples of the lower alkyl-substituted carbamoyl group include mono-lower alkyl carbamoyl groups such as N-methylcarbamoyl, N-ethylcarbamoyl, N-propylcarbamoyl, N-isopropylcarbamoyl, N-butylcarbamoyl, N-isobutylcarbamoyl, N-sec-butylcarbamoyl, N-tert-butylcarbamoyl, N-pentylcarbamoyl, N-hexylcarbamoyl and the like and symmetric or asymmetric di-lower alkyl carbamoyl groups such as N,N-dimethylcarbamoyl, N,N-diethylcarbamoyl, N,N-dipropylcarbamoyl, N,N-dibutylcarbamoyl, N-ethyl-N-methylcarbamoyl, N-methyl-N-propylcarbamoyl, N-ethyl-N-propylcarbamoyl and the like.

Since the compound (I) of the present invention has acidic proton on its oxadiazolidine rings, it can form salts with bases. Pharmaceutically acceptable salts of the compound (I) are included in the present invention, and examples of such salts include salts with inorganic bases such as alkali metals (e.g., sodium and potassium), alkaline earth metals (e.g., magnesium and calcium) and trivalent metals (e.g., aluminum) and with organic bases such as methylamine, ethylamine, dimethylamine, diethylamine, trimethylamine, triethylamine, monoethanolamine, diethanolamine, triethanolamine, cyclohexylamine, lysine, ornithine and the like.

Since the compound of the present invention has an oxadiazolidine dione, tautomers based on the presence thereof exist. Also, since certain substituents have double bonds or asymmetric carbon atoms, geometrical isomers and optical isomers exist based on the presence thereof. All of these isomers in separated forms and mixtures thereof are included in the present invention.

In addition, since the compound (I) of the present invention and its salts are isolated in some cases in the form of hydrates or various solvates or as polymorphic substances, the present invention also include these hydrates, various pharmaceutically acceptable solvates such as with ethanol and the like and polymorphic substances.

Particularly preferred examples of the compound of the present invention are compounds in which the substituents which may be substituted on

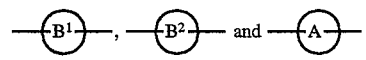

are one or more substituents selected from the group consisting of a halogen atom, a lower alkyl group, a halogeno-lower alkyl group, a lower alkoxy group, a cyano group, a nitro group, an amino group, a lower alkyl-substituted amino group, a carbamoyl group and a lower alkyl-substituted carbamoyl group and the substituents which may be substituted on the alkylene group and alkenylene group of $L^1$ and $L^2$ are one or more halogen atoms. More preferred examples are those in which

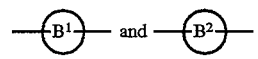

may be the same or different from each other and each represents a phenylene group which may be substituted with one or more substituents selected from the group consisting of a halogen atom, a lower alkyl group and a halogeno-lower alkyl group and L is 1) an alkylene group or an alkenylene group which may respectively be interrupted with an oxygen atom and/or a sulfur atom and which may respectively be substituted with one or more halogen atoms, or 2) a group represented by

wherein $L^1$ and $L^2$ are respectively an alkylene group or an alkenylene group which may respectively be interrupted with an oxygen atom and/or a sulfur atom and which may respectively be substituted with one or more halogen atoms and

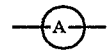

is a cycloalkanediyl group, an arylene group or a pyridinediyl group which may respectively be substituted with one or more substituents selected from the group consisting of a halogen atom, a lower alkyl group, a halogeno-lower alkyl group, a lower alkoxy group, a cyano group, a nitro group, an amino group, a lower alkyl-substituted amino group, a carbamoyl group and a lower alkyl-substituted carbamoyl group.

The following illustrates most preferred examples of the compound of the present invention.

(1) 1,3-Bis[4-[(3,5-dioxo-1,2,4-oxadiazolidin-2-yl)methyl]phenoxy]benzene or a pharmaceutically acceptable salt thereof.
(2) 1,4-Bis[4-[(3,5-dioxo-1,2,4-oxadiazolidin-2-yl)methyl]phenoxy]-2-butene or a pharmaceutically acceptable salt thereof (particularly its (Z) form).
(3) 1,9-Bis[4-[(3,5-dioxo-1,2,4-oxadiazolidin-2-yl)methyl]phenoxy]nonane or a pharmaceutically acceptable salt thereof.

(Production Method)

The compound of the present invention can be produced by employing various synthesis methods making use of the characteristics of its basic structure or its substituents. The following illustrates typical examples of the production method.

First Production Method

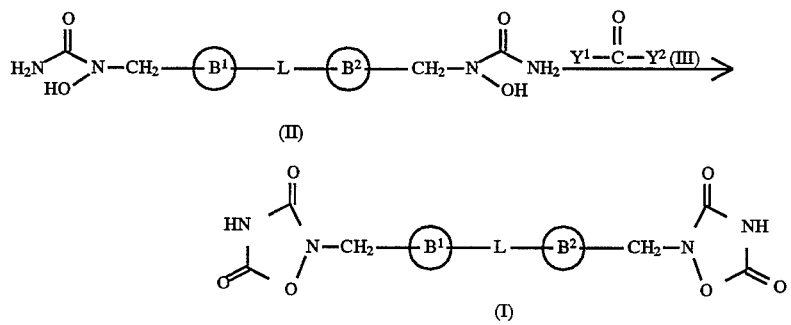

(In the above formulae,

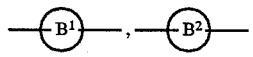

and L are as defined in the foregoing, and $Y^1$ and $Y^2$ may be the same or different from each other and each represents a halogen atom, an alkoxy group, an aralkyloxy group or an aryloxy group.)

The compound (I) of the present invention is produced by allowing a bis(N-carbamoyl-N-hydroxyaminomethyl) derivative represented by the general formula (II) to react with a carbonyl compound represented by the general formula (III).

In this case, examples of the halogen atom represented by $Y^1$ and $Y^2$ are as defined in the foregoing, and lower alkoxy groups (e.g., methoxy and ethoxy) may generally be used as the alkoxy group though not particularly limited to these lower alkoxy groups. The aryloxy and aralkyloxy groups are not particularly limited, provided that they are aromatic carbon ring-oxy groups or aromatic carbon ring-alkoxy groups, and phenoxy, benzyloxy and the like may generally be used.

It is advantageous to carry out the reaction between the compound (II) with 2 mol or excess mol equivalent of the compound (III), preferably, in the presence of a base such as sodium hydroxide, potassium hydroxide or the like at a temperature of from 0° C. to 150° C. in an inert organic solvent such as tetrahydrofuran, diethyl ether, diisopropyl ether, dioxane, dimethoxyethane (monoglyme), bis(2-methoxyethyl) ether (diglyme), methanol, ethanol, Cellosolve (trade name, 2-ethoxyethanol), Methylcellosolve (trade name, 2-methoxyethanol), dimethyl sulfoxide, sulfolane or the like, or a mixture thereof.

In this connection, as shown in the following reaction scheme, the starting compound (II) can be obtained easily by 1) reducing the corresponding bis(formyl) compound (IV) to obtain a bis(hydroxymethyl) compound, halogenizing the product to obtain a bis(halogenomethyl) compound, allowing the halogeno compound to react with protected hydroxy-urea to obtain a bis(N-protected hydroxy-N-carbamoylaminomethyl) compound (VI) and then eliminating the protecting group, or 2) subjecting the corresponding formyl compound (IV) to reductive amination with hydroxylamine using a reducing agent to obtain a bis(hydroxyaminomethyl) compound (VII) and allowing the thus obtained compound to react with an alkali metal cyanate in the presence of water.

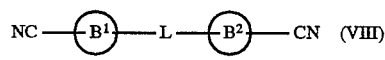

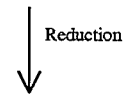

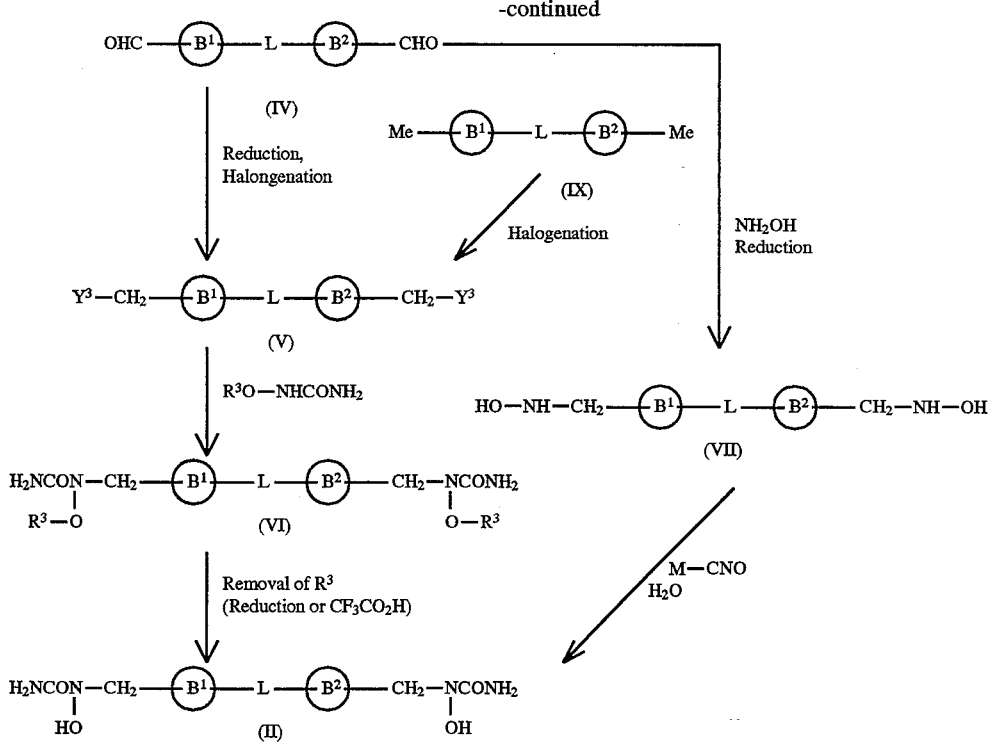

(In the above formulae,

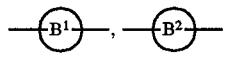

and L are as defined in the foregoing, $Y^3$ represents a halogen atom, $R^3$ represents an easily removable protecting group for the hydroxyl group and M represents an alkali metal.)

In this case, the halogen atom and alkali metal are as defined in the foregoing, and examples of the protecting group for the hydroxyl group include those which can be easily eliminated, such as aralkyl groups (e.g., benzyl and p-methoxybenzyl), lower alkyl groups (e.g., tert-butyl) and acyl groups (e.g., acetyl, trifluoroacetyl, and benzyloxycarbonyl).

The reaction of each step can be carried out by employing generally used methods. For example, the reaction for the production of the bis(halogenomethyl) compound (V) from the bis(formyl) compound (IV) may be effected preferably in an inert organic solvent such as alcohols (e.g., methanol), ethers (e.g., tetrahydrofuran), or a mixture thereof, by reducing the starting compound using a reducing agent such as sodium borohydrate or the like which is generally used for the production of —$CH_2OH$ from —CHO and allowing the reduced product to react with a halogenation agent such as a hydrogen halide. Also, the reaction for the production of the bis[N-(protected hydroxy)-N-carbamoylaminomethyl] compound from the compound (V) may be effected by allowing the compound (V) to react with a protected hydroxyurea in an inert organic solvent such as dimethylformamide or the like which is generally used in the N-alkylation reaction, preferably in the presence of a base such as sodium hydride, potassium carbonate or the like, which is usually used in the N-alkylation reaction. Elimination of the protecting group, though its varies depending on the type of the protecting group, may be effected by treating the compound with trifluoroacetic acid or the like acid which is usually used in the elimination of hydroxyl-protecting groups or, in the case of a protecting group such as a benzyl group, by reducing it for example by catalytic reduction in the presence of a catalyst such as Pd—C or the like.

The reaction for the production of the bis(hydroxymethyl) compound (VII) from the compound (IV) may be effected by allowing the compound (IV) to react with hydroxylamine or a salt thereof and reducing the thus formed Schiff's base using a reducing agent (e.g., a borane-pyridine complex and sodium borohydrate), which is usually used in the reductive amination, in an inert solvent, for example, in an organic solvent such as alcohols (e.g., methanol and ethanol) or aromatic hydrocarbons (e.g., benzene, toluene, and xylene), or in water or a mixture solvent thereof, if necessary, in the presence of a catalyst such as sodium acetate, p-toluenesulfonic acid or the like and using an azeotropic dehydration apparatus or a dehydrating agent, if necessary. The Schiff's base can be applied to the reduction step without isolation.

The reaction for the production of the compound (II) from the compound (VII) may be effected by allowing the compound (VII) to react with an alkali metal cyanate in an inert organic solvent such as alcohols (e.g., methanol and ethanol), ether (e.g., tetrahydrofuran) or a mixture thereof, if necessary, in the presence of an acid catalyst such as hydrochloric acid or the like.

Taking types, etc. of

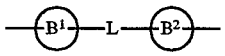

into consideration, the bis(formyl) compound (IV) may be produced by various methods, for example, by employing etherification or thioetherification in which the corresponding halide or sulfonate is allowed to react with phenol or thiophenol in the presence of a base, or by reducing the corresponding bis(nitrile) compound (VIII) using a reducing agent such as diisobutyl aluminum hydride or the like. When the bis(tolyl) compound (IX) is used as a starting material, the bis(halogenomethyl) compound (V) can also be produced by allowing the starting material to react with a halogenation agent.

Second Production Method (In the above formulae,

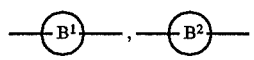

L and $Y^5$ are as defined in the foregoing.)

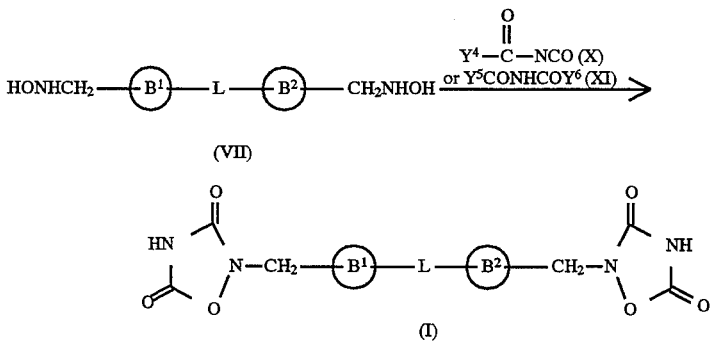

(In the above formulae,

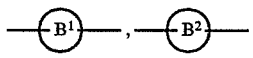

and L are as defined in the foregoing, $Y^4$ represents a halogen atom or an alkoxy group, and $Y^5$ and $Y^6$ may be the same or different from each other and each represents a halogen atom, an alkoxy group, an aralkyloxy group or an aryloxy group.)

The compound (I) of the present invention can be produced also by using the corresponding bis(hydroxyaminomethyl) compound (VII) as a starting material and allowing it to react with isocyanates (X) represented by the general formula (X) or N-acyl acid imides (XI).

Illustrative examples of the halogen atom, alkoxy group, aralkyloxy group and aryloxy group are as defined in the foregoing.

Though it varies depending on the type of the starting compound, it is advantageous to carry out the reaction of the compound (VII) with 2 mol or excess mol equivalent of the compound (X) or (XI) at a cooling temperature to room temperature in an inert solvent, for example, in an organic solvent such as tetrahydrofuran, dioxane, ethers (e.g., diethyl ether), dimethylformamide, dimethyl sulfoxide or the like or a mixture solvent thereof, if necessary, in the presence of a base such as sodium hydroxide, potassium hydroxide, trimethylamine, triethylamine or the like.

Third Production Method

The compound (I) of the present invention can be produced also by cyclizing the corresponding bis(N-hydroxy-N-acylaminocarbonylaminomethyl) compound (XII) through its treatment with a base.

The base used in the third production method is also used in this reaction, and the compound (XII) is an intermediate of the third production method, because it is produced in the third production method by allowing the compound (VII) to react with the compound (X) in the absence of base.

In consequence, the base-treatment reaction is carried out in the same manner as described in the third production method.

Fourth Production Method

A member of the compound of the present invention in which L, $L^1$ and/or $L^2$ is —SO— or —SO$_2$— can be produced also by oxidizing the corresponding compound having —S— or —SO—.

The oxidation can be carried out by applying generally used methods advantageously using oxidizing agent such as organic peracids (e.g., performic acid, peracetic acid, perbenzoic acid, m-chloroperbenzoic acid, perphthalic acid) or hydrogen peroxide.

Other Production Method

Since the compound of the present invention has ether (thioether), amide, imino and similar structures, it can be produced by employing conventional methods such as the aforementioned etherification, thioetherification, amidation, N-alkylation, reductive amination and the like.

The compound of the present invention produced in this manner is isolated and purified as a free compound or its salt,

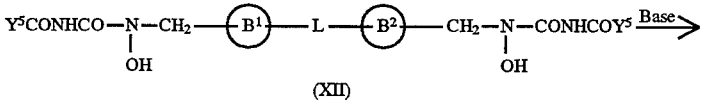

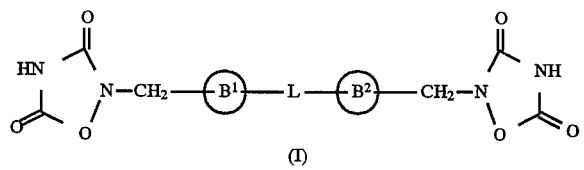

hydrate or various types of solvate. Pharmaceutically acceptable salts of the compound (I) of the present invention can be produced by subjecting it to a conventional salt forming reaction.

Isolation and purification are carried out by employing generally used chemical techniques such as extraction, fractional crystallization, various types of separation chromatography and the like.

Tautomers and geometrical isomers can be separated by selecting appropriate starting material or making use of a difference in physicochemical property between isomers.

Also, optical isomers can be made into stereochemically pure isomers by selecting an appropriate starting material or by racemic resolution of a racemic compound (for example, a method in which a compound is converted into a diastereomer salt with a general optically active base and then subjected to optical resolution).

INDUSTRIAL APPLICABILITY

Since the compound (I) of the present invention and its salts and the like have excellent hypoglycemic action based on their insulin sensitivity-increasing action, are low in toxicity and hardly cause side effects, they are useful as a drug for the prevention and treatment of diabetes, particularly non-insulin-dependent diabetes (type II), and various types of diabetic complication and as a drug to be used in combination with insulin.

The excellent hypoglycemic action of the compound of the present invention based on its insulin sensitivity-increasing action was confirmed by the following test methods.

Hypoglycemic Action

Male kk mice of 4 to 5 w were purchased from CLEA Japan Inc. These animals were separately reared with a high calorie food (CMF, manufactured by Oriental Yeast), and the animals of which the body weight was more than 40 g were used in the test.

Measurement of the blood sugar level was carried out by collecting a 10 µl portion of blood from a tail vein, removing protein from the collected sample by its treatment with 100 µl of 0.33N perchloric acid, and after centrifugation, measuring glucose in the resulting supernatant by the glucose oxidase method. Six animals having a blood sugar level of more than 200 mg/dl were used as one group in the test.

Each drug was suspended in 0.5% methyl cellulose and orally administered daily for 4 days. Blood samples were collected before and on the fifth day of the drug administration from the tail vein. Blood sugar level was determined with the aforementioned method.

The hypoglycemic activity was expressed as the blood sugar level decreasing ratio to the pre-administration level and statistically evaluated as a significant threshold value of $p=0.05$.

\*=$p<0.05$
\*\*=$p<0.01$
\*\*\*=$p<0.001$

As the result, the compound of the present invention showed excellent hypoglycemic action. For example, the compound of Example 6 showed 53%\*\*\* of blood sugar level decreasing ratio with a dose of 30 mg/day. In addition, low toxicity of the compound of the present invention has been confirmed by a toxicity test.

A pharmaceutical composition which contains one or more of the compound represented by the general formula (I) and pharmaceutically acceptable salts thereof as the active ingredient is prepared as various dosage forms such as tablets, powders, fine granules, granules, capsules, pills, solutions, injections, suppositories and the like making use of generally used pharmaceutical carriers, excipients and other additives, and is administered orally or parenterally.

Clinical dose of the compound of the present invention to be used in human is optionally decided taking into consideration the symptoms, body weight, age, sex and the like of each patient and is generally from 1 to 2,000 mg per day per adult for oral administration, and the daily dose recited above may be used once a day or divided into several doses per day. Since the dose varies under various conditions, a dose smaller than the above range may exert full effect in some cases.

Tablets, powders, granules and the like are used as the solid composition for oral administration use of the present invention. In such solid composition, one or more active substances are mixed with at least one inert diluent such as lactose, mannitol, glucose, hydroxypropylcellulose, fine crystalline cellulose, starch, polyvinylpyrrolidone, magnesium metasilicate aluminate or the like. In addition to the inert diluent, the composition may also contain other inactive additive agents in the usual way, which include a lubricant such as magnesium stearate, a disintegrator such as fibrin calcium glycolate, a stabilizer such as lactose and a solubilizing or solubilization assisting agent such as glutamic acid or aspartic acid. If necessary, tablets or pills may be coated with a gastric or enteric films such as sucrose, gelatin, hydroxypropylcellulose, hydroxypropylmethylcellulose phthalate or the like.

Examples of the liquid composition for use in oral administration contains pharmaceutically acceptable emulsions, solutions, suspensions, syrups, elixirs and the like, which contain generally used inert diluents such as purified water, ethanol and the like. In addition to the inert diluent, this composition may also contain a solubilizing or solubilization assisting agent, auxiliary agents (e.g., a moistening agent), a suspension, a sweetener, a flavoring agent, an aromatic agent, an antiseptic agent and the like.

Examples of injections for parenteral administration use include aseptic aqueous or non-aqueous solutions, suspensions and emulsions. Diluents of aqueous solutions and suspensions include, for example, distilled water for injection use and physiological saline. Examples of diluents for use in the non-aqueous solutions and suspensions include propylene glycol, polyethylene glycol, plant oils (e.g., olive oil), alcohols (e.g., ethanol) and Polysolvate 80 (trade name). Such compositions may further contain additive agents such as a tonicity agent, an antiseptic agent, a moistening agent, an emulsifying agent, a dispersing agent, a stabilizing agent (e.g., lactose), a solubilizing or solubilization assisting agent and the like. These agents are sterilized, for example, by filtration through a bacteria-removing filter, addition of a bactericide or irradiation. Alternatively, a sterile solid composition may first be produced, which is then dissolved in sterile water or a sterile injection solvent prior to its use.

BEST MODE OF CARRYING OUT THE INVENTION

The following examples are provided to describe the present invention further in detail.

Since novel compounds are included in the starting materials, examples of their production are shown in the following as Reference Examples.

Reference Example 1

1,3-Bis(4-formylphenoxy)benzene (6.36 g) was dissolved in a mixed solvent of 30 ml methanol and 60 ml tetrahydrofuran to which, with ice-cooling, was subsequently added 0.76 g of sodium borohydride. After 30 minutes of stirring with ice-cooling, the solution was mixed with 80 ml of 1N hydrochloric acid and extracted with ethyl acetate. The extract was dried over anhydrous magnesium sulfate, and the solvent was evaporated. The thus obtained residue was dissolved in a 4N hydrogen chloride-1,4-dioxane solution and the solution was stirred for 2 hours at room temperature. The solvent was evaporated under a reduced pressure, and the residue was subjected to silica gel column chromatography (hexane:ethyl acetate=9:1) to obtain 6.0 g of 1,3-bis [(4-chloromethyl)phenoxy]benzene.

Melting point: 37°–39° C.

Nuclear magnetic resonance spectrum (DMSO-d₆, TMS internal standard)

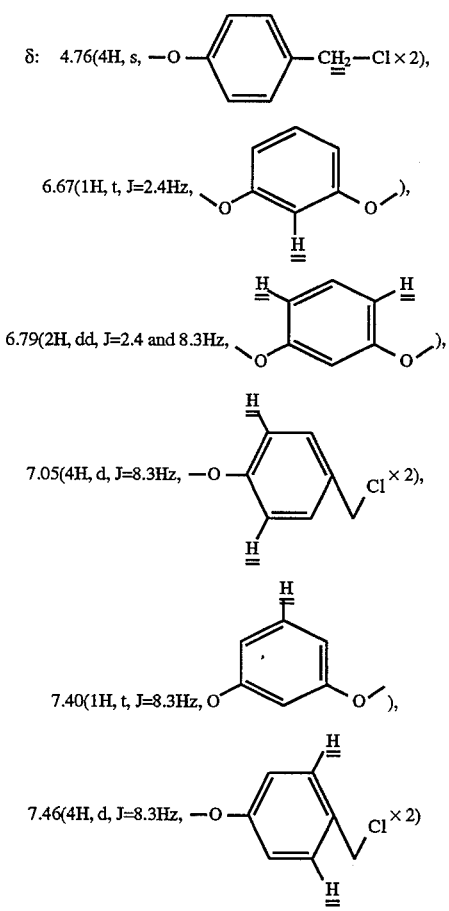

Reference Example 2

2,7-Bis(4-formylphenoxy)naphthalene (2.24 g, 6.09 mmol) was dissolved in a mixed solvent of methanol (20 ml) and tetrahydrofuran (20 ml) to which, with ice-cooling, was subsequently added sodium borohydride (0.576 g, 15.2 mmol). After 1 hour of stirring at room temperature, the solution was mixed with 1N hydrochloric acid (60 ml) and extracted with ethyl acetate. The extract was dried over anhydrous magnesium sulfate and then the solvent was evaporated.

The thus obtained residue (1.7 g) was added to a 4N hydrogen chloride-1,4-dioxane solution (20 ml) and the mixture was stirred for 3 hours at room temperature. After completion of the reaction, the solvent was evaporated and the resulting powder was washed with water and diethyl ether and then dried to obtain 2,7-bis(4-chloromethylphenoxy)naphthalene (1.41 g, 57%).

Melting point: 95°–97° C.

Mass spectrometry data (m/z): 409 (M⁺)

Nuclear magnetic resonance spectrum (DMSO-d₆, TMS internal standard)

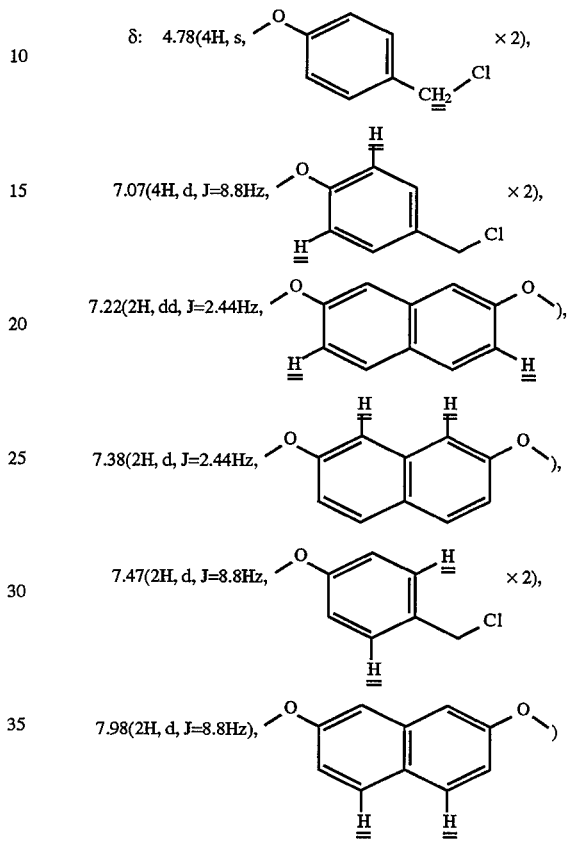

The following compounds were obtained in the same manner as described in Reference Examples 1 and 2.

Bis[(4-chloromethyl)phenyl]ether;
Bis[(4-chloromethyl)phenyl]methane;
1,4-Bis[(4-chloromethyl)phenoxy]benzene;
1,5-Bis[(4-chloromethyl)phenoxy]pentane;
Trans-1,4-bis[[(4-chloromethyl)phenoxy]methyl] cyclohexane;
Cis-1,3-bis[(4-chloromethyl)phenoxy]cyclohexane;
1,2-Bis[(4-chloromethyl)phenoxy]benzene;

Reference Example 3

Dimethylformamide (150 ml) was added to 21.3 g of 1,9-dibromononane, 19.8 g of 4-hydroxybenzaldehyde and 21.7 g of potassium carbonate, and the mixture was stirred at 90° C. for 1.5 hours. The reaction mixture was cooled to room temperature and poured into water, and the thus formed precipitate was washed with water and then dried under a reduced pressure to obtain 26.9 g of 1,9-bis(4-formylphenoxy)nonane.

Mass spectrometry data (m/z): 368 (M⁺)

Nuclear magnetic resonance spectrum (DMSO-d₆, TMS internal standard)

δ: 1.20–1.30 (10H, m), 1.65–1.80 (4H, m), 4.07 (4H, t), 7.11 (4H, d), 7.86 (4H, d), 9.86 (2H, s)

The following compounds were obtained in the same manner as described in Reference Example 3.

Reference Example 4

(Z)-1,4-Bis(4-formylphenoxy)-2-butene

Mass spectrometry data (m/z): 296 (M$^+$)

Nuclear magnetic resonance spectrum (CDCl$_3$, TMS internal standard)

δ: 4.78 (4H, d), 5.97 (2H, t), 7.02 (4H, d), 7.84 (4H, d), 9.90 (2H, s)

Reference Example 5

1,6-Bis(4-formylphenoxy)hexane

Mass spectrometry data (m/z): 326 (M$^+$)

Nuclear magnetic resonance spectrum (CDCl$_3$, TMS internal standard)

δ: 1.75–1.55 (4H, m), 1.75–1.85 (4H, m), 4.10 (4H, t), 7.12 (4H, d), 7.83 (4H, d), 9.89 (2H, s)

Reference Example 6

1,4-Bis(4-formylphenoxy)butane

Mass spectrometry data (m/z): 299 ([M+H]$^+$)

Nuclear magnetic resonance spectrum (CDCl$_3$, TMS internal standard)

δ: 1.70–1.55 (4H, m), 4.14 (4H, m), 7.00 (4H, d), 7.83 (4H, d), 9.89 (2H, s)

Reference Example 7

(E)-1,4-Bis(4-formylphenoxy)-2-butene

Mass spectrometry data (m/z): 297 ([M+H]$^+$)

Nuclear magnetic resonance spectrum (CDCl$_3$, TMS internal standard)

δ: 4.68 (4H, dd), 6.11 (2H, m), 7.03 (4H, d), 7.83 (4H, d), 9.89 (2H, s)

Reference Example 8

1,7-Bis(4-formylphenoxy)heptane

Mass spectrometry data (m/z): 340 (M$^+$)

Nuclear magnetic resonance spectrum (CDCl$_3$, TMS internal standard)

δ: 1.10–2.10 (10H, m), 4.05 (4H, t), 6.98 (4H, d), 7.82 (4H, d), 9.88 (2H, s)

Reference Example 9

1,3-Bis[(4-formylphenoxy)methyl]benzene

Mass spectrometry data (m/z): 346 (M$^+$)

Nuclear magnetic resonance spectrum (CDCl$_3$, TMS internal standard)

δ: 5.17 (4H, s), 7.07 (4H, d), 7.30–7.70 (4H, m), 7.74 (4H, d), 9.89 (2H, s)

Reference Example 10

1,5-Bis(4-formylphenoxy)-3,3-dimethylpentane

Mass spectrometry data (m/z): 340 (M$^+$)

Nuclear magnetic resonance spectrum (CDCl$_3$, TMS internal standard)

δ: 1.09 (6H, s), 1.87 (4H, t), 4.16 (4H, t), 6.97 (4H, t), 7.87 (4H, t), 9.88 (2H, s)

Reference Example 11

Cis-1,3-bis(4-formylphenoxy)cyclopentane

Mass spectrometry data (m/z): 311 ([M+H]$^+$)

Nuclear magnetic resonance spectrum (CDCl$_3$, TMS internal standard)

δ: 1.70–7.50 (6H, m), 4.90–5.20 (2H, m), 6.98 (4H, d), 7.83 (4H, d), 9.89 (2H, s)

Reference Example 12

Trans-1,3-bis(4-formylphenoxy)cyclopentane

Mass spectrometry data (m/z): 311 ([M+H]$^+$)

Nuclear magnetic resonance spectrum (CDCl$_3$, TMS internal standard)

δ: 2.10–2.25 (5H, m), 2.51–2.58 (1H, m), 4.88–4.95 (2H, m), 6.97 (4H, d), 8.82 (4H, d), 9.87 (2H, s)

The following compounds were obtained in the same manner as described in Reference Example 4.

Reference Example 13

1,8-Bis(4-formylphenoxy)octane

Mass spectrometry data (m/z): 354 (M$^+$)

Nuclear magnetic resonance spectrum (CDCl$_3$, TMS internal standard)

δ: 0.90–2.00 (12H, m), 4.04 (4H, t), 6.99 (4H, d), 7.83 (4H, d), 9.88 (2H, s)

Reference Example 14

2,2'-Bis(4-formylphenoxy)ethyl ether

Mass spectrometry data (m/z): 314 (M$^+$)

Nuclear magnetic resonance spectrum (CDCl$_3$, TMS internal standard)

δ: 3.80–4.10 (4H, m), 4.10–4.25 (4H, m), 7.02 (4H, d), 7.85 (4H, d), 9.87 (2H, s)

Reference Example 15

1,2-Bis(4-formylphenoxy)ethane

Mass spectrometry data (m/z): 271 ([M+H]$^+$)

Nuclear magnetic resonance spectrum (CDCl$_3$, TMS internal standard)

δ: 4.45 (4H, m), 7.06 (4H, d), 7.86 (4H, d), 9.91 (2H, s)

Reference Example 16

1,3-Bis(4-formylphenoxy)propane

Mass spectrometry data (m/z): 285 ([M+H]$^+$)

Nuclear magnetic resonance spectrum (CDCl$_3$, TMS internal standard)

δ: 2.34 (2H, quint), 4.27 (4H, t), 7.01 (4H, d), 7.83 (4H, d), 9.88 (2H, s)

Reference Example 17

1,10-Bis(4-formylphenoxy)decane

Mass spectrometry data (m/z): 383 ([M+H]$^+$)

Nuclear magnetic resonance spectrum (CDCl$_3$, TMS internal standard)

δ: 0.90–2.00 (16H, m), 4.04 (4H, t), 6.98 (4H, d), 7.82 (4H, d), 9.87 (2H, s)

Reference Example 18

1,11-Bis(4-formylphenoxy)undecane

Mass spectrometry data (m/z): 397 ([M+H]$^+$)

Nuclear magnetic resonance spectrum (CDCl$_3$, TMS internal standard)

δ: 0.90–2.00 (18H, m), 4.04 (4H, t), 7.00 (4H, d), 7.84 (4H, d), 9.88 (2H, s)

Reference Example 19

1,12-Bis(4-formylphenoxy)dodecane

Mass spectrometry data (m/z): 411 ([M+H]$^+$)

Nuclear magnetic resonance spectrum (CDCl$_3$, TMS internal standard)

δ: 0.90–2.00 (20H, m), 4.04 (4H, t), 6.98 (4H, d), 7.82 (4H, d), 9.87 (2H, s)

Reference Example 20

1,5-Bis(4-formylphenoxy)-2,2,3,3,4,4-hexafluoropentane

Mass spectrometry data (m/z): 421 ([M+H]$^+$)

Nuclear magnetic resonance spectrum (CDCl$_3$, TMS internal standard)

δ: 4.58 (4H, s), 7.08 (4H, d), 7.91 (4H, d), 9.93 (2H, s)

Reference Example 21 p-Fluorobenzaldehyde (7.7 g), 5.9 g of 5-chlororesorcinol and 12.3 g of anhydrous potassium carbonate were added to 50 ml of dimethyl sulfoxide and stirred for 12 hours at 100° C. After completion of the reaction, 100 ml of water and 200 ml of ethyl acetate were added to carry out phase separation. After three times of washing with 50 ml of 10% sodium chloride aqueous solution and subsequent drying over anhydrous magnesium sulfate, the solvent was evaporated. The resulting oily material was subjected to silica gel column chromatography (hexane:ethyl acetate (7:1)) to obtain 3.5 g of 1,3-bis(4-formylphenoxy)-5-chlorobenzene.

Mass spectrometry data (m/z): 352 (M$^+$) (GC-MS)

Nuclear magnetic resonance spectrum (CDCl$_3$, TMS internal standard)

δ: 6.69 (1H, t, phenyl), 6.88 (1H, d, phenyl), 7.14 (4H, d, phenyl), 7.90 (4H, d, phenyl), 9.95 (2H, s, —CHO)

Reference Example 22

(a) 3,5-Dihydroxytoluol (3.72 g) and 7.62 g of 4-fluorobenzonitrile were dissolved in 50 ml of dimethyl sulfoxide to which was subsequently added 2.52 g of 60% sodium hydride. After 4 hours of stirring at 60° C., ice water and ethyl acetate were added to separate the organic layer. The organic layer was washed with 10% potassium carbonate aqueous solution and dried over anhydrous magnesium sulfate, and then the solvent was evaporated. The residue was recrystallized from isopropanol to obtain 5.5 g of 1,3-bis(4-cyanophenoxy)-5-methylbenzene.

Mass spectrometry data (m/z): 326 (M$^+$)

Nuclear magnetic resonance spectrum (CDCl$_3$, TMS internal standard)

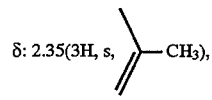

δ: 2.35(3H, s, —CH$_3$),

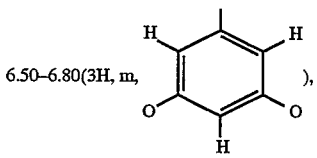

6.50–6.80(3H, m, ),

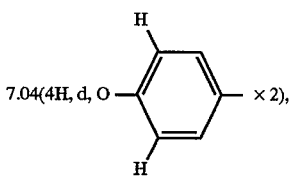

7.04(4H, d, O ×2),

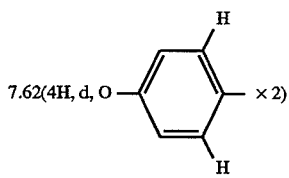

7.62(4H, d, O ×2)

(b) 1,3-Bis(4-cyanophenoxy)-5-methylbenzene (7.06 g) was dissolved in 150 ml of methylene chloride, and 53.1 ml of aluminum diisobutylhydride (1.02M toluene solution) was added dropwise to the solution which was ice-cooled. After 30 minutes of stirring with ice-cooling, 100 ml of saturated ammonium chloride aqueous solution and 5% sulfuric acid were added thereto and the resulting organic layer was separated. The organic layer was washed with saturated sodium chloride aqueous solution and dried over anhydrous magnesium sulfate and then the solvent was evaporated. Diisopropyl ether was added to the resulting residue and the thus formed crystals were collected by filtration to obtain 6.5 g of 1,3-bis(4-formylphenoxy)-5-methylbenzene.

Mass spectrometry data (m/z): 332 (M$^+$)

Nuclear magnetic resonance spectrum (DMSO-d$_6$, TMS internal standard)

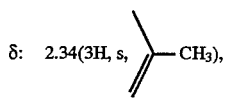

δ: 2.34(3H, s, —CH$_3$),

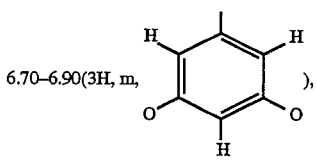

6.70–6.90(3H, m, ), 7.21(4H, d, —O—[benzene ring with H at 2 positions]—×2), 7.94(4H, d, —O—[benzene ring with H at 2 positions]—×2), 9.95(2H, s, —C(=O)—H ×2)

Reference Example 23

(a) 40% Potassium fluoride-alumina (3 g) and 0.4 g of 18-crown-6-ether were added to 50 ml of acetonitrile solution containing 1.55 g of resorcinol and 5.34 g of 4-fluoro-3-trifluoromethylbenzonitrile. After heating the reaction mixture overnight under reflux, insoluble materials were separated by filtration, diluted with water and extracted with ethyl acetate. The organic layer was washed with water and saturated sodium chloride aqueous solution and then dried over anhydrous magnesium sulfate. The solvent was evaporated under a reduced pressure and the resulting residue was recrystallized from hexane-ethyl acetate to obtain 2.40 g of 1,3-bis(4-cyano-2-trifluoromethylphenoxy)benzene.

Mass spectrometry data (m/z): 449 ([M+H]$^+$)

Nuclear magnetic resonance spectrum (CDCl$_3$, TMS internal standard)

δ: 6.88 (1H, t), 6.98–7.03 (4H, m), 7.51 (1H, t), 7.77 (2H, d), 7.99 (2H, d)

(b) 1,3-Bis(4-formyl-2-trifluoromethylphenoxy)benzene was obtained in the same manner as described in Reference Example 22 (b).

Mass spectrometry data (m/z): 455 ([M+H]$^+$)

Nuclear magnetic resonance spectrum (CDCl$_3$, TMS internal standard)

δ: 6.90 (1H, t), 6.99–7.02 (2H, m), 7.07 (2H, d), 7.50 (1H, t), 8.01 (2H, d), 8.22 (2H, d), 9.98 (2H, s)

Reference Example 24

(a) Anhydrous trifluoroacetic acid (20 ml) was added to 20 ml of dichloromethane solution containing 1.53 g of 3-(4-cyanophenoxy)aniline, and the reaction mixture was stirred for 30 minutes at room temperature. The solvent was evaporated under a reduced pressure, and the thus obtained residue was dissolved in 40 ml of 2-butanone. Then, 3.14 g of methyl iodide and 2.09 g of potassium carbonate were added thereto. The reaction mixture was heated for 3 hours under reflux, insoluble materials were separated by filtration, and the solvent was evaporated under a reduced pressure. To the thus obtained residue were added 30 ml of methanol, 20 ml of water and 1.10 g of potassium carbonate. The reaction mixture was heated for 2 hours under reflux, diluted with water and then extracted with ethyl acetate. The organic layer was washed with saturated sodium chloride aqueous solution and then dried over anhydrous magnesium sulfate. The solvent was evaporated under a reduced pressure, and the resulting residue was purified by silica gel column chromatography (eluant; hexane:ethyl acetate=2:1) to obtain 1.52 g of 3-(4-cyanophenoxy)-N-methylaniline.

Mass spectrometry data (m/z): 224 (M$^+$)

Nuclear magnetic resonance spectrum (CDCl$_3$, TMS internal standard)

δ: 2.82 (3H, s), 3.86 (1H, s), 6.29 (1H, t), 6.36 (1H, d), 6.46 (1H, d), 7.02 (2H, d), 7.18 (1H, t), 7.58 (2H, d)

(b) The following compound was obtained in the same manner as described in Reference Example 22 (a).

3-(4-Cyanophenoxy)-N-(4-cyanophenyl)-N-methylaniline

Starting compound: 3-(4-cyanophenoxy)-N-methylaniline

Mass spectrometry data (m/z): 325 (M$^+$)

Nuclear magnetic resonance spectrum (CDCl$_3$, TMS internal standard)

δ: 3.37 (3H, s), 6.83–6.91 (4H, m), 7.04–7.06 (3H, m), 7.42 (1H, t), 7.47 (2H, d), 7.63 (2H, d)

(c) The following compound was obtained in the same manner as described in Reference Example 22 (b).

3-(4-Formylphenoxy)-N-(4-formylphenyl)-N-methylaniline

Starting compound: 3-(4-cyanophenoxy)-N-(4-cyanophenyl)-N-methylaniline

Mass spectrometry data (m/z): 331 (M$^+$)

Nuclear magnetic resonance spectrum (CDCl$_3$, TMS internal standard)

δ: 3.41 (3H, s), 6.88–6.97 (4H, m), 7.07–7.12 (3H, m), 7.44 (1H, t), 7.72 (2H, d), 7.86 (2H, d), 9.79 (1H, s), 9.94 (1H, s)

Reference Example 25

(a) The following compound was obtained in the same manner as described in Reference Example 23 (a).

1,3-Bis(4-cyano-2,6-difluorophenoxy)benzene

Mass spectrometry data (m/z): 385 ([M+H]$^+$)

Nuclear magnetic resonance spectrum (CDCl$_3$, TMS internal standard)

δ: 6.78–6.81 (2H, m), 6.95 (1H, t), 7.35 (1H, t), 8.07 (4H, d)

(b) The following compound was obtained in the same manner as described in Reference Example 22 (b).

1,3-Bis(4-formyl-2,6-difluorophenoxy)benzene

Mass spectrometry data (m/z): 391 ([M+H]$^+$)

Nuclear magnetic resonance spectrum (CDCl$_3$, TMS internal standard)

δ: 6.64–6.71 (3H, m), 7.24 (1H, t), 7.57 (4H, d), 9.93 (2H, s)

Reference Example 26

(a) The following compound was obtained in the same manner as described in Reference Example 23 (a).

1,3-Bis(4-cyano-3-trifluoromethylphenoxy)benzene

Mass spectrometry data (m/z): 449 ([M+H]$^+$)

Nuclear magnetic resonance spectrum (CDCl$_3$, TMS internal standard)

δ: 7.16–7.20 (3H, m), 7.44–7.47 (2H, m), 7.60–7.64 (3H, m), 8.16 (2H, d)

(b) The following compound was obtained in the same manner as described in Reference Example 22 (b).

1,3-Bis(4-formyl-3-trifluorophenoxy)benzene

Mass spectrometry data (m/z): 455 ([M+H]$^+$)

Nuclear magnetic resonance spectrum (CDCl$_3$, TMS internal standard)

δ: 6.85 (1H, t), 6.98–7.01 (2H, m), 7.22–7.27 (2H, m), 7.37 (2H, d), 7.51 (1H, t), 8.14 (2H, d), 10.30 (2H, s)

The following compounds were obtained in the same manner as described in Reference Example 3.

Reference Example 27

1,3-Bis(4-formylphenoxy)-4-nitrobenzene

Mass spectrometry data (m/z): 363 (M$^+$)

Nuclear magnetic resonance spectrum (CDCl$_3$, TMS internal standard)

δ: 6.8–7.3 (6H, m), 7.8–8.0 (4H, m), 8.14 (1H, d), 9.95 (1H, s), 9.98 (1H, s)

Reference Example 28

2,6-Bis(4-formylphenoxy)benzonitrile

Mass spectrometry data (m/z): 342 ([M−H]$^−$)

Nuclear magnetic resonance spectrum (CDCl$_3$, TMS internal standard)

δ: 6.81 (2H, d), 7.25 (4H, d), 7.52 (1H, t), 7.96 (4H, d), 10.00 (2H, s)

Reference Example 29

2,4-Bis(4-formylphenoxy)benzonitrile

Mass spectrometry data (m/z): 343 (M$^+$)

Nuclear magnetic resonance spectrum (CDCl$_3$, TMS internal standard)

δ: 6.72 (1H, d), 6.89 (2H, dd), 7.19 (2H, d), 7.21 (2H, d), 7.71 (1H, d), 7.94 (4H, d), 9.96 (2H, s)

Reference Example 30

(a) The following compound was obtained in the same manner as described in Reference Example 22 (a).

1,3-Bis(4-cyanophenoxy)-5-methoxybenzene

Mass spectrometry data (m/z): 342 (M$^+$)

Nuclear magnetic resonance spectrum (CDCl$_3$, TMS internal standard)

δ: 3.78 (3H, s), 6.34 (1H, t), 6.45 (2H, d), 7.06 (4H, d), 7.63 (4H, d)

(b) The following compound was obtained in the same manner as described in Reference Example 22 (b).

1,3-Bis(4-formylphenoxy)-5-methoxybenzene

Mass spectrometry data (m/z): 348 (M$^+$)

Nuclear magnetic resonance spectrum (CDCl$_3$, TMS internal standard)

δ: 3.78 (3H, s), 6.39 (1H, t), 6.48 (2H, d), 7.13 (4H, d), 7.87 (4H, d), 9.94 (2H, s)

Reference Example 31

(a) The following compound was obtained in the same manner as described in Reference Example 22 (a).

1,3-Bis(4-cyanophenoxy)-5-fluorobenzene

Mass spectrometry data (m/z): 330 (M$^+$)

Nuclear magnetic resonance spectrum (CDCl$_3$, TMS internal standard)

δ: 6.54 (2H, m), 6.65 (1H, d), 7.10 (4H, d), 7.67 (4H, d)

(b) The following compound was obtained in the same manner as described in Reference Example 22 (b).

1,3-Bis(4-formylphenoxy)-5-fluorobenzene

Mass spectrometry data (m/z): 337 ([M+H]$^+$)

Nuclear magnetic resonance spectrum (CDCl$_3$, TMS internal standard)

δ: 6.57 (2H, m), 6.67 (1H, d), 7.16 (4H, d), 7.91 (4H, d), 9.96 (2H, s)

Reference Example 32

(a) The following compound was obtained in the same manner as described in Reference Example 22 (a).

1,3-Bis(4-cyanophenoxy)-4-bromobenzene

Mass spectrometry data (m/z): 392 ([M+H]$^+$)

Nuclear magnetic resonance spectrum (CDCl$_3$, TMS internal standard)

δ: 6.8–7.4 (6H, m), 7.6–7.7 (5H, m)

(b) The following compound was obtained in the same manner as described in Reference Example 22 (b).

1,3-Bis(4-formylphenoxy)-4-bromobenzene

Mass spectrometry data (m/z): 396 ([M−H]$^−$)

Nuclear magnetic resonance spectrum (CDCl$_3$, TMS internal standard)

δ: 6.8–7.0 (2H, m), 7.0–7.3 (4H, m), 7.68 (1H, d), 7.8–8.0 (4H, m), 9.94 (2H, s)

Reference Example 33

(a) The following compound was obtained in the same manner as described in Reference Example 22 (a).

3,5-Bis(4-cyanophenoxy)-N,N-dimethylaniline

Mass spectrometry data (m/z): 355 (M$^+$)

Nuclear magnetic resonance spectrum (CDCl$_3$, TMS internal standard)

δ: 2.94 (3H, s), 6.05 (1H, t), 6.23 (2H, d), 7.04 (4H, d), 7.60 (4H, d)

(b) The following compound was obtained in the same manner as described in Reference Example 22 (b).

3,5-Bis(4-formylphenoxy)-N,N-dimethylaniline

Mass spectrometry data (m/z): 361 (M$^+$)

Nuclear magnetic resonance spectrum (CDCl$_3$, TMS internal standard)

δ: 2.95 (3H, s), 6.11 (1H, t), 6.27 (2H, d), 7.10 (4H, d), 7.84 (4H, d), 9.92 (2H, s)

Reference Example 34

(a) The following compound was obtained in the same manner as described in Reference Example 22 (a).

1,3-Bis(4-cyanophenoxy)-4-chlorobenzene

Mass spectrometry data (m/z): 346 (M$^+$)

Nuclear magnetic resonance spectrum (CDCl₃, TMS internal standard)

δ: 6.8–7.2 (6H, m), 7.6–7.8 (5H, m)

(b) The following compound was obtained in the same manner as described in Reference Example 22 (b).

1,3-Bis(4-formylphenoxy)-4-chlorobenzene

Mass spectrometry data (m/z): 352 (M⁺)

Nuclear magnetic resonance spectrum (CDCl₃, TMS internal standard)

δ: 6.9–7.2 (6H, m), 7.52 (1H, d), 7.8–8.0 (4H, m), 9.94 (2H, s)

Reference Example 35

The following compound was obtained by the same treatment as described in Reference Example 22 (a), followed by the same treatment of Reference Example 22 (b) without isolating 1,3-bis(4-cyano-2-fluorophenoxy)benzene.

1,3-Bis(2-fluoro-4-formylphenoxy)benzene

Mass spectrometry data (m/z): 354 (M⁺)

Nuclear magnetic resonance spectrum (CDCl₃, TMS internal standard)

δ: 6.8–6.95 (3H, m), 7.10 (2H, d), 7.39 (1H, t), 7.6–7.8 (4H, d), 9.92 (2H, d)

Reference Example 36

(a) The following compound was obtained in the same manner as described in Reference Example 22 (a).

1,3-Bis(2-chloro-4-cyanophenoxy)benzene

Mass spectrometry data (m/z): 381 (M⁺)

Nuclear magnetic resonance spectrum (CDCl₃, TMS internal standard)

δ: 6.72–6.91 (3H, m), 6.99 (2H, d), 7.5 (1H, m), 7.52 (2H, dd), 7.77 (2H, d)

(b) The following compound was obtained in the same manner as described in Reference Example 22 (b).

1,3-Bis(2-chloro-4-formylphenoxy)benzene

Mass spectrometry data (m/z): 387 (M⁺)

Nuclear magnetic resonance spectrum (CDCl₃, TMS internal standard)

δ: 6.78 (1H, t), 6.90 (2H, dd), 7.06 (2H, d), 7.43 (1H, t), 7.74 (2H, dd), 7.99 (2H, d), 9.91 (2H, s)

Reference Example 37

(a) The following compound was obtained in the same manner as described in Reference Example 22 (a).

1,3-Bis(3-chloro-4-cyanophenoxy)benzene

Mass spectrometry data (m/z): 381 (M⁺)

Nuclear magnetic resonance spectrum (CDCl₃, TMS internal standard)

δ: 6.81 (1H, t), 6.92 (2H, d), 6.97 (2H, dd), 7.10 (2H, d), 7.45 (1H, t), 7.63 (2H, d)

(b) The following compound was obtained in the same manner as described in Reference Example 22 (b).

1,3-Bis(3-chloro-4-formylphenoxy)benzene

Mass spectrometry data (m/z): 387 (M⁺)

Nuclear magnetic resonance spectrum (CDCl₃, TMS internal standard)

δ: 6.7–7.1 (7H, m), 7.47 (1H, t), 7.92 (2H, d), 10.35 (2H, s)

Reference Example 38

(a) The following compound was obtained in the same manner as described in Reference Example 22 (a).

1,3-Bis(4-cyanophenoxy)-4,6-dichlorobenzene

Mass spectrometry data (m/z): 380 (M⁺)

Nuclear magnetic resonance spectrum (DMSO-d₆, TMS internal standard)

δ: 7.20(4H, d, 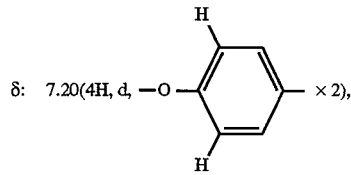 ×2), 7.43(1H, s, 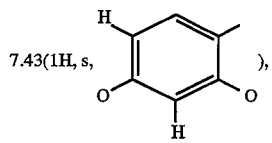 ), 7.85(4H, d, 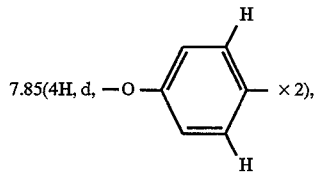 ×2), 8.09(1H, s, 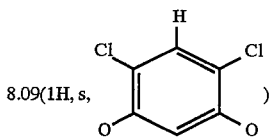 )

(b) The following compound was obtained in the same manner as described in Reference Example 22 (b).

1,3-Bis(formylphenoxy)-4,6-dichlorobenzene

Mass spectrometry data (m/z): 386 (M⁺)

Nuclear magnetic resonance spectrum (DMSO-d₆, TMS internal standard)

δ: 4.20(4H, d, 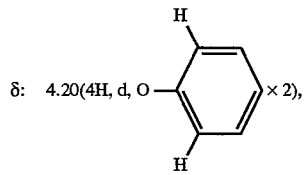 ×2), 7.40(1H, s, 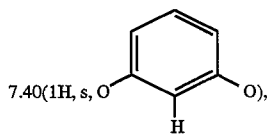 ), 7.93(4H, d, O—⟨⟩—×2), 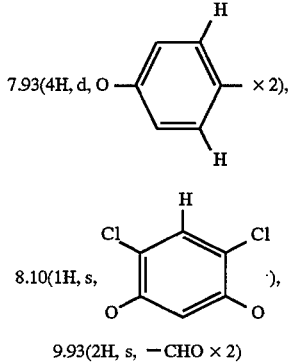

8.10(1H, s, ...), 9.93(2H, s, —CHO × 2)

Reference Example 39

(a) The following compound was obtained in the same manner as described in Reference Example 22 (a).

1,3-Bis(4-cyanophenoxy)-4-ethylbenzene

Mass spectrometry data (m/z): 340 (M⁺)

Nuclear magnetic resonance spectrum (CDCl₃, TMS internal standard)

δ: 1.19 (3H, t, —CH₂C$\underline{H}$₃), 2,58 (2H, q, —C$\underline{H}$₂CH₃), 6.65–7.70 (11H, m, phenyl)

(b) The following compound was obtained in the same manner as described in Reference Example 22 (b).

1,3-Bis(formylphenoxy)-4-ethylbenzene

Mass spectrometry data (m/z): 346 (M⁺)

Nuclear magnetic resonance spectrum (CDCl₃, TMS internal standard)

δ: 1.20 (3H, t, —CH₂C$\underline{H}$₃), 2.61 (2H, q, —C$\underline{H}$₂CH₃), 6.70–8.00 (11H, m, phenyl), 9.91 (2H, s, —CHO×2)

Reference Example 40

(a) The following compound was obtained in the same manner as described in Reference Example 22 (a).

3,5-Bis(4-cyanophenoxy)benzamide

Mass spectrometry data (m/z): 355 (M⁺)

Nuclear magnetic resonance spectrum (DMSO-d₆, TMS internal standard)

δ: 7.14–7.25(1H, 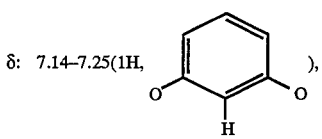), 7.24(4H, d, O—⟨⟩—×2), 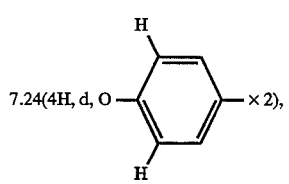

7.49(2H, d, 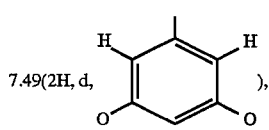), 7.88(4H, d, O—⟨⟩—×2) 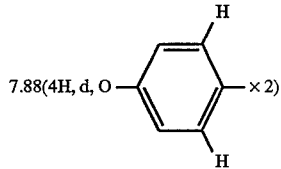

(b) The following compound was obtained in the same manner as described in Reference Example 22 (b).

3,5-Bis(4-formylphenoxy)benzamide

Mass spectrometry data (m/z): 362 ([M+H]⁺)

Nuclear magnetic resonance spectrum (DMSO-d₆, TMS internal standard)

δ: 7.10–7.40(1H, 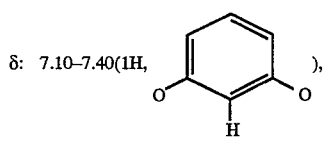), 7.26(4H, d, O—⟨⟩—×2), 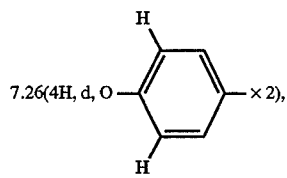

7.50(2H, d, 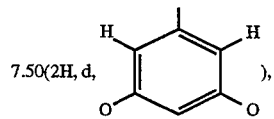), 7.97(4H, d, O—⟨⟩—×2), 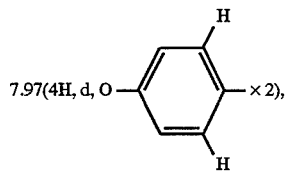

9.96(2H, s, —CHO × 2)

Reference Example 41

At room temperature, 11.4 g of 4-methylaminobenzonitrile dissolved in dimethyl sulfoxide was added dropwise to a mixture of 11.6 g of potassium tert-butoxide and 100 ml of dimethyl sulfoxide. After 20 minutes of stirring, 10.5 g of fluorobenzonitrile was added to the reaction mixture, and the stirring was continued for 30 minutes at room temperature. The whole mixture was poured into water, and the thus formed precipitate was collected by filtration, washed with water and ethanol in that order and then dried to obtain 17.5 g of N,N-bis(4-cyanophenyl)methylamine.

Nuclear magnetic resonance spectrum (CDCl₃, TMS internal standard)

δ: 3.42 (3H, s), 7.10 (4H, d), 7.58 (4H, d)

Reference Example 42

Concentrated hydrochloric acid (45 ml) and ice were added to 21.7 g of 4,4'-thiodianiline to which, with ice-cooling, was subsequently added dropwise 50 ml of aqueous solution of 15.2 g sodium nitrite spending 30 minutes. Five minutes thereafter, the reaction mixture was neutralized with sodium carbonate and added dropwise to 250 ml of ice-cooled water-benzene (3:2) solution containing 22.4 g of copper (I) cyanide and 38.2 g of potassium cyanide. The reaction mixture was stirred for 2 hours while ice-cooling and then mixed with ethyl acetate to remove insoluble materials by filtration. The resulting organic layer was washed with saturated sodium chloride aqueous solution and dried over anhydrous magnesium sulfate. The solvent was evaporated under a reduced pressure, and the resulting residue was subjected to silica gel chromatography and to obtain 11.7 g of bis(4-cyanophenyl) sulfide from fractions of chloroform elution.

Mass spectrometry data (m/z): 236 ($M^+$)

Nuclear magnetic resonance spectrum ($CDCl_3$, TMS internal standard)

δ: 7.39 (4H, d), 7.53 (4H, d)

Example 1

(a) Sodium hydride (2.77 g, 60% oil dispersion) was washed with dry hexane and suspended in 200 ml of dimethylformamide to which was subsequently added 15.6 g of benzyloxyurea in several portions at room temperature. The mixture was stirred for 20 minutes at the internal temperature of 100° C. with heating in an oil bath. After cooling to room temperature, 8.4 g of bis[(4-chloromethyl)phenyl] ether which had been dissolved in 100 ml of dimethylformamide was added dropwise. The reaction mixture was again heated and stirred at the internal temperature of 100° C. for 30 minutes, ice-cooled, and then mixed with 100 ml of 1N hydrochloric acid. The mixture was extracted with ethyl acetate, and the resulting organic layer was washed with water and saturated sodium chloride aqueous solution in that order and dried over anhydrous magnesium sulfate. The solvent was evaporated to obtain 15.4 g of crude crystals. By recrystallizing from 30 ml of ethanol, 8.5 g of bis[[4-(N-carbamoyl-N-benzyloxyamino)methyl]phenyl] ether was obtained.

Mass spectrometry data (m/z): 527 ([M+H]$^+$)

Nuclear magnetic resonance spectrum (DMSO-$d_6$, TMS internal standard)

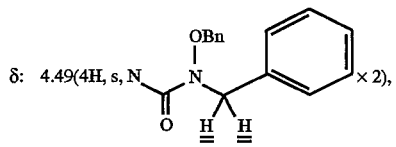

4.74 (4H, s, benzyl), 6.55 (4H, brs, —$NH_2$), 6.90–6.94 (4H, m, phenyl), 7.26–7.28 (4H, m, phenyl), 7.33–7.40 (10H, m, phenyl)

(b) Bis[[4-(N-carbamoyl-N-benzyloxyamino)methyl]phenyl]ether (5 g) was dissolved in 200 ml of ethanol to which was subsequently added 0.5 g of 10% palladium carbon. At room temperature, 9.58 g of ammonium formate was added in several portions. After 2 hours of stirring, the reaction mixture was filtered with Celite, the residue was washed several times with a small volume of dimethylformamide, and then the filtrate and the washed solutions were combined and the solvent was evaporated to effect formation of crude crystals, which were subsequently washed with ethanol to obtain 2.93 g of bis[[4-(N-carbamoyl-N-hydroxyamino)methyl]phenyl]ether.

Mass spectrometry data (m/z): 347 ([M+H]$^+$)

Nuclear magnetic resonance spectrum (DMSO-$d_6$, TMS internal standard)

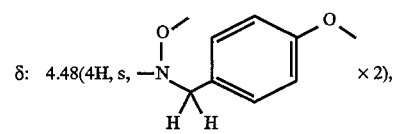

6.35 (4H, s, —$NH_2$×2), 6.93–6.96 (4H, m, phenyl), 7.27–7.30 (4H, m, phenyl), 9.30–9.40 (2H, brs, N—OH)

(c) Bis[[4-(N-carbamoyl-N-hydroxyamino)methyl]phenyl]ether (2.93 g) was suspended in 100 ml of tetrahydrofuran, and 25 ml of 2N sodium hydroxide aqueous solution was slowly added to the suspension with ice-cooling. When it became a uniform solution, 2.75 g of ethyl chloroformate was added dropwise, and the mixture was stirred at room temperature for 13 hours. After adding 9 ml of 6N hydrochloric acid with ice-cooling, the reaction solution was extracted with ethyl acetate (200 ml×3), and the organic layer was washed with water and saturated sodium chloride aqueous solution in that order and dried over anhydrous magnesium sulfate. The solvent was evaporated to obtain 2.77 g of crude crystals. They were recrystallized from a mixed solvent of 30 ml ethanol and 5 ml dioxane to obtain 1.63 g of bis-[4-[(3,5-dioxo-1,2,4-oxadiazolidin-2-yl)methyl]phenyl]ether Melting point: 175°–178° C.

Elemental analysis (for $C_{18}H_{14}N_4O_7$)

|       | C (%) | H (%) | N (%) |
|-------|-------|-------|-------|
| calcd. | 54.28 | 3.54  | 14.07 |
| found  | 53.96 | 3.69  | 13.59 |

Mass spectrometry data (m/z): 397 ([M−H]$^−$)

Nuclear magnetic resonance spectrum. (DMSO-$d_6$, TMS internal standard)

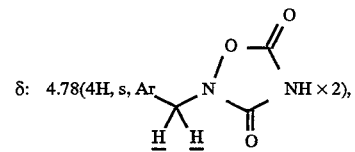

7.03–7.05(4H, m, phenyl), 7.63–7.38(4H, m, phenyl),

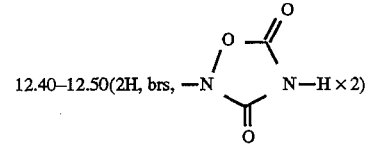

The following compounds of Examples 2 to 8 were synthesized in the same manner as in Example 1.

Example 2

(a) Bis[4-[[(N-benzyloxy-N-carbamoyl)amino]methyl]phenyl]methane (b) Bis[4-[[(N-carbamoyl-N-hydroxy)amino]methyl]phenyl]methane Mass spectrometry data (m/z): 345 ([M+H]$^+$)

Nuclear magnetic resonance spectrum (DMSO-$d_6$, TMS internal standard)

δ: 3.88(2H, s, 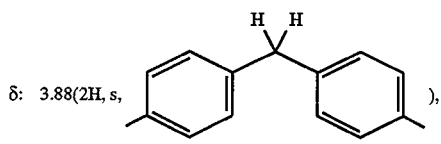), 4.45(4H, s, 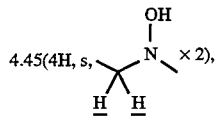), 6.30(4H, s, —NH₂ × 2), 7.18(8H, s, phenyl), 9,27(2H, s, —O$\underline{H}$ × 2)

(c) Bis[4-[(3,5-dioxo-1,2,4-oxadiazolidin-2-yl)methyl]phenyl]methane

Melting point: 179°–180° C.

Elemental analysis (for $C_{19}H_{16}N_4O_6$)

|  | C (%) | H (%) | N (%) |
|---|---|---|---|
| calcd. | 57.58 | 4.07 | 14.14 |
| found | 57.11 | 4.09 | 13.08 |

Mass spectrometry data (m/z): 395 ([M–H]⁻)

Nuclear magnetic resonance spectrum (DMSO, TMS internal standard)

δ: 3.94(24H, s, 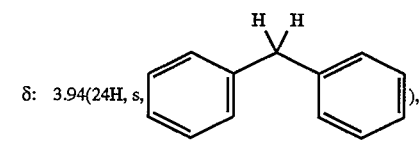), 4.74(4H, s, 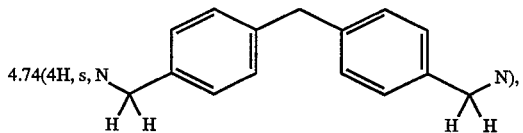), 7.23–7.27(8H, m), 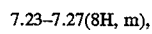

12,4–12.45(2H, brs, 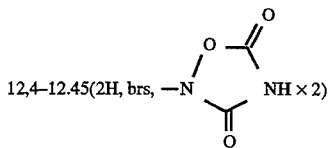)

Example 3

(a) 2,7-Bis[4-[[(N-benzyloxy-N-carbamoyl)amino]methyl]phenoxy]naphthalene

Melting point: 109°–113° C.

Mass spectrometry data (m/z): 669 ([M+H]⁺)

Nuclear magnetic resonance spectrum (DMSO-d₆, TMS internal standard)

δ: 4.52(4H, s, 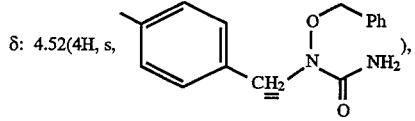), 4.76(4H, s, 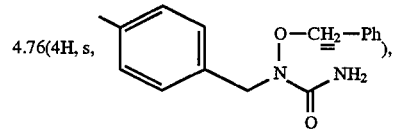), 6.57(4H, s, 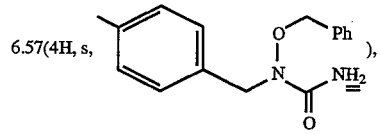), 7.01(4H, d, J=8.8Hz, 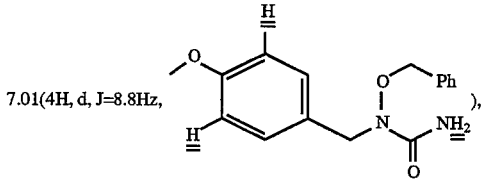), 7.17(2H, dd, J=2.4 and 8.8Hz, 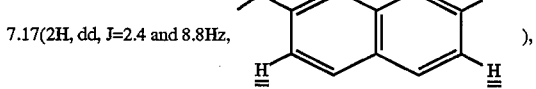), 7.25(2H, d, J=2.4Hz, 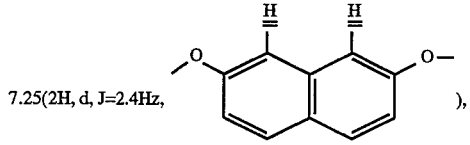), 7.28–7.45(14H, m, phenyl and 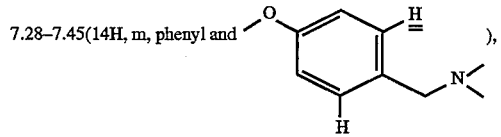), 7.94(2H, d, J=8.8Hz, 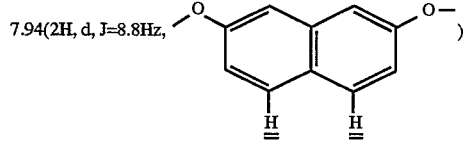)

(b) 2,7-Bis[4-[[(N-carbamoyl-N-hydroxy)amino]methyl]phenoxy]naphthalene

Melting point: 188°–192° C.

Mass spectrometry data (m/z): 489 ([M+H]⁺)

Nuclear magnetic resonance spectrum (DMSO-d₆, TMS internal standard)

δ: 4.51(4H, s, 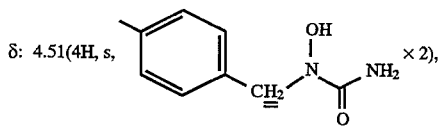),

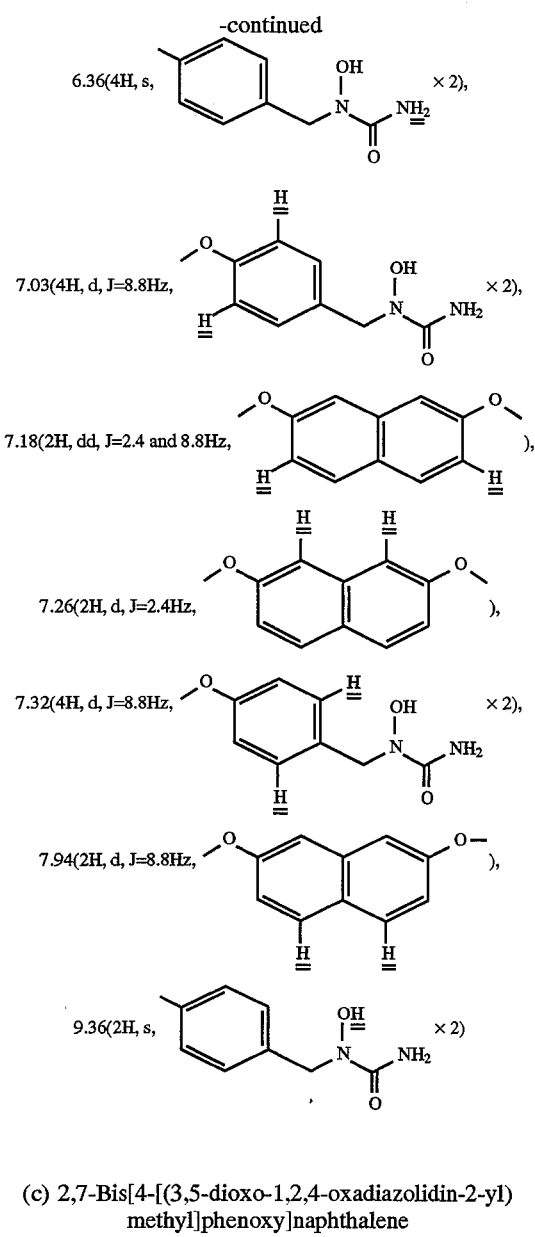

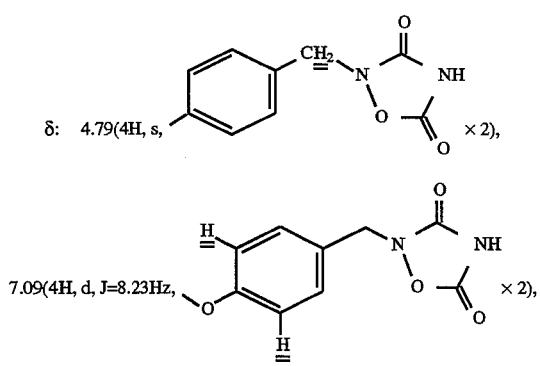

(c) 2,7-Bis[4-[(3,5-dioxo-1,2,4-oxadiazolidin-2-yl)methyl]phenoxy]naphthalene

Melting point: 174°–176° C.

Mass spectrometry data (m/z): 539 ([M–H]⁻)

Nuclear magnetic resonance spectrum (DMSO-d₆, TMS internal standard)

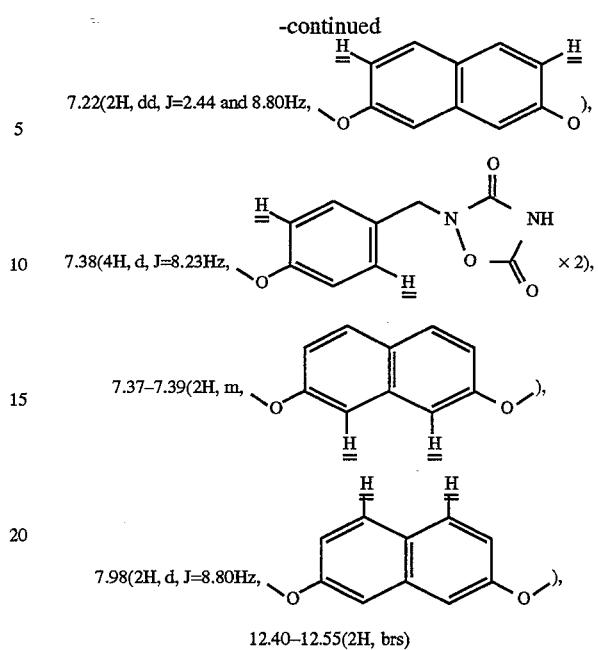

Example 4

(a) 1,4-Bis[4-[[(N-benzyloxy-N-carbamoyl)amino]methyl]phenoxy]benzene

Melting point: 118°–122° C.

Mass spectrometry data (m/z): 619 ([M+H]⁺)

Nuclear magnetic resonance spectrum (DMSO-d₆, TMS internal standard)

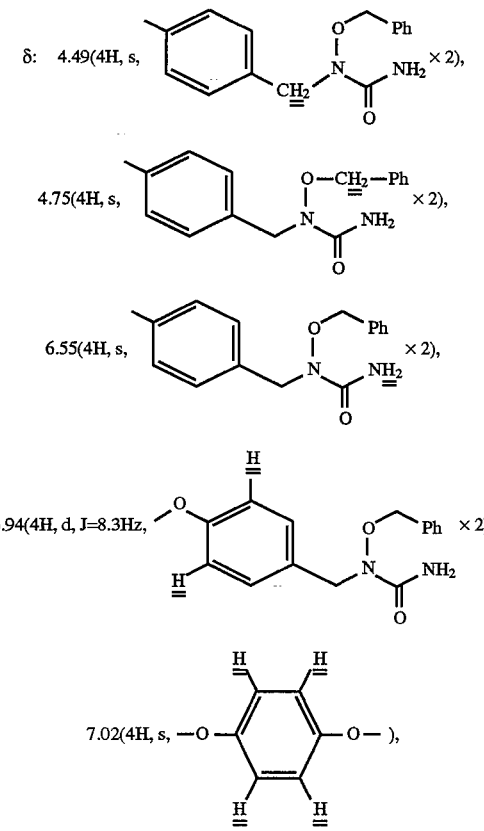

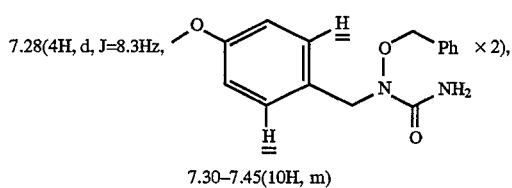

(b) 2,7-Bis[4-[[(N-carbamoyl-N-hydroxy)amino]methyl]phenoxy]benzene

Mass spectrometry data (m/z): 439 ([M+H]⁺)

Nuclear magnetic resonance spectrum (DMSO-d$_6$, TMS internal standard)

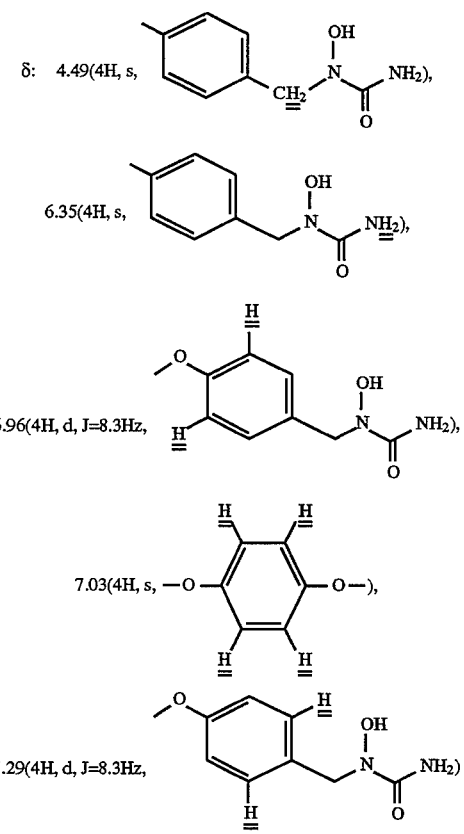

(c) 1,4-Bis[4-[(3,5-dioxo-1,2,4-oxadiazolidin-2-yl)methyl]phenoxy]benzene

Mass spectrometry data (m/z): 489 ([M−H]⁻)

Nuclear magnetic resonance spectrum (DMSO-d$_6$, TMS internal standard)

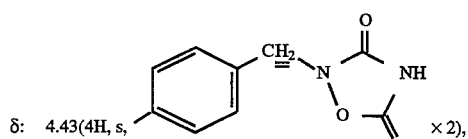

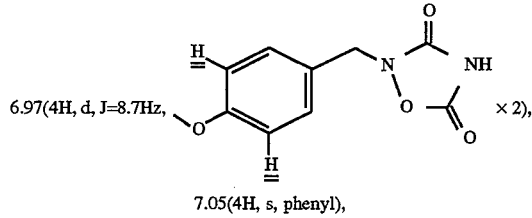

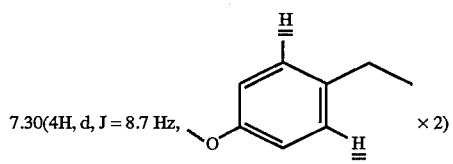

Example 5

(a) 1,5-Bis[4-[[(N-benzyloxy-N-carbamoyl)amino]methyl]phenoxy]pentane

Mass spectrometry data (m/z): 613 ([M+H]⁺)

Nuclear magnetic resonance spectrum (DMSO-d$_6$, TMS internal standard)

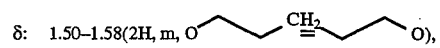

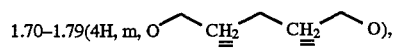

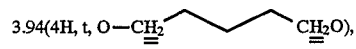

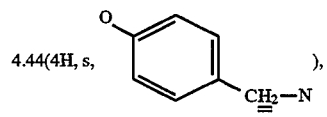

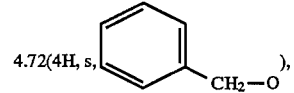

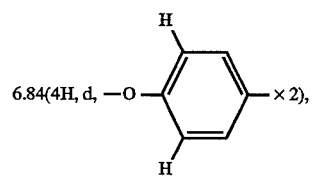

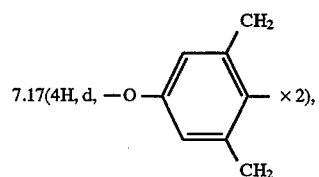

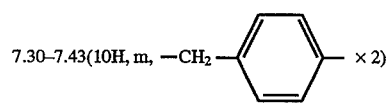

(b) 1,5-Bis[4-[[(N-carbamoyl-N-hydroxy)amino]methyl]phenoxy]pentane

Mass spectrometry data (m/z): 433 ([M+H]⁺)

Nuclear magnetic resonance spectrum (DMSO-d$_6$, TMS internal standard)

δ: 1.45–1.90(6H, m, 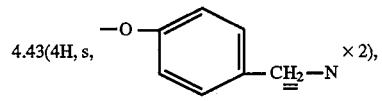

3.97(4H, t, 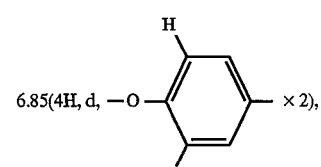

4.43(4H, s, 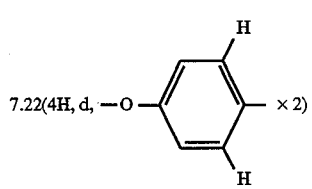

6.85(4H, d, ─O─⟨⟩─ ×2), 7.22(4H, d, ─O─⟨⟩─ ×2)

(c) 1,5-Bis[4-[(3,5-dioxo-1,2,4-oxadiazolidin-2-yl)methyl]phenoxy]pentane

Starting compound: 1,5-bis[4-[(N-carbamoyl-N-hydroxy)amino]methylphenoxy]pentane Melting point: 156°–7° C.

Elemental analysis (for $C_{23}H_{24}N_4O_8$)

|       | C (%) | H (%) | N (%) |
|-------|-------|-------|-------|
| calcd. | 57.02 | 4.99  | 11.56 |
| found  | 56.82 | 4.94  | 11.62 |

Mass spectrometry data (m/z): 483 ([M−H]⁻)

Nuclear magnetic resonance spectrum (DMSO-d₆, TMS internal standard)

δ: 1.53–1.60(2H, m, O∼CH₂∼O), 1.73–1.81(4H, m, O∼CH₂∼CH₂∼O), 3.99(4H, t, O─CH₂∼CH₂O), 4.71(4H, s, 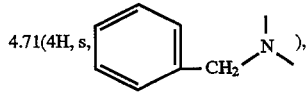

6.93(4H, d, phenyl), 7.24(4H, d, phenyl)

Example 6

(a) 1,3-Bis[4-[[(N-benzyloxy-N-carbamoyl)amino]methyl]phenoxy]benzene

Mass spectrometry data (m/z): 619 ([M+H]⁺)

Nuclear magnetic resonance spectrum (CDCl₃, TMS internal standard)

δ: 4.60(4H, s, 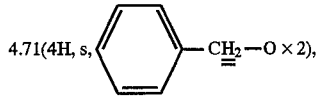

4.71(4H, s, ⟨⟩─CH₂─O ×2), 6.60–7.42(18H, m, phenyl)

(b) 1,3-Bis[4-[[(N-carbamoyl-N-hydroxy)amino]ethyl]phenoxy]benzene (c) 1,3-Bis[4-[(3,5-dioxo-1,2,4-oxadiazolidin-2-yl)methyl]phenoxy]benzene Starting compound: 1,3-Bis[4-[(N-carbamoyl-N-hydroxyl)aminomethyl]phenoxy]benzene Melting point: 174°–5° C.

Elemental analysis (for $C_{24}H_{18}N_4O_8$)

|       | C (%) | H (%) | N (%) |
|-------|-------|-------|-------|
| calcd. | 58.78 | 3.70  | 11.42 |
| found  | 58.69 | 3.73  | 11.13 |

Mass spectrometry data (m/z): 489 ([M−H]⁻)

Nuclear magnetic resonance spectrum (DMSO-d₆, TMS internal standard)

δ: 4.78(4H, s, ⟨⟩─CH₂─N), 6.50–7.42(4H, m, 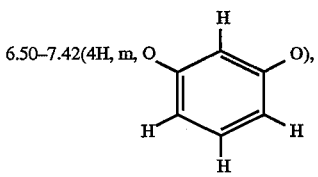

7.07(4H, d, phenyl), 7.37(4H, d, phenyl)

Example 7

(a) Trans-1,4-bis[[4-[[(N-benzyloxy-N-carbamoyl)amino]methyl]phenoxy]methyl]cyclohexane Mass spectrometry data (m/z): 653 ([M+H]⁺)

Nuclear magnetic resonance spectrum (DMSO-d₆, TMS internal standard)

δ: 1.00–1.90 (10H, m, ─⟨⟩─), 3.75(4H, d, 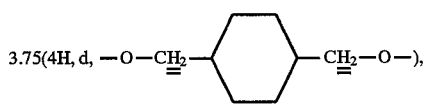

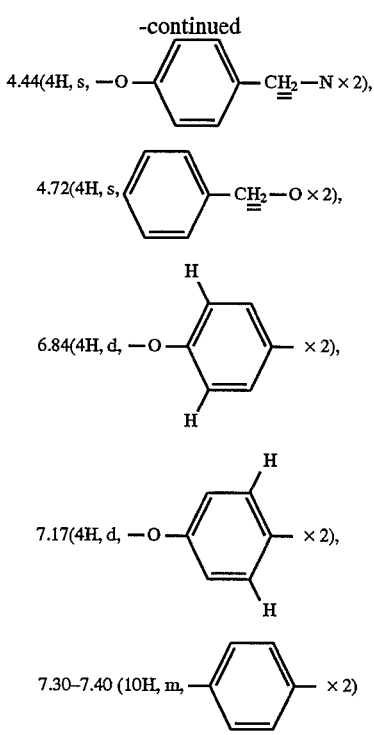

(b) Trans-1,4-bis[[4-[[(N-carbamoyl-N-hydroxy) amino]methyl]phenoxy]methyl]cyclohexane Mass spectrometry data (m/z): 473 ([M+H]⁺)

Nuclear magnetic resonance spectrum (DMSO-$d_6$, TMS internal standard)

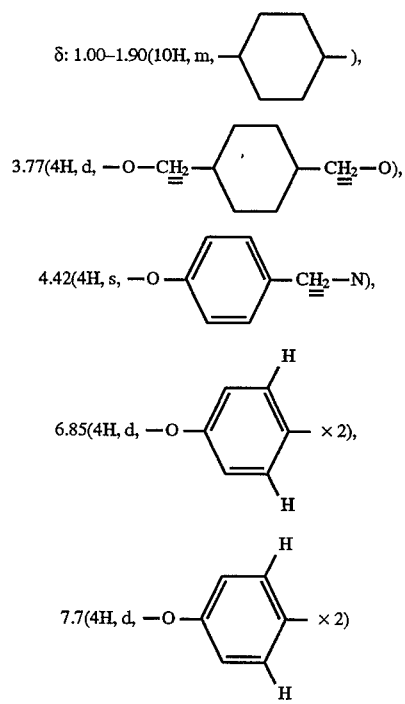

(c) Trans-1,4-bis[[4-[(3,5-dioxo-1,2,4-oxadiazolidin-2-yl)methyl]phenoxy]methyl]cyclohexane Starting compound: trans-1,4-bis[[4-[(N-carbamoyl-N-hydroxy)aminomethyl]phenoxy]methyl]cyclohexane Melting point: 175°–6° C.

Elemental analysis (for $C_{26}H_{28}N_4O_8$)

|  | C (%) | H (%) | N (%) |
|---|---|---|---|
| calcd. | 59.54 | 5.38 | 10.68 |
| found | 59.67 | 5.48 | 10.07 |

Mass spectrometry data (m/z): 523 ([M−H]⁻)

Nuclear magnetic resonance spectrum (DMSO-$d_6$, TMS internal standard)

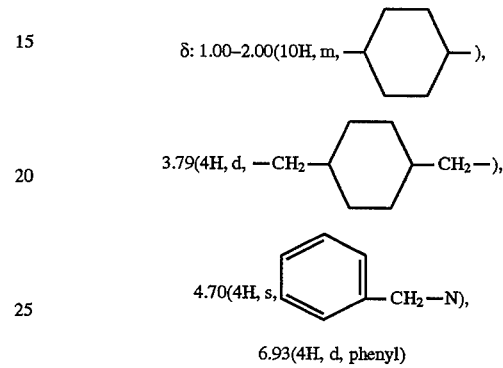

Example 8

(a) Cis-1,3-bis[4-[[(N-benzyloxy-N-carbamoyl) amino]methyl]phenoxy]cyclohexane (b) Cis-1,3-bis[4-[[(N-carbamoyl-N-hydroxy)amino] methyl]phenoxy]cyclohexane (c) Cis-1,3-bis[4-[(3,5-dioxo-1,2,4-oxadiazolidin-2-yl)methyl]phenoxy]cyclohexane Starting compound: cis-1,3-bis[4-[(N-carbamoyl-N-hydroxy)aminomethyl]phenoxy]cyclohexane Amorphous Mass spectrometry data (m/z): 495 ([M−H]⁻)

Nuclear magnetic resonance spectrum (DMSO-$d_6$, TMS internal standard)

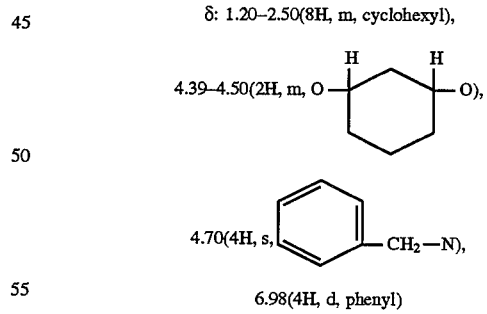

Example 9

(a) 1,2-Bis[4-[[(N-benzyloxy-N-carbamoyl)amino] methyl]phenoxy]benzene (b) 1,2-Bis[4-[[(N-carbamoyl-N-hydroxy)amino] methyl]phenoxy]benzene (c) 1,2-Bis[4-[(3,5-dioxo-1,2,4-oxadiazolidin-2-yl) methyl]phenoxy]benzene Melting point: 105°–112° C.

Elemental analysis (for $C_{24}H_{18}N_4O_8 \cdot 1.4H_2O$)

|        | C (%) | H (%) | N (%) |
|--------|-------|-------|-------|
| calcd. | 55.90 | 4.07  | 10.87 |
| found  | 56.14 | 3.95  | 10.53 |

Mass spectrometry data (m/z): 487 ([M−H]⁻)

Nuclear magnetic resonance spectrum (DMSO-d₆, TMS internal standard)

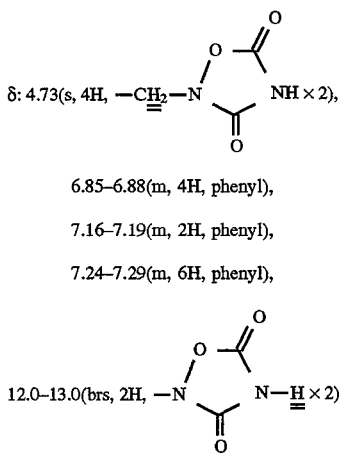

δ: 4.73(s, 4H, −CH₂−N(...)NH×2), 6.85–6.88(m, 4H, phenyl), 7.16–7.19(m, 2H, phenyl), 7.24–7.29(m, 6H, phenyl), 12.0–13.0(brs, 2H, −N(...)N−H×2)

Example 10

(a) The mixture of (Z)-1,4bis(4-formylphenoxy)-2-butene (9.85 g), hydroxylamine, hydrochloride (6.91 g) and sodium acetate (8.20 g) in water methanol (12:88) (225 ml) was subjected to 0.5 hour of heating under reflux, the solvent was evaporated under a reduced pressure and then the thus obtained residue was diluted with water and extracted with ethyl acetate. The organic layer was washed with saturated sodium chloride aqueous solution and dried over anhydrous magnesium sulfate. The solvent was evaporated under a reduced pressure to obtain the crude product of (Z)-1,4-bis[4-(N-hydroxyiminomethyl)phenoxy]-2-butene (10.4 g). The thus obtained crude product (1.74 g) was dissolved in ethanol-tetrahydrofuran (1:2) (60 ml) and, with ice-cooling, to the solution was added borane-pyridine complex (1.1 ml) and the mixture was stirred for 1.25 hours. 10% Hydrochloric acid (12 ml) was added dropwise to the reaction mixture, and the mixture was subsequently stirred for 0.5 hour with ice-cooling and 4.5 hours at room temperature and then mixed with saturated potassium carbonate aqueous solution. The solvent was evaporated under a reduced pressure, and the thus obtained residue was diluted with water and extracted with chloroform. The organic layer was washed with saturated sodium chloride aqueous solution and dried over anhydrous magnesium sulfate, and the solvent was subsequently evaporated under a reduced pressure. The resulting residue was purified by silica gel column chromatography with chloroform-methanol (50:1) elution to obtain (Z)-1,4-bis[4-(N-hydroxyaminomethyl)phenoxy]-2-butene (0.86 g).

Nuclear magnetic resonance spectrum (DMSO-d₆, TMS internal standard)

δ: 3.79 (4H, s), 4.69 (4H, d), 5.8–5.9 (4H, m), 6.88 (4H, d), 7.24 (4H, d)

(b) Concentrated hydrochloric acid (1 ml) was added dropwise to the solution of (Z)-1,4-Bis[4-(N-hydroxyaminomethyl)phenoxy]-2-butene (0.86 g) in methanol-tetrahydrofuran (1:1) (40 ml), 1N potassium cyanate aqueous solution (7.5 ml) was added to the mixture, followed by stirring at room temperature for 1.25 hours. The solvent was evaporated under a reduced pressure, and the thus obtained residue was adjusted to pH 10 by adding 1N sodium hydroxide aqueous solution and extracted with ethyl acetate. The organic layer was washed with saturated sodium chloride aqueous solution and dried over anhydrous magnesium sulfate, and then the solvent was evaporated under a reduced pressure to obtain the crude product of (Z)-1,9-bis[4-[(1-hydroxyureido)methyl]phenoxy]-2-butene (1.02 g).

(c) To the solution of (Z)-1,4-Bis[4-[(1-hydroxyureido) methyl]phenoxy]-2-butene (0.75 g) in tetrahydrofuran (20 ml) was added 2N sodium hydroxide aqueous solution (6.9 ml) and then, with ice-cooling, ethyl chloroformate (0.66 ml) was added dropwise to the mixture. After 49 hours of stirring at room temperature, the reaction mixture was adjusted to pH 1 with 6N hydrochloric acid and extracted with ethyl acetate. The organic layer was washed with saturated sodium chloride aqueous solution and dried over anhydrous magnesium sulfate and then the solvent was evaporated under a reduced pressure. The resulting residue was subjected to silica gel column chromatography with chloroform-methanol (10:1) elution, and the obtained crude product was recrystallized from methanol to obtain (Z)-1,4-bis[4-[(3,5-dioxo-1,2,4-oxadiazolidin-2-yl)methyl]phenoxy]-2-butene (0.31 g).

Product of (b)

Mass spectrometry data (m/z): 417 ([M+H]⁺)

Nuclear magnetic resonance spectrum (DMSO-d₆, TMS internal standard) δ: 4.43 (4H, s), 4.70 (4H, d), 5.87 (2H, t), 6.52 (4H, s), 6.89 (4H, d), 7.20 (4H, d), 9.24 (2H, s)

Product of (c)

Melting point: 139°–144° C.

Elemental analysis (for $C_{22}H_{20}N_4O_8$)

|        | C (%) | H (%) | N (%) |
|--------|-------|-------|-------|
| calcd. | 56.41 | 4.30  | 11.96 |
| found  | 56.25 | 4.24  | 11.85 |

Mass spectrometry data (m/z):467 ([M−H]⁻)

Nuclear magnetic resonance spectrum (DMSO-d₆, TMS internal standard) δ: 4.73 (4H, d), 5.87 (2H, t), 6.98 (4H, d), 7.26 (4H, d), 12.42 (2H, brs)

Example 11

(a) The following compound was obtained in the same manner as described in Example 10 (a).

1,9-Bis[4-(hydroxyaminomethyl)phenoxy]nonane

Starting compound: 1,9-bis(formylphenoxy)nonene

Mass spectrometry data (m/z): 403 ([M+H]⁺)

Nuclear magnetic resonance spectrum (DMSO-d₆, TMS internal standard) δ: 1.25–1.45 (10H, m), 1.65–1.75 (4H, m), 3.33 (2H, s), 3.77 (4H, s), 3.92 (4H, t), 6.85 (4H, d), 7.29 (4H, d)

(b) 1,9-Bis[4-(hydroxyaminomethyl)phenoxy]nonane (1.07 g) was dissolved in 75 ml of tetrahydrofuran-dimethylformamide (4:1) and, in an atmosphere of argon and with ice-cooling, 0.75 ml of ethoxycarbonyl isocyanate was added dropwise to the solution. After 10 minutes of stirring, 1N sodium hydroxide aqueous solution was added dropwise to the reaction mixture with water-cooling, followed by 2 hours of stirring at room temperature. The solvent was evaporated under a reduced pressure, and the thus obtained residue was mixed with 1N hydrochloric acid and the mixture was extracted with ethyl acetate. The organic layer was washed with water and saturated sodium chloride aqueous solution in that order and dried over anhydrous magnesium sulfate. Then, the solvent was evaporated under a reduced pressure. The resulting residue was subjected to silica gel column chromatography, and the thus obtained 0.78 g of crude product obtained from fractions of chloroform-methanol (40:1) elution was recrystallized from methanol to obtain 0.69 g of 1,9-bis[4-[(3,5-dioxo-1,2,4-oxadiazolidin-2-yl)methyl]phenoxy]nonane.

Melting point: 149°–151° C.

Elemental analysis (for $C_{27}H_{32}N_4O_8$)

|  | C (%) | H (%) | N (%) |
|---|---|---|---|
| calcd. | 59.99 | 5.97 | 10.36 |
| found | 60.00 | 5.98 | 10.36 |

Mass spectrometry data (m/z): 541 ([M+H]$^+$)

Nuclear magnetic resonance spectrum (DMSO-$d_6$, TMS internal standard) δ: 1.25–1.45 (14H, m), 3.95 (4H, t), 4.70 (9H, s), 6.92 (4H, d), 7.23 (4H, d), 12.42 (2H, brs)

Example 12

(a) 1,4-Bis(4-formylphenoxy)butane (3.98 g) was dissolved in 10.5 ml of tetrahydrofuran-methanol (5:1), 1.23 g of sodium borohydride was added to the solution which was cooled on ice-water, and the resulting mixture was stirred for 1.5 hours at room temperature. Then, 100 ml of 1N hydrochloric acid was added and the mixture was again stirred at room temperature to collect the thus formed precipitate by filtration. The thus obtained crude product was washed with water and methanol in that order and dried under a reduced pressure to obtain 3.38 g of 1,4-bis(4-hydroxymethylphenoxy)butane.

(b) 1,4-Bis(4-hydroxymethylphenoxy)butane (1.78 g) was added to 25 ml of 4N hydrochloric acid-dioxane solution. The mixture was stirred for 0.5 hour at 65° C., the solvent was evaporated under a reduced pressure. Then, the resulting residue was washed with water and methanol in that order and dried under a reduced pressure to obtain 1.95 g of 1,4-bis(4-chloromethylphenoxy)butane.

Product of (a)

Mass spectrometry data (m/z): 302 (M$^+$)

Nuclear magnetic resonance spectrum (DMSO-$d_6$, TMS internal standard) δ: 3.80–4.20 (4H, m), 4.39 (4H, d), 5.01 (2H, t), 6.87 (4H, d), 7.20 (4H, d)

Product of (b)

Mass spectrometry data (m/z): 338 (M$^+$)

Nuclear magnetic resonance spectrum (CDCl$_3$, TMS internal standard) δ: 1.85–2.15 (4H, m), 3.97–4.10 (4H, m), 4.56 (4H, s), 6.85 (4H, d), 7.29 (4H, d)

(c) 60% Sodium hydride (0.41 g) and 1.71 g of benzyloxyurea were added to 20 ml of dimethylformamide and the mixture was stirred at 80° C. for 7.5 hours. 1,4-Bis(4-chloromethylphenoxy)butane (1.74 g) was added to the reaction mixture at room temperature and the mixture was stirred at 95° C. for 0.5 hour. The reaction product was cooled to room temperature, poured into ice water, mixed with 1N hydrochloric acid and then extracted with ethyl acetate. The organic layer was washed with water and saturated sodium chloride aqueous solution in that order and dried over anhydrous magnesium sulfate and then the solvent was evaporated under a reduced pressure. The resulting crude product was washed with ethyl acetate to obtain 1.94 g of 1,4-bis[4-[(1-benzyloxyureido)methyl]phenoxy]butane.

(d) 1,4-Bis[4-[(1-benzyloxyureido)methyl]phenoxy] butane (1.94 g) was dissolved in 45 ml of dimethylformamide-ethanol (8:1), mixed with 0.29 g of 10% palladium carbon and then the mixture was stirred for 22 hours at room temperature in an atmosphere of hydrogen. The catalyst was removed by filtration using Celite, and the solvent was evaporated under a reduced pressure to obtain 0.84 g of 1,4-bis[4-[(1-hydroxyureido)methyl]phenoxy] butane.

Product of (c)

Mass spectrometry data (m/z): 599 ([M+H]$^+$)

Nuclear magnetic resonance spectrum (DMSO-$d_6$, TMS internal standard) δ: 1.78–1.90 (4H, m), 3.90–4.00 (4H, m), 4.43 (4H, s), 4.72 (4H, s), 6.49 (4H, s), 6.68 (4H, d), 7.18 (4H, d), 7.33–7.39 (10H, m)

Product of (d)

Mass spectrometry data (m/z): 419 ([M+H]$^+$)

Nuclear magnetic resonance spectrum (DMSO-$d_6$, TMS internal standard) δ: 1.78–1.90 (4H, m), 3.95–4.05 (4H, m), 4.43 (4H, s), 6.29 (4H, s), 6.87 (4H, d), 7.18 (4H, d), 9.26 (2H, s)

(e) The following compound was obtained in the same manner as described in Example 10 (c).

1,4-Bis[4-[(3,5-dioxo-1,2,4-oxadiazolidin-2-yl) methyl]phenoxy]butane

Starting compound: 1,4-bis[4-[(1-benzyloxyureido) methyl]phenoxy]butane

Melting point: 188°–192° C.

Mass spectrometry data (m/z): 469 ([M−H]$^-$)

Nuclear magnetic resonance spectrum (DMSO-$d_6$, TMS internal standard) δ: 1.80–1.95 (4H, m), 3.90–4.10 (4H, m), 4.71 (4H, s), 6.94 (4H, d), 7.24 (4H, d), 12.42 (2H, brs)

Example 13

(a) The following compound was obtained in the same manner as described in Example 10 (a).

1,6-Bis[4-(hydroxyaminomethyl)phenoxy]hexane

Mass spectrometry data (m/z): 360 (M$^+$)

Nuclear magnetic resonance spectrum (DMSO-$d_6$, TMS internal standard) δ: 1.20–1.80 (8H, m), 3.65–4.10 (8H, m), 5.85 (2H, t), 6.85 (4H, d), 7.22 (4H, d)

(b) The following compound was obtained in the same manner as described in Example 10 (b).

1,6-Bis[4-[(1-hydroxyureido)methyl]phenoxy] hexane

Mass spectrometry data (m/z): 447 ([M+H]$^+$)

Nuclear magnetic resonance spectrum (DMSO-$d_6$, TMS internal standard) δ: 1.20–2.00 (8H, m), 3.94 (4H, t), 4.43 (4H, s), 6.24 (4H, s), 6.85 (4H, d), 7.18 (4H, d), 9.25 (2H, s)

(c) The following compound was obtained in the same manner as described in Example 10 (c).

1,6-Bis[4-[(3,5-dioxo-1,2,4-oxadiazolidin-2-yl)
methyl]phenoxy]hexane

Melting point: 171°–176° C.

Elemental analysis (for $C_{24}H_{26}N_4O_8$)

|  | C (%) | H (%) | N (%) |
|---|---|---|---|
| calcd. | 57.83 | 5.26 | 11.24 |
| found | 57.52 | 5.23 | 10.96 |

Mass spectrometry data (m/z): 497 ([M+H]$^+$)

Nuclear magnetic resonance spectrum (DMSO-d$_6$, TMS internal standard) δ: 1.40–1.50 (4H, m), 1.65–1.75 (4H, m), 3.97 (4H, t), 4.71 (4H, s), 6.93 (4H, d), 7.24 (4H, d), 12.42 (2H, brs)

Example 14

(a) The following compound was obtained in the same manner as described in Example 10 (a).

(E)-1,4-bis[4-(hydroxyaminomethyl)phenoxy]-2-butene

Mass spectrometry data (m/z): 331 ([M+H]$^+$)

Nuclear magnetic resonance spectrum (DMSO-d$_6$, TMS internal standard) δ: 3.79 (4H, m), 4.57 (4H, s), 5.85 (2H, brs), 6.03–6.05 (2H, m), 6.87 (4H, d), 7.23 (4H, d)

(b) The following compound was obtained in the same manner as described in Example 10 (b).

(E)-1,4-bis[4-[(1-hydroxyureido)methyl]phenoxy]-2-butene

Mass spectrometry data (m/z): 417 ([M+H]$^+$)

Nuclear magnetic resonance spectrum (DMSO-d$_6$, TMS internal standard) δ: 4.44 (4H, m), 4.58 (4H, s), 6.05 (2H, s), 6.31 (4H, s), 6.88 (4H, d), 7.19 (4H, d), 9.68 (2H, brs)

(c) The following compound was obtained in the same manner as described in Example 10 (c).

(E)-1,4-bis[4-[(3,5-dioxo-1,2,4-oxadiazolidin-2-yl)
methyl]phenoxy]-2-butene

Melting point: 184°–189° C.

Elemental analysis (for $C_{22}H_{20}N_4O_8$)

|  | C (%) | H (%) | N (%) |
|---|---|---|---|
| calcd. | 56.41 | 4.30 | 11.96 |
| found | 56.18 | 4.46 | 11.74 |

Mass spectrometry data (m/z): 467 ([M−H]$^-$)

Nuclear magnetic resonance spectrum (DMSO-d$_6$, TMS internal standard) δ: 4.60 (4H, t), 4.71 (4H, s), 6.06 (2H, s), 6.96 (4H, d), 7.26 (4H, d), 12.42 (2H, brs)

Example 15

(a) The following compound was obtained in the same manner as described in Example 10 (a).

1,7-Bis[4-(hydroxyaminomethyl)phenoxy]heptane

Mass spectrometry data (m/z): 374 (M$^+$)

Nuclear magnetic resonance spectrum (DMSO-d$_6$, TMS internal standard) δ: 1.30–1.50 (6H, m), 1.65–1.85 (4H, m), 3.92–3.98 (8H, m), 6.89 (4H, d), 7.30 (4H, d), 9.10 (2H, brs)

(b) The following compound was obtained in the same manner as described in Example 10 (b).

1,7-Bis[4-[(1-hydroxyureido)methyl]phenoxy]heptane

Mass spectrometry data (m/z): 461 ([M+H]$^+$)

Nuclear magnetic resonance spectrum (DMSO-d$_6$, TMS internal standard) δ: 1.30–1.50 (6H, m), 1.65–1.85 (4H, m), 3.95 (4H, t), 4.42 (4H, s), 6.29 (2H, s), 6.86 (4H, d), 7.17 (4H, d), 9.25 (2H, s)

(c) The following compound was obtained in the same manner as described in Example 10 (c).

1,7-Bis[4-[(3,5-dioxo-1,2,4-oxadiazolidin-2-yl)
methyl]phenoxy]heptane

Melting point: 136°–139° C.

Elemental analysis (for $C_{25}H_{28}N_4O_8$)

|  | C (%) | H (%) | N (%) |
|---|---|---|---|
| calcd. | 58.59 | 5.51 | 10.93 |
| found | 58.34 | 5.53 | 10.79 |

Mass spectrometry data (m/z): 511 ([M−H]$^-$)

Nuclear magnetic resonance spectrum (DMSO-d$_6$, TMS internal standard) δ: 1.30–1.50 (6H, m), 1.60–1.85 (4H, m), 3.97 (4H, t), 4.71 (4H, s), 6.92 (4H, d), 7.24 (4H, d), 12.40 (2H, brs)

Example 16

(a) The following compound was obtained in the same manner as described in Example 10 (a).

1,3-Bis[4-(hydroxyaminomethyl)phenoxy]methyl]
benzene

Mass spectrometry data (m/z): 381 ([M+H]$^+$)

Nuclear magnetic resonance spectrum (DMSO-d$_6$, TMS internal standard) δ: 3.78 (4H, s), 5.10 (4H, s), 5.86 (2H, s), 6.95 (4H, d), 7.23 (4H, d), 7.40 (3H, s), 7.52 (1H, s)

(b) The following compound was obtained in the same manner as described in Example 10 (b).

1,3-Bis[[4-[(1-hydroxyureido)methyl]phenoxy]
methyl]benzene

Nuclear magnetic resonance spectrum (DMSO-d$_6$, TMS internal standard) δ: 4.44 (4H, s), 5.12 (4H, s), 6.30 (4H, s), 6.95 (4H, d), 7.20 (4H, d), 7.40 (3H, s), 7.53 (1H, s), 9.51 (2H, brs)

(c) The following compound was obtained in the same manner as described in Example 10 (c).

1,3-Bis[[4-[(3,5-dioxo-1,2,4-oxadiazolidin-2-yl)
methyl]phenoxy]methyl]benzene

Melting point: 189°–193° C.

Elemental analysis (for $C_{26}H_{22}N_4O_8 \cdot 0.5H_2O$)

|       | C (%) | H (%) | N (%) |
|-------|-------|-------|-------|
| calcd. | 59.20 | 4.39 | 10.62 |
| found | 59.16 | 4.29 | 10.47 |

Mass spectrometry data (m/z): 517 ([M–H]⁻)

Nuclear magnetic resonance spectrum (DMSO-$d_6$, TMS internal standard) δ: 4.69 (4H, s), 5.12 (4H, s), 7.01 (4H, d), 7.26 (4H, d), 7.41 (3H, s), 7.54 (1H, s)

Example 17

(a) The following compound was obtained in the same manner as described in Example 10 (a).

1,5-Bis[4-(hydroxyaminomethyl)phenoxy]-3,3-dimethylpentane

Mass spectrometry data (m/z): 375 ([M+H]⁺)

Nuclear magnetic resonance spectrum (CDCl₃, TMS internal standard) δ: 1.04 (6H, s), 1.79 (4H, t), 3.92 (4H, s), 4.02 (4H, t), 6.83 (4H, d), 7.21 (4H, d), 7.26 (2H, s)

(b) The following compound was obtained in the same manner as described in Example 11 (b).

1,5-Bis[4-[(3,5-dioxo-1,2,4-oxadiazolidin-2-yl)methyl]phenoxy]-3,3-dimethylpentane Mass spectrometry data (m/z): 511 ([M–H]⁻)

Nuclear magnetic resonance spectrum (CDCl₃, TMS internal standard) δ: 1.07 (6H, s), 1.81 (4H, t), 4.06 (4H, t), 4.73 (4H, s), 6.81 (4H, d), 7.24 (4H, d)

Example 18

(a) The following compound was obtained in the same manner as described in Example 10 (a).

Cis-1,3-bis[4-(hydroxyaminomethyl)phenoxy]cyclopentane

Mass spectrometry data (m/z): 345 ([M+H]⁺)

Nuclear magnetic resonance spectrum (DMSO-$d_6$, TMS internal standard) δ: 1.75–1.90 (2H, m), 2.05–2.25 (4H, m), 3.32 (4H, s), 3.77 (4H, s), 4.95 (2H, s), 5.84 (2H, brs), 6.84 (4H, d), 7.22 (4H, d)

(b) The following compound was obtained in the same manner as described in Example 11 (b).

Cis-1,3-bis[4-[(3,5-dioxo-1,2,4-oxadiazolidin-2-yl)methyl]phenoxy]cyclopentane

Melting point: 151°–159° C.

Elemental analysis (for $C_{23}H_{22}N_4O_8$)

|       | C (%) | H (%) | N (%) |
|-------|-------|-------|-------|
| calcd. | 57.26 | 4.60 | 11.61 |
| found | 57.35 | 4.70 | 11.30 |

Mass spectrometry data (m/z): 481 ([M–H]⁻)

Nuclear magnetic resonance spectrum (DMSO-$d_6$, TMS internal standard) δ: 1.75–1.90 (2H, m), 2.05–2.30 (4H, m), 4.71 (4H, s), 4.90–5.05 (2H, m), 6.93 (4H, d), 7.24 (2H, brs), 12.42 (2H, brs)

Example 19

(a) The following compound was obtained in the same manner as described in Example 10 (a).

Trans-1,3-bis[4-(hydroxyaminomethyl)phenoxy]cyclopentane

Mass spectrometry data (m/z): 344 (M⁺)

Nuclear magnetic resonance spectrum (DMSO-$d_6$, TMS internal standard) δ: 1.95–2.20 (6H, m), 3.91 (4H, s), 3.95–4.15 (2H, m), 4.70–4.85 (2H, m), 6.82 (4H, d), 7.18 d)

(b) The following compound was obtained in the same manner as described in Example 11 (b).

Trans-1,3-bis[4-[(3,5-dioxo-1,2,4-oxadiazolidin-2-yl)methyl]phenoxy]cyclopentane Mass spectrometry data (m/z): 481 ([M–H]⁻)

Nuclear magnetic resonance spectrum (DMSO-$d_6$, TMS internal standard) δ: 1.74–1.78 (2H, m), 1.80–1.95 (2H, m), 1.95–2.10 (2H, m), 4.30 (4H, s), 4.75–4.85 (2H, m), 6.84 (4H, d), 7.16 (4H, d)

Example 20

(a) The following compound was obtained in the same manner as described in Example 10 (a).

1,8-Bis[4-(hydroxyaminomethyl)phenoxy]octane

Mass spectrometry data (m/z): 389 ([M+H]⁺)

Nuclear magnetic resonance spectrum (DMSO-$d_6$, TMS internal standard) δ: 1.25–1.50 (8H, m), 1.65–1.75 (4H, m), 3.78 (4H, s), 3.92 (4H, t), 6.83 (4H, d), 7.21 (4H, d)

(b) The following compound was obtained in the same manner as described in Example 11 (b).

1,8-Bis[4-[(3,5-dioxo-1,2,4-oxadiazolidin-2-yl)methyl]phenoxy]octane

Melting point: 160°–163° C.

Elemental analysis (for $C_{26}H_{30}N_4O_8$)

|       | C (%) | H (%) | N (%) |
|-------|-------|-------|-------|
| calcd. | 59.31 | 5.74 | 10.64 |
| found | 59.22 | 5.88 | 10.29 |

Mass spectrometry data (m/z): 525 ([M–H]⁻)

Nuclear magnetic resonance spectrum (DMSO-$d_6$, TMS internal standard) δ: 1.25–1.45 (8H, m), 1.65–1.75 (4H, m), 3.95 (4H, t), 4.70 (4H, s), 6.92 (4H, d), 7.24 (4H, d), 12.40 (2H, brs)

Example 21

(a) The following compound was obtained in the same manner as described in Example 10 (a).

2,2-Bis[4-(hydroxyaminomethyl)phenoxy]ethyl ether

Mass spectrometry data (m/z): 349 ([M+H]⁺)

Nuclear magnetic resonance spectrum (DMSO-$d_6$, TMS internal standard) δ: 3.74–3.82 (4H, m), 3.78 (4H, s), 4.07 (4H, t), 5.84 (2H, s), 6.87 (4H, d), 7.23 (4H, d)

(b) The following compound was obtained in the same manner as described in Example 11 (b).

2,2-Bis[4-[(3,5-dioxo-1,2,4-oxadiazolidin-2-yl)methyl]phenoxy]ethyl ether

Melting point: 92°–95° C.

Elemental analysis (for $C_{22}H_{22}N_4O_9$)

|  | C (%) | H (%) | N (%) |
|---|---|---|---|
| calcd. | 54.34 | 4.94 | 10.56 |
| found | 54.05 | 4.91 | 10.51 |

Mass spectrometry data (m/z): 485 ([M−H]⁻)

Nuclear magnetic resonance spectrum (DMSO-$d_6$, TMS internal standard) δ: 3.81 (4H, t), 4.11 (4H, t), 4.71 (4H, s), 6.95 (4H, d), 7.25 (4H, d), 12.45 (2H, brs)

Example 22

(a) The following compound was obtained in the same manner as described in Example 10 (a).

1,2-Bis[4-(hydroxyaminomethyl)phenoxy]ethane

Mass spectrometry data (m/z): 305 ([M+H]⁺)

Nuclear magnetic resonance spectrum (DMSO-$d_6$, TMS internal standard) δ: 3.97 (4H, s), 4.10–4.50 (2H, m), 4.30 (4H, s), 6.95 (4H, d), 7.34 (4H, d)

(b) The following compound was obtained in the same manner as described in Example 11 (b).

1,2-Bis[4-[(3,5-dioxo-1,2,4-oxadiazolidin-2-yl)methyl]phenoxy]ethane

Melting point: 203°–206° C.

Elemental analysis (for $C_{20}H_{18}N_4O_8$)

|  | C (%) | H (%) | N (%) |
|---|---|---|---|
| calcd. | 54.30 | 4.10 | 12.66 |
| found | 54.09 | 4.13 | 12.55 |

Mass spectrometry data (m/z): 441 ([M−H]⁻)

Nuclear magnetic resonance spectrum (DMSO-$d_6$, TMS internal standard) δ: 4.32 (4H, s), 4.72 (4H, s), 6.99 (4H, d), 7.27 (4H, d), 12.42 (2H, brs)

Example 23

(a) The following compound was obtained in the same manner as described in Example 10 (a).

1,3-Bis[4-(hydroxyaminomethyl)phenoxy]propane

Mass spectrometry data (m/z): 319 ([M+H]⁺)

Nuclear magnetic resonance spectrum (DMSO-$d_6$, TMS internal standard) δ: 2.16 (2H, quint), 3.99 (4H, s), 3.90–4.20 (6H, m), 6.91 (4H, d), 7.31 (4H, d)

(b) The following compound was obtained in the same manner as described in Example 11 (b).

1,3-Bis[4-[(3,5-dioxo-1,2,4-oxadiazolidin-2-yl)methyl]phenoxy]propane

Melting point: 176°–178° C.

Elemental analysis (for $C_{21}H_{20}N_4O_8$)

|  | C (%) | H (%) | N (%) |
|---|---|---|---|
| calcd. | 55.26 | 4.42 | 12.28 |
| found | 55.10 | 4.33 | 12.05 |

Mass spectrometry data (m/z): 455 ([M−H]⁻)

Nuclear magnetic resonance spectrum (DMSO-$d_6$, TMS internal standard) δ: 2.16 (2H, quint), 4.13 (4H, t), 4.71 (4H, t), 4.71 (4H, s), 6.96 (4H, d), 7.25 (4H, d), 12.41 (2H, brs)

Example 24

(a) The following compound was obtained in the same manner as described in Example 10 (a).

1,10-Bis[4-(hydroxyaminomethyl)phenoxy]decane

Nuclear magnetic resonance spectrum (DMSO-$d_6$, TMS internal standard) δ: 0.90–1.90 (12H, m), 2.40–2.60 (4H, m), 3.80 (4H, m), 3.60–4.35 (6H, m), 6.83 (4H, s), 6.83 (4H, d), 7.22 (4H, d)

(b) The following compound was obtained in the same manner as described in Example 11 (b).

1,10-Bis[4-[(3,5-dioxo-1,2,4-oxadiazolidin-2-yl)methyl]phenoxy]decane

Melting point: 153°–158° C.

Elemental analysis (for $C_{28}H_{34}N_4O_8$)

|  | C (%) | H (%) | N (%) |
|---|---|---|---|
| calcd. | 60.64 | 6.18 | 10.10 |
| found | 60.55 | 6.22 | 9.59 |

Mass spectrometry data (m/z): 553 ([M−H]⁻)

Nuclear magnetic resonance spectrum (DMSO-$d_6$, TMS internal standard) δ: 1.20–1.40 (12H, m), 1.60–1.75 (4H, m), 3.95 (4H, t), 4.70 (4H, t), 6.92 (4H, d), 7.24 (4H, d), 12.41 (2H, brs)

Example 25

(a) The following compound was obtained in the same manner as described in Example 10 (a).

1,11-Bis[4-(hydroxyaminomethyl)phenoxy]undecane

Nuclear magnetic resonance spectrum (DMSO-$d_6$, TMS internal standard) δ: 0.90–1.90 (14H, m), 2.40–2.65 (4H, m), 3.83 (4H, s), 3.60–4.20 (6H, m), 6.84 (4H, d), 7.23 (4H, d)

(b) The following compound was obtained in the same manner as described in Example 11 (b).

1,11-Bis[4-[(3,5-dioxo-1,2,4-oxadiazolidin-2-yl)methyl]phenoxy]undecane

Melting point: 122°–125° C.

Nuclear magnetic resonance spectrum (DMSO-$d_6$, TMS internal standard) δ: 1.20–1.45 (14H, m), 1.60–1.75 (4H, m), 3.94 (4H, t), 4.69 (4H, s), 6.91 (4H, d), 7.23 (4H, d)

Example 26

(a) The following compound was obtained in the same manner as described in Example 10 (a).

1,12-Bis[4-(hydroxyaminomethyl)phenoxy]dodecane

Mass spectrometry data (m/z): 445 ([M+H]$^+$)

Nuclear magnetic resonance spectrum (DMSO-d$_6$, TMS internal standard) δ: 1.00–1.90 (20H, m), 3.60–4.10 (10H, m), 6.86 (4H, d), 7.27 (4H, d)

(b) The following compound was obtained in the same manner as described in Example 11 (b).

1,12-Bis[4-[(3,5-dioxo-1,2,4-oxadiazolidin-2-yl)methyl]phenoxy]dodecane

Melting point: 220°–228° C.

Mass spectrometry data (m/z): 558 ([M–H]$^-$)

Nuclear magnetic resonance spectrum (DMSO-d$_6$, TMS internal standard) δ: 1.20–1.45 (16H, m), 1.63–1.75 (4H, m), 3.93 (4H, t), 4.52 (4H, s), 6.83 (4H, d), 7.20 (4H, d)

Example 27

(a) The following compound was obtained in the same manner as described in Example 10 (a).

1,5-Bis[4-(hydroxyaminomethyl)phenoxy]-2,2,3,3,4,4-hexafluoropentane

Nuclear magnetic resonance spectrum (DMSO-d$_6$, TMS internal standard) δ: 3.81 (4H, s), 4.72 (4H, t), 5.89 (4H, s), 6.99 (4H, d), 7.28 (4H, d)

(b) The following compound was obtained in the same manner as described in Example 11 (b).

1,5-Bis[4-[(3,5-dioxo-1,2,4-oxadiazolidin-2-yl)methyl]phenyl]-2,2,3,3,4,4-hexafluoropentane Melting point: 128°–131° C.

Mass spectrometry data (m/z): 591 ([M–H]$^-$)

Nuclear magnetic resonance spectrum (DMSO-d$_6$, TMS internal standard) δ: 4.74 (4H, s), 4.78 (4H, t), 7.08 (4H, d), 7.30 (4H, d), 12.44 (2H, brs)

Example 28

(a) Under cooling at –70° C., 24 ml of 1.6M butyllithium-hexane solution was added dropwise to 40 ml of tetrahydrofuran solution containing 6.48 g of 4-bromotoluene. After 1 hour of stirring at –70° C., 20 ml of tetrahydrofuran solution containing 4.33 g of N,N-dimethyl-N',N'-dimethoxyisophthaldiamide were added dropwise to the reaction mixture. After 2 hours of stirring at 70° C. the reaction mixture was diluted with 1N hydrochloric acid and extracted with ethyl acetate. The organic layer was washed with water and saturated sodium chloride aqueous solution and dried over anhydrous magnesium sulfate. The solvent was evaporated under a reduced pressure, and the resulting residue was recrystallized from hexane-ethyl acetate to obtain 3.18 g of 1,3-ditoluoylbenzene.

Mass spectrometry data (m/z): 315 ([M+H]$^+$)

Nuclear magnetic resonance spectrum (DMSO-d$_6$, TMS internal standard) δ: 2.42 (6H, s), 7.39 (4H, d), 7.71 (4H, d), 7.76 (1H, t), 7.95–8.02 (3H, m)

(b) To 60 ml of carbon tetrachloride solution containing 1.82 g of 1,3-ditoluoylbenzene were added 2.27 g of N-bromosuccinimide and 0.15 g of azoisobutyrobenzonitrile. The reaction mixture was heated under reflux for 2 days and then insoluble materials were removed by filtration. The solvent was evaporated under a reduced pressure, and the resulting residue was recrystallized from hexane-ethyl acetate to obtain 1.63 g of 1,3-bis(4-bromomethylbenzoyl)benzene.

Mass spectrometry data (m/z): 471 ([M+H]$^+$)

Nuclear magnetic resonance spectrum (DMSO-d$_6$, TMS internal standard) δ: 4.80 (4H, s), 7.65 (4H, d), 7.76–7.86 (5H, m), 7.99–8.08 (3H, m)

(c) The following compound was obtained in the same manner as described in Example 12 (c).

1,3-Bis[4-[(1-benzyloxyureido)methyl]benzoyl]benzene

Starting compound: 1,3-bis(4-bromomethylbenzoyl)benzene

Mass spectrometry data (m/z): 643 ([M+H]$^+$)

Nuclear magnetic resonance spectrum (CDCl$_3$, TMS internal standard) δ: 4.71–4.72 (4H, m), 4.75–4.77 (4H, m), 7.28–7.49 (14H, m), 7.60–7.74 (5H, m), 7.98–8.18 (3H, m)

(d) Using a hydroxyurea compound obtained in the same manner as described in Example 12 (d), the following compound was obtained in the same manner as Example 10 (c).

1,3-Bis[4-[(3,5-dioxo-1,2,4-oxadiazolidin-2-yl)methyl]benzyl]benzene

Starting compound: 1,3-bis[4-[(1-benzyloxyureido)methyl]benzoyl]benzene

Melting point: 230° C. (decomposition)

Mass spectrometry data (m/z): 485 ([M–H]$^-$)

Nuclear magnetic resonance spectrum (DMSO-d$_6$, TMS internal standard) δ: 3.88 (4H, s), 4.45 (4H, s), 7.01 (2H, d), 7.12–7.21 (10H, m)

Example 29

(a) The following compound was obtained in the same manner as described in Example 12 (c).

1-Benzyloxy-1-(4-nitrobenzyl)urea

Starting compounds: 4-nitrobenzyl bromide, benzyloxyurea

Mass spectrometry data (m/z): 302 ([M+H]$^+$)

Nuclear magnetic resonance spectrum (CDCl$_3$, TMS internal standard) δ: 4.71 (2H, s), 4.76 (2H, s), 5.24 (2H, brs), 7.27–7.40 (5H, m), 7.47 (2H, d), 8.18 (2H, d)

(b) 10% Palladium carbon (0.3 g) was added to 80 ml of ethyl acetate solution containing 4.76 g of 1-benzyloxy-1-(4-nitrobenzyl)urea. The reaction mixture was stirred overnight under normal pressure in an atmosphere of hydrogen, and then insoluble materials were removed by filtration. After evaporating the solvent under a reduced pressure, the resulting residue was purified by silica gel column chromatography (eluant: chloroform:methanol=10:1) to obtain 1.82 g of 1-(4-aminobenzyl)-1-benzyloxyurea.

Mass spectrometry data (m/z): 272 ([M+H]$^+$)

Nuclear magnetic resonance spectrum (CDCl$_3$, TMS internal standard) δ: 4.54 (2H, s), 4.65 (2H, s), 5.19 (2H, brs), 6.65 (2H, d), 7.17 (2H, d), 7.26–7.29 (2H, m), 7.33–7.37 (3H, m)

(c) With ice-cooling, 15 ml of dichloromethane solution containing 0.70 g of isophthalic acid dichloride was added dropwise to 30 ml of dichloromethane solution containing 1.79 g of 1-(4-aminobenzyl)-1-benzyloxyurea and 0.71 g of triethylamine. The reaction mixture was stirred overnight at room temperature and then mixed with 1N hydrochloric acid. The thus formed crystals were collected by filtration, washed with water and dichloromethane and then dried to obtain 1.54 g of N,N'-bis[4-[(1-benzyloxyureido)methyl]phenyl]isophthalic acid amide.

Mass spectrometry data (m/z): 673 ([M+H]$^+$)

Nuclear magnetic resonance spectrum (DMSO-$d_6$, TMS internal standard) δ: 4.51 (4H, s), 4.75 (4H, s), 6.53 (4H, s), 7.27 (4H, d), 7.33–7.42 (10H, m), 7.68 (1H, t), 8.12 (2H, d), 8.51 (1H, s), 10.40 (2H, s)

(d) Ammonium formate (2 g) and 0.3 g of 10% palladium carbon were added to 30 ml of dimethylformamide and 30 ml of ethanol solution containing 1.53 g of N,N'-bis[4-[(1-benzyloxyureido)methyl]phenyl]isophthalic acid amide. The reaction mixture was stirred overnight at room temperature and then insoluble materials were removed by filtration. The solvent was evaporated under a reduced pressure, and water was added to the resulting residue. The thus formed insoluble substance was collected by filtration, washed with water and diethyl ether and then dried to obtain 0.52 g of N,N'-bis[4-[(1-hydroxyureido)methyl]phenyl]isophthalic acid amide.

Mass spectrometry data (m/z): 493 ([M+H]$^+$)

Nuclear magnetic resonance spectrum (DMSO-$d_6$, TMS internal standard) δ: 4.45 (4H, s), 6.35 (4H, s), 7.28 (4H, d), 7.67–7.75 (5H, m), 8.14 (2H, d), 8.53 (1H, s), 9.33 (2H, s), 10.40 (2H, s)

(e) The following compound was obtained in the same manner as described in Example 10 (c).

N,N'-Bis[4-[(3,5-dioxo-1,2,4-oxadiazolidin-2-yl)methyl]phenyl]isophthalic acid amide Starting compound: N,N'-bis[4-[(1-hydroxyureido)methyl]phenyl]isophthalic acid amide Melting point: 300° C. (decomposition)

Mass spectrometry data (m/z): 543 ([M–H]$^-$)

Nuclear magnetic resonance spectrum (DMSO-$d_6$, TMS internal standard) δ: 4.78 (4H, s), 7.35 (4H, d), 7.70 (1H, t), 7.81 (4H, d), 8.14 (2H, d), 8.53 (1H, s), 10.50 (2H, s), 12.44 (2H, s)

Example 30

(a) The following compound was obtained in the same manner as described in Example 12 (c).

1,3-Bis[4-[[1-(4-methoxybenzyloxy)ureido]methyl]benzoyl]benzene

Starting compounds: 1,3-bis(4-bromomethylbenzoyl)benzene, 4-methoxybenzyloxyurea Mass spectrometry data (m/z): 703 ([M+H]$^+$)

Nuclear magnetic resonance spectrum (DMSO-$d_6$, TMS internal standard) δ: 3.73 (6H, s), 4.62 (4H, s), 4.71 (4H, s), 6.58 (4H, s), 6.90 (4H, d), 7.32 (4H, d), 7.43 (4H, d), 7.74–7.75 (5H, m), 7.98–8.02 (3H, m)

b) With ice-cooling, 10 ml of anisole and 40 ml of trifluoroacetic acid were added to 1.47 g of 1,3-bis[4-[[1-(4-methoxybenzyloxy)ureido]methyl]benzoyl]benzene. The reaction mixture was stirred with ice-cooling for 30 minutes and then at room temperature for 6 hours. The solvent was evaporated under a reduced pressure and the resulting residue was mixed with diethyl ether. The thus formed crystals were collected by filtration and dried to obtain 0.79 g of 1,3-bis[4-[(1-hydroxyureido)methyl]benzoyl]benzene.

Mass spectrometry data (m/z): 463 ([M+H]$^+$)

Nuclear magnetic resonance spectrum (DMSO-$d_6$, TMS internal standard) δ: 4.63 (4H, s), 6.44 (4H, s), 7.48 (4H, d), 7.76–7.79 (5H, m), 7.99–8.04 (3H, m), 9.48 (2H, s)

(c) The following compound was obtained in the same manner as described in Example 10 (c).

1,3-Bis[4-[(3,5-dioxo-1,2,4-oxadiazolidin-2-yl)methyl]benzoyl]benzene

Starting compound: 1,3-bis[4-[(1-hydroxyureido)methyl]benzoyl]benzene

Melting point: 183°–185° C.

Mass spectrometry data (m/z): 513 ([M–H]$^-$)

Nuclear magnetic resonance spectrum (DMSO-$d_6$, TMS internal standard) δ: 4.93 (4H, s), 7.56 (4H, d), 7.79 (1H, t), 7.83 (4H, d), 8.01–8.06 (3H, m), 12.52 (2H, s)

Example 31

(a) The following compound was obtained in the same manner as described in Example 10 (a).

1,3-Bis[4-(hydroxyaminomethyl)phenoxy]-4-nitrobenzene

Starting compound: 1,3-bis(4-formylphenoxy)-4-nitrobenzene

Mass spectrometry data (m/z): 398 ([M+H]$^+$)

Nuclear magnetic resonance spectrum (CDCl$_3$, TMS internal standard) δ: 3.82 (4H, br), 6.25 (1H, d), 6.58 (1H, dd), 6.84 (2H, d), 6.86 (2H, d), 7.13 (2H, d), 7.20 (2H, d), 7.89 (1H, d)

(b) The following compound was obtained in the same manner as described in Example 10 (b).

1,3-Bis[4-[(1-hydroxyureido)methyl]phenoxy]-4-nitrobenzene

Starting compound: 1,3-bis[4-(hydroxyaminomethyl)phenoxy]-4-nitrobenzene

Mass spectrometry data (m/z): 484 ([M+H]$^+$)

Nuclear magnetic resonance spectrum (DMSO-$d_6$, TMS internal standard) δ: 4.51 (2H, s), 4.52 (2H, s), 6.38 (4H, s), 6.58 (1H, d), 6.76 (1H, dd), 7.11 (2H, d), 7.12 (2H, d), 7.33 (2H, d), 7.35 (2H, d), 8.14 (1H, d), 9.36 (1H, s), 9.38 (1H, s)

(c) The following compound was obtained in the same manner as described in Example 10 (c).

1,3-Bis[4-[(3,5-dioxo-1,2,4-oxadiazolidin-2-yl)methyl]phenoxy]-4-nitrobenzene

Starting compound: 1,3-bis[4-[(1-hydroxyureido)methyl]phenoxy]-4-nitrobenzene

Melting point: 187°–189° C. (MeOH)

Elemental analysis (for $C_{24}H_{17}N_5O_{10}$)

|  | C (%) | H (%) | N (%) |
| --- | --- | --- | --- |
| calcd. | 53.84 | 3.20 | 13.08 |
| found | 53.83 | 3.26 | 12.95 |

Mass spectrometry data (m/z): 534 ([M–H]°)

Nuclear magnetic resonance spectrum (DMSO-d$_6$, TMS internal standard) δ: 4.79 (2H, s), 4.81 (2H, s), 6.70 (1H, d), 6.85 (1H, dd), 7.12 (2H, d), 7.20 (2H, d), 7.40 (2H, d), 7.43 (2H, d), 8.17 (1H, d)

Example 32

(a) The following compound was obtained in the same manner as described in Example 10 (a).

1,3-Bis[4-(hydroxyaminomethyl)phenoxy]-5-chlorobenzene

Starting compound: 1,3-bis(4-formylphenoxy)-5-chlorobenzene

Mass spectrometry data (m/z): 387 ([M+H]$^+$)

Nuclear magnetic resonance spectrum (DMSO-d$_6$, TMS internal standard) δ: 3.87 (4H, s), 6.52 (1H, t), 6.78 (2H, d), 7.04 (4H, d), 7.40 (4H, d)

(b) The following compound was obtained in the same manner as described in Example 10 (b).

1,3-Bis[4-[(1-hydroxyureido)methyl]phenoxy]-5-chlorobenzene

Starting compound: 1,3-bis[4-(hydroxyaminomethyl)phenoxy]-5-chlorobenzene

Mass spectrometry data (m/z): 473 ([M+H]$^+$)

Nuclear magnetic resonance spectrum (DMSO-d$_6$, TMS internal standard) δ: 4.52 (4H, s), 6.38 (4H, s), 6.35 (1H, t), 6.69 (2H, d), 7.07 (4H, d), 7.34 (4H, d), 9.37 (2H, s)

(c) The following compound was obtained in the same manner as described in Example 10 (c).

1,3-Bis[4-[(3,5-dioxo-1,2,4-oxadiazolidin-2-yl)methyl]phenoxy]-5-chlorobenzene

Starting compound: 1,3-bis[4-[(1-hydroxyureido)methyl]phenoxy]-5-chlorobenzene

Melting point: 84°–86° C., i-Pr$_2$O

Elemental analysis (for $C_{24}H_{17}N_4O_8Cl \cdot H_2O$)

|  | C (%) | H (%) | N (%) | Cl (%) |
|---|---|---|---|---|
| calcd. | 53.10 | 3.53 | 10.32 | 6.53 |
| found | 53.08 | 3.47 | 10.14 | 6.40 |

Mass spectrometry data (m/z): 523 ([M–H]$^-$)

Nuclear magnetic resonance spectrum (DMSO-d$_6$, TMS internal standard) δ: 4.79 (4H, s), 6.61 (1H, t), 6.80 (2H, d), 7.13 (4H, d), 7.40 (4H, d)

Example 33

(a) The following compound was obtained in the same manner as described in Example 10 (a).

2,6-Bis[4-(hydroxyaminomethyl)phenoxy]benzonitrile

Starting compound: 2,6-bis(4-formylphenoxy)benzonitrile

Nuclear magnetic resonance spectrum (DMSO-d$_6$, TMS internal standard) δ: 3.91 (4H, s), 6.56 (2H, d), 7.15 (4H, d), 7.30 (1H, m), 7.46 (4H, d)

(b) The following compound was obtained in the same manner as described in Example 11 (b).

2,6-Bis[4-[(3,5-dioxo-1,2,4-oxadiazolidin-2-yl)methyl]phenoxy]benzonitrile

Starting compound: 2,6-bis[4-(hydroxyaminomethyl)phenoxy]benzonitrile

Melting point: 173°–175° C., EtOH-H$_2$O

Elemental analysis (for $C_{25}H_{17}N_5O_8 \cdot \frac{1}{2}H_2O$)

|  | C (%) | H (%) | N (%) |
|---|---|---|---|
| calcd. | 57.26 | 3.46 | 13.35 |
| found | 57.20 | 3.47 | 13.13 |

Mass spectrometry data (m/z): 514 ([M–H]$^-$)

Nuclear magnetic resonance spectrum (DMSO-d$_6$, TMS internal standard) δ: 4.84 (4H, s), 6.66 (2H, d), 7.25 (4H, d), 7.47 (4H, d), 7.57 (1H, t)

Example 34

The following compound was obtained in the same manner as described in Example 11 (b).

2,4-Bis[4-[(3,5-dioxo-1,2,4-oxadiazolidin-2-yl)methyl]phenoxy]benzonitrile

Starting compound: 2,4-bis[4-(hydroxyaminomethyl)phenoxy]benzonitrile

Melting point: 175°–177° C., EtOH-H$_2$O

Mass spectrometry data (m/z): 514 ([M–H]$^-$)

Nuclear magnetic resonance spectrum (DMSO-d$_6$, TMS internal standard) δ: 4.80 (2H, s), 4.81 (2H, s), 7.53 (1H, s), 6.78 (1H, d), 7.16 (2H, d), 7.20 (2H, d), 7.35 (2H, d), 7.43 (2H, d), 7.89 (1H, d)

Example 35

(a) The following compound was obtained in the same manner as described in Example 10 (a).

1,3-Bis[4-(hydroxyaminomethyl)phenoxy]-5-methoxybenzene

Starting compound: 1,3-bis(4-formylphenoxy)-5-methoxybenzene

Mass spectrometry data (m/z): 348 (M$^+$)

Nuclear magnetic resonance spectrum (CDCl$_3$, TMS internal standard) δ: 3.73 (3H, s), 3.96 (4H, s), 6.29 (3H, m), 7.00 (4H, d), 7.30 (4H, d)

(b) The following compound was obtained in the same manner as described in Example 11 (b).

1,3-Bis[4-[(3,5-dioxo-1,2,4-oxadiazolidin-2-yl)methyl]phenoxy]-5-methoxybenzene

Starting compound: 1,3-bis[4-(hydroxyaminomethyl)phenoxy]-5-methoxybenzene

Amorphous

Mass spectrometry data (m/z): 519 ([M–H]$^-$)

Nuclear magnetic resonance spectrum (CDCl$_3$, TMS internal standard) δ: 3.82 (3H, s), 4.76 (4H, s), 6.18 (1H, s), 6.36 (2H, s), 6.97 (2H, d), 7.29 (2H, d)

Example 36

(a) The following compound was obtained in the same manner as described in Example 10 (a).

1,3-Bis[4-(hydroxyaminomethyl)phenoxy]-5-fluorobenzene

Starting compound: 1,3-bis(4-formylphenoxy)-5-fluorobenzene

Mass spectrometry data (m/z): 371 ([M+H]$^+$)

Nuclear magnetic resonance spectrum (DMSO-d$_6$, TMS internal standard) δ: 3.86 (4H, s), 6.35 (1H, m), 6.44 (1H, d), 6.56 (1H, d), 7.03 (4H, d), 7.39 (4H, d)

(b) The following compound was obtained in the same manner as described in Example 11 (b).

1,3-Bis[4-[(3,5-dioxo-1,2,4-oxadiazolidin-2-yl)methyl]phenoxy]-5-fluorobenzene

Starting compound: 1,3-bis[4-(hydroxyaminomethyl)phenoxy]-5-fluorobenzene

Melting point: 182°–184° C., MeOH

Elemental analysis (for C$_{24}$H$_{17}$N$_4$O$_8$F)

|  | C (%) | H (%) | N (%) | F (%) |
|---|---|---|---|---|
| calcd. | 56.70 | 3.37 | 11.02 | 3.74 |
| found | 56.58 | 3.51 | 10.97 | 3.72 |

Mass spectrometry data (m/z): 507 ([M–H]$^-$)

Nuclear magnetic resonance spectrum (DMSO-d$_6$, TMS internal standard) δ: 4.79 (4H, s), 6.44 (1H, s), 6.62 (2H, d), 7.12 (4H, d), 7.39 (4H, d), 12.45 (2H, brs)

Example 37

The following compound was obtained in the same manner as described in Example 11 (b).

1,3-Bis[4-[(3,5-dioxo-1,2,4-oxadiazolidin-2-yl)methyl]phenoxy]-4-bromobenzene

Starting compound: 1,3-bis[4-(hydroxyaminomethyl)phenoxy]-4-bromobenzene

Amorphous

Mass spectrometry data (m/z): 568 ([M–H]$^-$)

Nuclear magnetic resonance spectrum (DMSO-d$_6$, TMS internal standard) δ: 4.76 (4H, brs), 6.74 (1H, s), 6.79 (1H, dd), 7.00 (2H, d), 7.08 (2H, d), 7.36 (2H, d), 7.36 (2H, d), 7.73 (1H, d)

Example 38

(a) The following compound was obtained in the same manner as described in Example 10 (a).

3,5-Bis[4-(hydroxyaminomethyl)phenoxy]-N,N-dimethylaniline

Starting compound: 3,5-bis(4-formylphenoxy)-N,N-dimethylaniline

Nuclear magnetic resonance spectrum (CDCl$_3$, TMS internal standard) δ: 2.88 (6H, s), 3.90 (4H, s), 5.84 (1H, t), 6.14 (2H, d), 6.93 (4H, d), 7.21 (4H, d)

(b) The following compound was obtained in the same manner as described in Example 11 (b).

3,5-Bis[4-[(3,5-dioxo-1,2,4-oxadiazolidin-2-yl)methyl]phenoxy]-N,N-dimethylaniline Starting compound: 3,5-bis[4-(hydroxyaminomethyl)phenoxy]-N,N-dimethylaniline Amorphous Mass spectrometry data (m/z): 534 ([M+H]$^+$)

Nuclear magnetic resonance spectrum (DMSO-d$_6$, TMS internal standard) δ: 2.84 (6H, s), 4.38 (4H, s), 5.81 (1H, s), 6.11 (2H, s), 6.95 (4H, d), 7.28 (4H, d)

Example 39

(a) The following compound was obtained in the same manner as described in Example 10 (a).

2,6-Bis[4-(hydroxyaminomethyl)phenoxy]pyridine

Starting compound: 2,6-bis(4-formylphenoxy)pyridine

Mass spectrometry data (m/z): 354 ([M+H]$^+$)

Nuclear magnetic resonance spectrum (DMSO-d$_6$, TMS internal standard) δ: 3.86 (4H, s), 6.56 (2H, d), 7.04 (4H, d), 7.35 (4H, d), 7.82 (1H, t)

(b) The following compound was obtained in the same manner as described in Example 11 (b).

2,6-Bis[4-[(3,5-dioxo-1,2,4-oxadiazolidin-2-yl)methyl]phenoxy]pyridine

Starting compound: 2,6-bis[4-(hydroxyaminomethyl)phenoxy]pyridine

Amorphous

Mass spectrometry data (m/z): 490 ([M–H]$^-$)

Nuclear magnetic resonance spectrum (DMSO-d$_6$, TMS internal standard) δ: 4.47 (4H, s), 6.59 (2H, d), 7.08 (4H, d), 7.31 (4H, d), 7.84 (1H, t)

Example 40

(a) The following compound was obtained in the same manner as described in Example 10 (a).

1,3-Bis[4-(hydroxyaminomethyl)phenoxy]-4-chlorobenzene

Starting compound: 1,3-bis(4-formylphenoxy)-4-chlorobenzene

Nuclear magnetic resonance spectrum (CDCl$_3$, TMS internal standard) δ: 3.99 (4H, brs), 6.6–6.8 (2H, m), 6.93 (4H, d-like), 7.22–7.53 (5H, m)

(b) The following compound was obtained in the same manner as described in Example 11 (b).

1,3-Bis[4-[(3,5-dioxo-1,2,4-oxadiazolidin-2-yl)methyl]phenoxy]-4-chlorobenzene

Starting compound: 1,3-bis[4-(hydroxyaminomethyl)phenoxy]-4-chlorobenzene

Amorphous

Mass spectrometry data (m/z): 523 ([M–H]$^-$)

Nuclear magnetic resonance spectrum (DMSO-d$_6$, TMS internal standard) δ: 4.40 (4H, s), 6.72 (1H, d), 6.78 (1H, dd), 6.95 (2H, d), 7.02 (2H, d), 7.31 (2H, d), 7.56 (1H, d)

Example 41

(a) The following compound was obtained in the same manner as described in Example 10 (a).

1,3-Bis[2-fluoro-4-(hydroxyaminomethyl)phenoxy]benzene

Starting compound: 1,3-bis(2-fluoro-4-formylphenoxy)benzene

Mass spectrometry data (m/z): 389 ([M+H]$^+$)

Nuclear magnetic resonance spectrum (DMSO-d$_6$, TMS internal standard) δ: 3.87 (4H, s), 6.54 (1H, s), 6.61 (2H, d), 7.15–7.21 (4H, m), 7.33 (1H, t), 7.36 (2H, d)

(b) The following compound was obtained in the same manner as described in Example 11 (b).

1,3-Bis[4-[(3,5-dioxo-1,2,4-oxadiazolidin-2-yl)
methyl]-2-fluorophenoxy]benzene

Starting compound: 1,3-bis[2-fluoro-4-
(hydroxyaminomethyl)phenoxy]benzene

Melting point: 160°–162° C., CH₃CN-H₂O

Elemental analysis (for $C_{24}H_{16}N_4F_2O_8 \cdot \frac{1}{4}H_2O$)

|  | C (%) | H (%) | N (%) | F (%) |
|---|---|---|---|---|
| calcd. | 54.30 | 3.13 | 10.55 | 7.16 |
| found | 54.49 | 3.30 | 10.34 | 6.89 |

Mass spectrometry data (m/z): 525 ([M–H]⁻)

Nuclear magnetic resonance spectrum (DMSO-d₆, TMS internal standard) δ: 4.81 (4H, s), 6.65 (1H, s), 6.70 (2H, d), 7.21–7.28 (4H, m), 7.33 (1H, t), 7.40 (2H, d)

Example 42

(a) The following compound was obtained in the same manner as described in Example 10 (a).

1,3-Bis[2-chloro-4-(hydroxyaminomethyl)phenoxy]
benzene

Starting compound: 1,3-bis(2-chloro-4-formylphenoxy)benzene

Nuclear magnetic resonance spectrum (CDCl₃, TMS internal standard) δ: 3.96 (4H, s), 6.5–6.8 (3H, m), 7.00 (2H, d), 7.15–7.33 (3H, m), 7.43 (2H, s)

(b) The following compound was obtained in the same manner as described in Example 11 (b).

1,3-Bis[2-chloro-4-[(3,5-dioxo-1,2,4-oxadiazolidin-
2-yl)methyl]phenoxy]benzene

Starting compound: 1,3-bis[2-chloro-4-
(hydroxyaminomethyl)phenoxy]benzene

Amorphous

Mass spectrometry data (m/z): 558 ([M–H]⁻)

Nuclear magnetic resonance spectrum (DMSO-d₆, TMS internal standard) δ: 4.46 (4H, s), 6.58 (1H, t), 6.62 (2H, dd), 7.16 (2H, d), 7.30–7.36 (3H, m), 7.50 (1H, s)

Example 43

(a) The following compound was obtained in the same manner as described in Example 10 (a).

1,3-Bis[3-chloro-4-(hydroxyaminomethyl)phenoxy]
benzene

Starting compound: 1,3-bis(3-chloro-4-formylphenoxy)benzene

Mass spectrometry data (m/z): 421 (M⁺)

Nuclear magnetic resonance spectrum (CDCl₃, TMS internal standard) δ: 4.10 (4H, s), 6.6–7.1 (7H, m), 7.22 (1H, m), 7.34 (2H, d)

(b) The following compound was obtained in the same manner as described in Example 11 (b).

1,3-Bis[3-chloro-4-[(3,5-dioxo-1,2,4-oxadiazolidin-
2-yl)methyl]phenoxy]benzene

Starting compound: 1,3-bis[3-chloro-4-
(hydroxyaminomethyl)phenoxy]benzene

Amorphous

Mass spectrometry data (m/z): 558 ([M–H]⁻)

Nuclear magnetic resonance spectrum (DMSO-d₆, TMS internal standard) δ: 4.49 (4H, d), 6.80 (1H, s), 6.83 (2H, d), 7.06 (2H, dd), 7.16 (2H, d), 7.42 (1H, t), 7.48 (2H, d)

Example 44

(a) The following compound was obtained in the same manner as described in Example 10 (a).

1,3-Bis(4-hydroxyaminomethylphenoxy)-5-
methylbenzene

Starting compound: 1,3-bis(4-formylphenoxy)-5-methylbenzene

Mass spectrometry data (m/z): 366 (M⁺)

Nuclear magnetic resonance spectrum (CDCl₃, TMS internal standard)

δ: 2.24(3H, s, —CH₃),

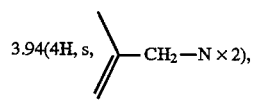
3.94(4H, s, —CH₂—N × 2),

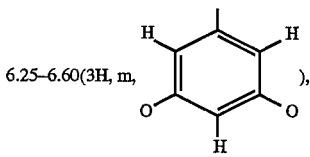
6.25–6.60(3H, m, ),

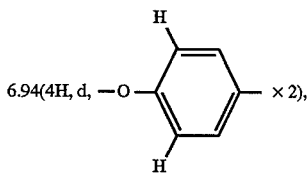
6.94(4H, d, —O— × 2),

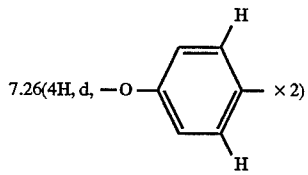
7.26(4H, d, —O— × 2)

(b) The following compound was obtained in the same manner as described in Example 10 (b).

1,3-Bis[4-[(3,5-dioxo-1,2,4-oxadiazolidin-2-yl)
methyl]phenoxy]-5-methylbenzene

Starting compound: 1,3-bis(4-
hydroxyaminomethylphenoxy)-5-methylbenzene

Elemental analysis (for $C_{25}H_{20}N_4O_8$)

|  | C (%) | H (%) | N (%) |
|---|---|---|---|
| calcd. | 59.52 | 4.00 | 11.11 |
| found | 59.42 | 4.00 | 11.06 |

Mass spectrometry data (m/z): 503 ([M–H]⁻)

Nuclear magnetic resonance spectrum (DMSO-d₆, TMS internal standard)

δ: 2.25(3H, s, —CH₃),

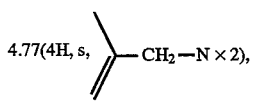  4.77(4H, s,

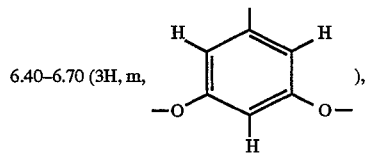  6.40–6.70 (3H, m,

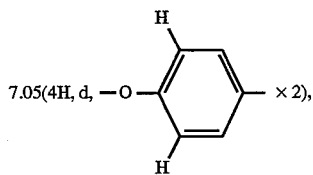  7.05(4H, d,

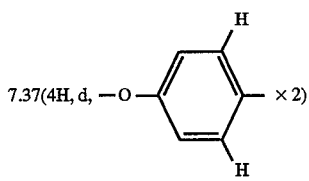  7.37(4H, d,

Example 45

(a) The following compound was obtained in the same manner as described in Example 10 (a).

1,3-Bis(4-hydroxyaminomethylphenoxy)-4,6-dichlorobenzene

Starting compound: 1,3-bis(4-formylphenoxy)-4,6-dichlorobenzene

Mass spectrometry data (m/z): 421 ([M+H]⁺)

Nuclear magnetic resonance spectrum (DMSO-d₆, TMS internal standard)

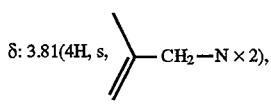  δ: 3.81(4H, s,

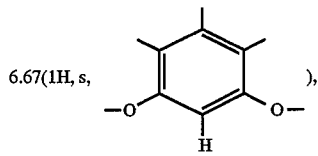  6.67(1H, s,

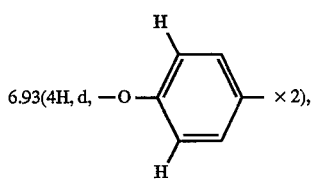  6.93(4H, d,

-continued

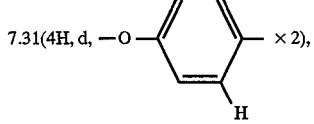  7.31(4H, d,

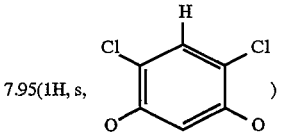  7.95(1H, s, (b) The following compound was obtained in the same manner as described in Example 10 (b).

1,3-Bis[4-[(3,5-dioxo-1,2,4-oxadiazolidin-2-yl)methyl]phenoxy]-4,6-dichlorobenzene Starting compound: 1,3-bis(4-hydroxyaminomethylphenoxy)-4,6-dichlorobenzene Melting point: 217°–8° C.

Mass spectrometry data (m/z): 557 ([M–H]⁻)

Nuclear magnetic resonance spectrum (DMSO-d₆, TMS internal standard)

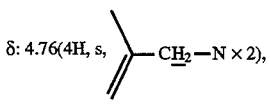  δ: 4.76(4H, s,

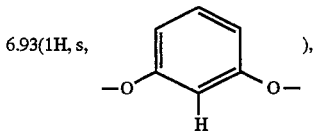  6.93(1H, s,

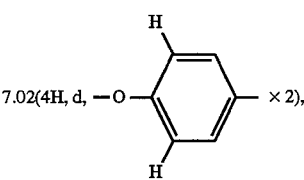  7.02(4H, d,

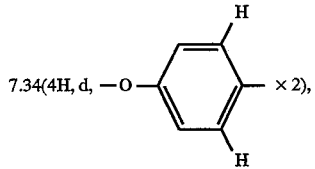  7.34(4H, d,

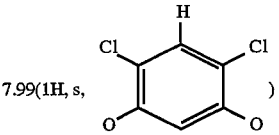  7.99(1H, s,

Example 46

(a) The following compound was obtained in the same manner as described in Example 10 (a).

1,3-Bis(4-hydroxyaminomethylphenoxy)-4-ethylbenzene

Starting compound: 1,3-bis(4-formylphenoxy)-4-ethylbenzene

Mass spectrometry data (m/z): 381 ([M+H]⁺)

Nuclear magnetic resonance spectrum (CDCl₃, TMS internal standard) δ: 1.19 (3H, t, —CH₂C$\underline{H}$₃), 2.62 (2H, q, —C$\underline{H}$₂CH₃),

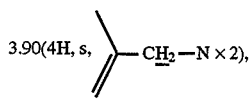

3.90(4H, s, —CH₂—N × 2), 6.25–7.50 (11H, m, phenyl)

(b) The following compound was obtained in the same manner as described in Example 10 (b).

1,3-Bis[4-[(3,5-dioxo-1,2,4-oxadiazolidin-2-yl)methyl]phenoxy]-4-ethylbenzene

Starting compound: 1,3-bis(4-hydroxyaminomethylphenoxy)-4-ethylbenzene

Mass spectrometry data (m/z): 517 ([M−H]⁻)

Nuclear magnetic resonance spectrum (DMSO-d₆, TMS internal standard) δ: 1.13 (3H, t, —CH₂C$\underline{H}$₃), 2.54 (2H, q, —C$\underline{H}$₂CH₃),

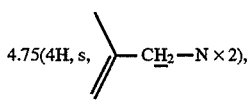

4.75(4H, s, —CH₂—N × 2), 6.50–7.40 (1H, m, phenyl)

Example 47

(a) The following compound was obtained in the same manner as described in Example 10 (a).

3,5-Bis(4-hydroxyaminomethylphenoxy)benzamide

Starting compound: 3,5-bis(4-formylphenoxy)benzamide

Mass spectrometry data (m/z): 396 ([M+H]⁺)

Nuclear magnetic resonance spectrum (DMSO-d₆, TMS internal standard)

δ: 3.86(4H, s, —CH₂—N × 2),

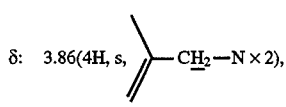

6.70–6.73(1H, m,

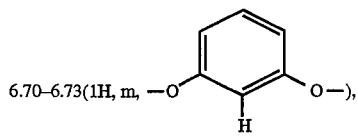

7.03(4H, d, —O— × 2),

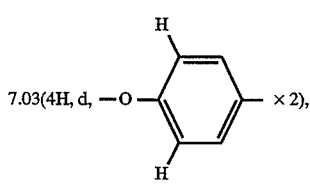

7,22(2H, d,

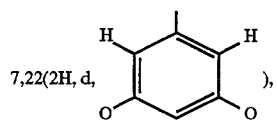

7.38(4H, d, —O— × 2)

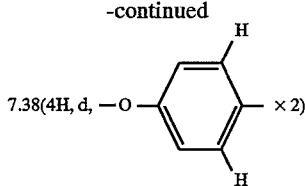

(b) The following compound was obtained in the same manner as described in Example 10 (b).

3,5-Bis[4-[(3,5-dioxo-1,2,4-oxadiazolidin-2-yl)methyl]phenoxy]benzamide

Starting compound: 3,5-bis(4-hydroxyaminomethylphenoxy)benzamide

Mass spectrometry data (m/z): 532 ([M−H]⁻)

Nuclear magnetic resonance spectrum (DMSO-d₆, TMS internal standard)

δ: 4.47(4H, s, —CH₂—N × 2),

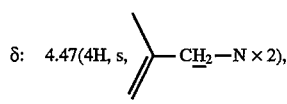

6.79(1H, t,

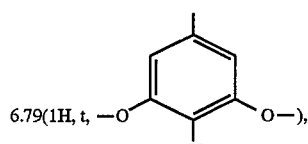

7.05(4H, d, —O— × 2),

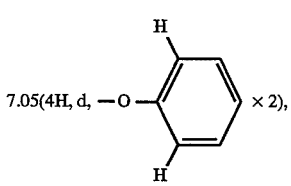

7,25(2H, d,

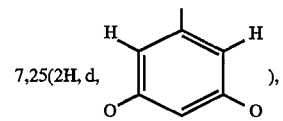

7.34(4H, d, —O— × 2)

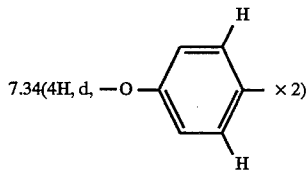

Example 48

(a) The following compound was obtained in the same manner as described in Example 10 (a).

1,3-Bis[4-(N-hydroxyaminomethyl)-2-trifluoromethylphenoxy]benzene

Starting compound: 1,3-bis(4-formyl-2-trifluoromethylphenoxy)benzene

Mass spectrometry data (m/z): 489 ([M+H]⁺)

Nuclear magnetic resonance spectrum (CDCl₃, TMS internal standard) δ: 4.02 (4H, s), 6.50 (1H, t), 6.80 (2H, d), 6.96 (2H, d), 7.31 (1H, t), 7.45 (2H, d), 7.63 (2H, d)

(b) The following compound was obtained in the same manner as described in Example 11 (b).

1,3-Bis[4-[(3,5-dioxo-1,2,4-oxadiazolidin-2-yl)methyl]-2-trifluoromethylphenoxy]benzene Starting compound: 1,3-bis[4-(N-hydroxyaminomethyl)-2-trifluoromethylphenoxy]benzene Mass spectrometry data (m/z): 625 ([M−H]⁻)

Nuclear magnetic resonance spectrum (DMSO-$d_6$, TMS internal standard) δ: 4.88 (4H, s), 6.83 (1H, t), 6.88 (2H, d), 7.18 (2H, d), 7.47 (1H, t), 7.65 (2H, d), 7.76 (2H, s), 12.50 (2H, brs)

Example 49

(a) Using a hydroxylamine compound obtained in the same manner as described in Example 10 (a), the following compound was obtained in accordance with the procedure of Example 11 (b).

1,3-Bis[2,6-difluoro-4-[(3,5-dioxo-1,2,4-oxadiazolidin-2-yl)methyl]phenoxy]benzene Starting compound: 1,3-bis(2,6-difluoro-4-formylphenoxy)benzene Melting point: >300° C. (decomposition)

Mass spectrometry data (m/z): 561 ([M−H]⁻)

Nuclear magnetic resonance spectrum (DMSO-$d_6$, TMS internal standard) δ: 4.46 (4H, s), 6.60 (2H, dd), 6.67 (1H, t), 7.23 (4H, d), 7.31 (1H, t)

Example 50

(a) The following compound was obtained in the same manner as described in Example 10 (a).

1,3-Bis[4-(N-hydroxyaminomethyl)-3-trifluoromethylphenoxy]benzene

Starting compound: 1,3-bis(4-formyl-3-trifluoromethylphenoxy)benzene

Mass spectrometry data (m/z): 489 ([M+H]⁺)

Nuclear magnetic resonance spectrum (CDCl₃, TMS internal standard) δ: 4.17 (4H, s), 6.55 (1H, d), 6.80 (2H, d), 7.14 (2H, d), 7.31–7.35 (3H, m), 7.55 (2H, d)

(b) The following compound was obtained in the same manner as described in Example 11 (b).

1,3-Bis[4-[(3,5-dioxo-1,2,4-oxadiazolidin-2-yl)methyl]-3-trifluoromethylphenoxy]benzene Starting compound: 1,3-bis[4-(N-hydroxyaminomethyl)-3-trifluoromethylphenoxy]benzene Nuclear magnetic resonance spectrum (DMSO-$d_6$, TMS internal standard) δ: 4.61 (4H, s), 6.87–6.90 (3H, m), 7.36–7.39 (4H, m), 7.46 (1H, t), 7.69 (2H, d)

Example 51

(a) The following compound was obtained in the same manner as described in Example 10 (a).

3-[4-(N-Hydroxyaminomethyl)phenoxy]-N-[4-(N-hydroxyaminomethyl)phenyl]-N-methylaniline Starting compound: 3-(4-formylphenoxy)-4-(4-formylphenyl)-N-methylaniline Mass spectrometry data (m/z): 366 ([M+H]⁺)

Nuclear magnetic resonance spectrum (CDCl₃, TMS internal standard) δ: 3.26 (3H, s), 3.95 (4H, s), 6.43 (1H, s), 6.53 (1H, d), 6.65 (1H, d), 6.95 (2H, d), 7.02 (2H, d), 7.15–7.30 (5H, m)

(b) The following compound was obtained in the same manner as described in Example 11 (b).

3-[4-[(3,5-Dioxo-1,2,4-oxadiazolidin-2-yl)methyl]phenoxy]-N-[4-(3,5-dioxo-1,2,4-oxadiazolidin-2-yl)methyl]phenyl-N-methylaniline Starting compound: 3-[4-(N-hydroxyaminomethyl)phenoxy]-N-[4-(N-hydroxyaminomethyl)phenyl]-N-methylaniline Mass spectrometry data (m/z): 502 ([M−H]⁻)

Nuclear magnetic resonance spectrum (DMSO-$d_6$, TMS internal standard) δ: 3.25 (3H, s), 4.70 (2H, s), 4.73 (2H, s), 6.51 (1H, d), 6.62 (1H, t), 6.74 (1H, d), 7.01 (2H, d), 7.09 (2H, d), 7.23–7.27 (3H, m), 7.33 (2H, d)

Example 52

(a) The following compound was obtained in the same manner as described in Example 10 (a).

1,3-Bis[4-(N-hydroxyaminomethyl)phenoxy]benzene

Starting compound: 1,3-bis(4-formylphenoxy)benzene

Melting point: 110°–114° C.

Mass spectrometry data (m/z): 353 ([M+1]⁺)

Nuclear magnetic resonance spectrum (DMSO-$d_6$, TMS internal standard) δ: 3.84 (4H, s), 5.98 (2H, s), 6.55 (1H, t, J=2.44 Hz), 6.69 (2H, dd, J=2.44 and 8.32 Hz), 6.99 (4H, d, J=8.28 Hz), 7.24 (2H, s), 7.34 (1H, d, J=8.32 Hz), 7.35 (4H, d, J=8.28 Hz)

(b) 1,3-Bis[4-(N-hydroxyaminomethyl)phenoxy]benzene (0.704 g) was dissolved in 21 ml of tetrahydrofuran to which, with ice-cooling and in an atmosphere of argon, was subsequently added dropwise 0.354 ml of chlorocarbonyl isocyanate. After 10 minutes of stirring at the same temperature, the stirring was continued for 2 hours at room temperature. The solvent was evaporated under a reduced pressure, and the resulting residue was subjected to silica gel column chromatography to obtain 0.44 g of 1,3-bis[4-[(3,5-dioxo-1,2,4-oxadiazolidin-2-yl)methyl]phenoxy]benzene from fractions of chloroform-methanol (30:1) elution.

The physicochemical properties showed that this compound is the same compound as the product of Example 55 b.

Example 53

1,3-bis[4-(N-hydroxyaminomethyl)phenoxy]benzene (1.76 g) was dissolved in 35 ml of tetrahydrofuran to which, with ice-cooling and in an atmosphere of argon, was subsequently added dropwise 1.65 g of n-butoxycarbonyl isocyanate. After 30 minutes of stirring at the same temperature, 1N sodium hydroxide aqueous solution was added dropwise thereto and the stirring was continued for 30 minutes at room temperature. After adding 1N hydrochloric acid, the solvent was evaporated, and the resulting residue was subjected to silica gel column chromatography to obtain 1.0 g of 1,3-bis[4-[(3,5-dioxo-1,2,4-oxadiazolidin-2-yl)methyl]phenoxy]benzene from fractions of chloroform-methanol (30:1) elution.

The physicochemical properties showed that this compound is the same compound as the product of Example 55 b.

Example 54

Phenol (3.76 g) was dissolved in 15 ml of tetrahydrofuran and 1.24 g of ethoxycarbonyl isocyanate was added dropwise in an atmosphere of argon at room temperature. After 3 hours of stirring at the same temperature, 1.41 g of 1,3-bis[4-(N-hydroxyaminomethyl)phenoxy]benzene was added and the stirring was continued for 1 hour. After addition of 3 drops of triethylamine and subsequent 16 hours of stirring at 60° C., 1N sodium hydroxide aqueous solution was added dropwise to the reaction mixture with ice-cooling, followed by 1 hour of stirring at room temperature. This was mixed with 1N hydrochloric acid, the solvent was evaporated and then water was added to the resulting residue to obtain 0.8 g of crude crystals. They were further washed with diethyl ether and ethanol to obtain 0.4 g of 1,3-bis[4-[(3,5-dioxo-1,2,4-oxadiazolidin-2-yl)methyl]phenoxy]benzene.

The physicochemical properties showed that this compound is the same compound with the product of Example 55 b.

Example 55

(a) 1,3-Bis[4-(hydroxyaminomethyl)phenoxy]benzene (1.06 g) was dissolved in 10 ml of tetrahydrofuran to which, with ice-cooling and in an atmosphere of argon, was subsequently added dropwise 0.68 ml of ethoxycarbonyl isocyanate. After 2 hours and 30 minutes of stirring at the room temperature, the thus formed crystals were collected by filtration and washed with diethyl ether and ethanol to obtain 1.09 g of 1,3-bis[4-[1-(3-ethoxycarbonyl-1-hydroxyurenylene)methyl]phenoxy]benzene.

Melting point: 145°–148° C.

Mass spectrometry data (m/z): 583 ([M+H]$^+$)

Nuclear magnetic resonance spectrum (DMSO-d$_6$, TMS internal standard)

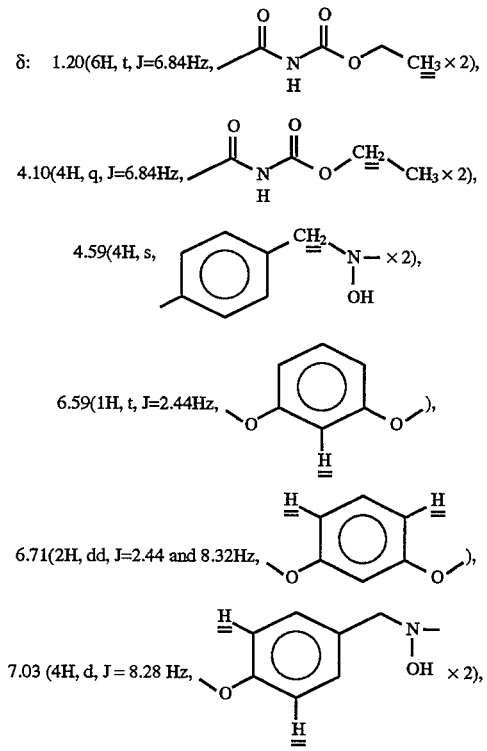

(b) 1,3-Bis[4-[1-(3-ethoxycarbonyl-1-hydroxyurenylene)methyl]phenoxy]benzene (0.85 g) was dispersed in 8.5 ml of tetrahydrofuran to which, with ice-cooling, was subsequently added dropwise 1N sodium hydroxide aqueous solution, followed by 30 minutes of stirring at room temperature. After adding 1N hydrochloric acid, the solvent was evaporated under a reduced pressure, and water was added to the resulting residue. The thus formed crystals were collected by filtration and recrystallized from acetic acid to obtain 0.35 g of 1,3-bis[4-[(3,5-dioxo-1,2,4-oxadiazolidin-2-yl)methyl]phenoxy]benzene.

Melting point: 182°–184° C.

Elemental analysis (for $C_{24}H_{18}N_4O_8$)

|  | C (%) | H (%) | N (%) |
|---|---|---|---|
| calcd. | 58.78 | 3.70 | 11.42 |
| found | 58.77 | 3.83 | 11.37 |

Mass spectrometry data (m/z): 489 ([M−H]$^-$)

Nuclear magnetic resonance spectrum (DMSO-d$_6$, TMS internal standard)

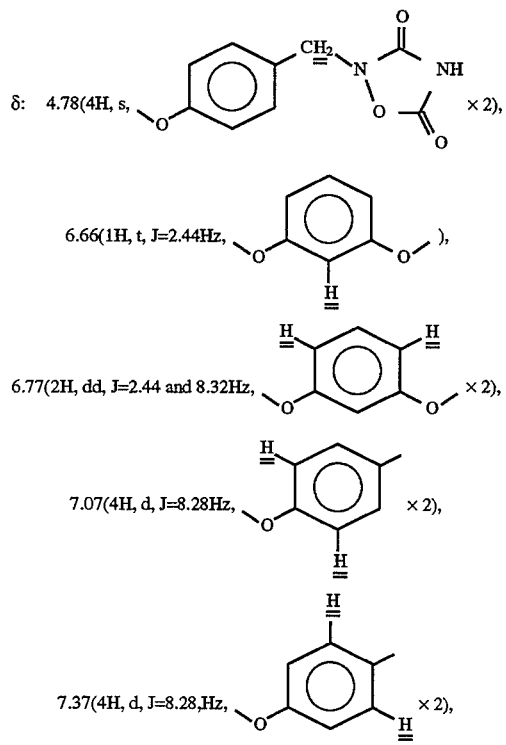

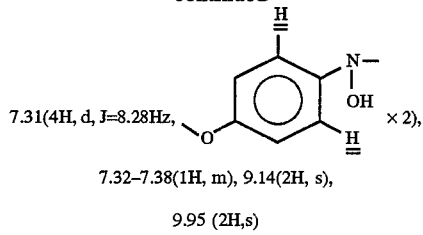

-continued

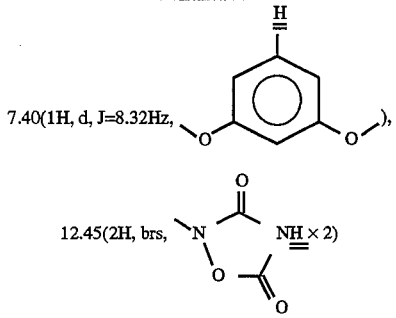

7.40(1H, d, J=8.32Hz), 12.45(2H, brs,

Example 56

(a) The following compound was obtained in the same manner as described in Reference Example 22 (b).

Bis(4-formylphenyl)methylamine

Mass spectrometry data (m/z): 240 ([M+H]$^+$)

Nuclear magnetic resonance spectrum (CDCl$_3$, TMS internal standard) δ: 3.49 (3H, s), 7.19 (4H, d), 7.83 (4H, d), 9.90 (2H, s)

(b) The following compound was obtained in the same manner as described in Example 10 (a).

Bis(4-hydroxyaminomethylphenyl)methylamine

Nuclear magnetic resonance spectrum (CDCl$_3$, TMS internal standard) δ: 3.26 (3H, s), 3.92 (4H, s), 5.40 (2H, brs), 6.94 (4H, d), 7.20 (4H, d)

(c) The following compound was obtained in the same manner as described in Reference Example 11 (b).

Bis[4-[(3,5-dioxo-1,2,4-oxadiazolidin-2-yl)methyl] phenyl]methylamine

Mass spectrometry data (m/z): 410 ([M−H]$^−$)

Nuclear magnetic resonance spectrum (DMSO-d$_6$, TMS internal standard) δ: 3.27 (3H, s), 4.72 (4H, s), 7.02 (4H, d), 7.25 (4H, d), 12.42 (2H, brs)

Elemental analysis (for C$_{19}$H$_{17}$N$_5$O$_6$)

|  | C (%) | H (%) | N (%) |
|---|---|---|---|
| calcd. | 55.47 | 4.17 | 17.02 |
| found | 55.20 | 4.08 | 16.85 |

Example 57

(a) The following compound was obtained in the same manner as described in Reference Example 22 (b).

Bis(4-formylphenyl) sulfide

Mass spectrometry data (m/z): 243 ([M+H]$^+$)

Nuclear magnetic resonance spectrum (CDCl$_3$, TMS internal standard) δ: 7.48 (4H, d), 7.85 (4H, d), 10.00 (2H, s)

(b) The following compound was obtained in the same manner as described in Example 10 (a).

Bis(4-hydroxyaminomethylphenyl) sulfide

Nuclear magnetic resonance spectrum (DMSO-d$_6$, TMS internal standard) δ: 3.84 (4H, s), 6.01 (2H, s), 7.20–7.40 (8H, m)

(c) The following compound was obtained in the same manner as described in Reference Example 11 (b).

Bis[4-[(3,5-dioxo-1,2,4-oxadiazolidin-2-yl)methyl] phenyl]sulfide

Mass spectrometry data (m/z): 413 ([M−H]$^−$)

Nuclear magnetic resonance spectrum (DMSO-d$_6$, TMS internal standard) δ: 4.79 (4H, s), 7.36 (8H, s), 12.46 (2H, brs)

Elemental analysis (for C$_{18}$H$_{14}$N$_4$O$_6$S)

|  | C (%) | H (%) | N (%) | S (%) |
|---|---|---|---|---|
| calcd. | 52.17 | 3.41 | 13.52 | 7.74 |
| found | 52.17 | 3.47 | 13.22 | 7.73 |

Example 58

At room temperature, 1.76 g of metachloroperbenzoic acid was added to a mixture of 910 mg of bis[4-[(3,5-dioxo-1,2,4-oxadiazolidin-2-yl)methyl]phenyl]thioether and 5 ml of dichloromethane and the mixture was stirred for 15 hours. The thus formed crystals were collected by filtration, washed with dichloromethane and then dried to obtain 730 mg of bis[4-[(3,5-dioxo-1,2,4-oxadiazolidin-2-yl)methyl] phenyl]sulfone.

Mass spectrometry data (m/z): 445 ([M−H]$^−$)

Nuclear magnetic resonance spectrum (DMSO-d$_6$, TMS internal standard) δ: 4.90 (4H, s), 7.60 (4H, d), 8.00 (4H, d), 12.50 (2H, brs)

Structures of the compounds obtained in Examples are shown in Table 2.

TABLE 2

[Structure: HN-C(=O)-C(=O)-N(-O-)(cyclic isoxazolidinedione)-CH₂-(B₁)-L-(B₂)-CH₂-N(similar ring)]

| Ex. No. | B₁ | L | B₂ |
|---|---|---|---|
| 1 | 1,4-phenylene | —O— | 1,4-phenylene |
| 2 | " | —CH₂— | " |
| 3 | " | 2,7-naphthylene | " |
| 4 | " | —O—(1,4-C₆H₄)—O— | " |
| 5 | " | —O—(CH₂)₅—O— | " |
| 6 | " | —O—(1,3-C₆H₄)—O— | " |
| 7 | " | —OCH₂—(trans-1,4-cyclohexylene)—CH₂O— | " |
| 8 | " | —O—(cis-1,3-cyclohexylene)—O— | " |
| 9 | 1,4-phenylene | —O—(1,2-C₆H₄)—O— | 1,4-phenylene |
| 10 | " | —OCH₂—CH=CH—CH₂O— (cis) | " |
| 11 | " | —O—(CH₂)₉—O— | " |
| 12 | " | —O—(CH₂)₄—O— | " |
| 13 | " | —O—(CH₂)₆—O— | " |
| 14 | " | —OCH₂—CH=CH—CH₂O— (trans) | " |
| 15 | " | —O—(CH₂)₇—O— | " |
| 16 | " | —OCH₂—(1,3-C₆H₄)—CH₂O— | " |

TABLE 2-continued
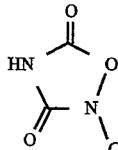
| Ex. No. | B₁ | L | B₂ |
|---|---|---|---|
| 17 | " | −O−CH₂CH₂C(CH₃)(CH₃)CH₂CH₂−O− | " |
| 18 | " | 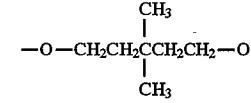 | " |
| 19 | 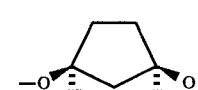 | 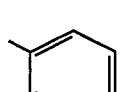 | 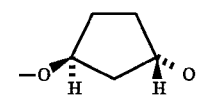 |
| 20 | " | −O−(CH₂)₈−O− | " |
| 21 | " | −O−(CH₂)₂−O−(CH₂)₂−O− | " |
| 22 | " | −O−(CH₂)₂−O− | " |
| 23 | " | −O−(CH₂)₃−O− | " |
| 24 | " | −O−(CH₂)₁₀−O− | " |
| 25 | " | −O−(CH₂)₁₁−O− | " |
| 26 | " | −O−(CH₂)₁₂−O− | " |
| 27 | " | −OCH₂C(F)(F)−C(F)(F)−C(F)(F)−CH₂O− | " |
| 28 | " | 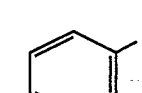 | " |
| 29 | 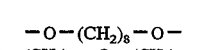 | −NHCO−C₆H₄−CONH− | 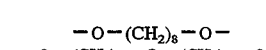 |
| 30 | " | −CO−C₆H₄−CO− | " |
| 31 | " |  | " |
| 32 | " | 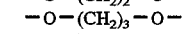 | " |
| 33 | " | 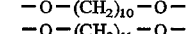 | " |

TABLE 2-continued
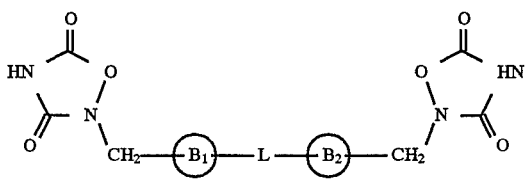
| Ex. No. | B₁ | L | B₂ |
|---|---|---|---|
| 34 | " | 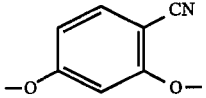 | " |
| 35 | " | 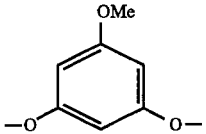 | " |
| 36 | " | 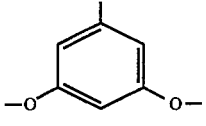 | " |
| 37 | " | 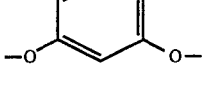 | " |
| 38 | " | 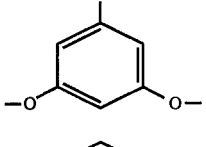 | " |
| 39 | 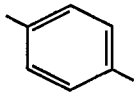 | 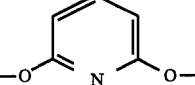 | 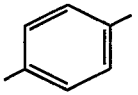 |
| 40 | " | 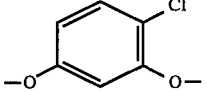 | " |
| 41 |  | 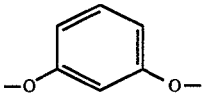 | 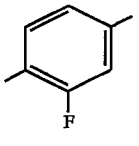 |
| 42 | 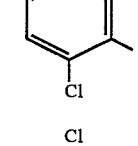 | " | 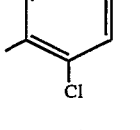 |
| 43 | 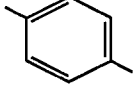 | " | 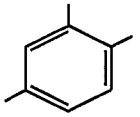 |

TABLE 2-continued

| Ex. No. | B₁ | L | B₂ |
|---|---|---|---|
| 44 | 1,4-phenylene | 5-methyl-1,3-phenylene bis(oxy) (–O–C₆H₃(Me)–O–) | 1,4-phenylene |
| 45 | " | 4,6-dichloro-1,3-phenylene bis(oxy) | " |
| 46 | " | 4-ethyl-1,3-phenylene bis(oxy) | " |
| 47 | " | 5-carbamoyl-1,3-phenylene bis(oxy) (–O–C₆H₃(CONH₂)–O–) | " |
| 48 | 2-trifluoromethyl-1,4-phenylene | 1,3-phenylene bis(oxy) (–O–C₆H₄–O–) | 2-trifluoromethyl-1,4-phenylene |
| 49 | 2,6-difluoro-1,4-phenylene | " | 2,6-difluoro-1,4-phenylene |
| 50 | 2-trifluoromethyl-1,4-phenylene | " | 2-trifluoromethyl-1,4-phenylene |
| 51 | 1,4-phenylene | 3-(N-methylamino)-phenyl ether linkage (–O–C₆H₄–N(Me)–) | 1,4-phenylene |
| 52 | " | 1,3-phenylene bis(oxy) | " |
| 53 | " | " | " |
| 54 | " | " | " |
| 55 | " | " | " |
| 56 | " | –N(Me)– | " |

TABLE 2-continued

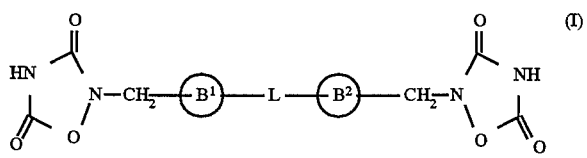

| Ex. No. | B₁ | L | B₂ |
|---|---|---|---|
| 57 | " | —S— | " |
| 58 | " | —SO₂— | " |

We claim:

1. A bisoxadiazolidine dione derivative represented by the following general formula (I)

$$\text{HN} \underset{O}{\overset{O}{\diagdown}} \text{N—CH}_2\text{—(B}^1\text{)—L—(B}^2\text{)—CH}_2\text{—N} \underset{O}{\overset{O}{\diagdown}} \text{NH} \quad (I)$$

symbols in the formula represent the following meanings;

—(B¹)— or —(B²)—:

the same or different from each other and each represents a phenylene group which may be substituted,

L:

(1) an oxygen atom, (2) a group represented by the formula $$\underset{|}{\overset{R^1}{\underset{}{\phantom{x}}}}\\ -N-,$$

(3) a group represented by the formula —S(O)$_n$—, (4) a group represented by the formula —CO—, (5) a group represented by the formula $$\underset{|}{\overset{R^2}{\phantom{x}}} \quad \underset{|}{\overset{R^2}{\phantom{x}}}\\ -\text{CON}- \text{ or } -\text{NCO}-,$$

(6) an alkylene group or an alkenylene group which may respectively be interrupted with an oxygen atom and/or a sulfur atom and which may each be substituted, or (7) a group represented by a formula

—L¹—(A)—L²—,

R¹: a hydrogen atom or a lower alkyl group, n: 0, 1 or 2,

R²: a hydrogen atom or a lower alkyl group,

L¹ and L²: the same or different from each other and each represents (1) an oxygen atom, (2) a group represented by the formula $$\underset{|}{\overset{R^1}{\phantom{x}}}\\ -N-,$$

R¹ is as defined in the foregoing, (3) a group represented by the formula —S(O)$_n$—, n is as defined in the foregoing, (4) a group represented by the formula —CO—, (5) a group represented by the formula $$\underset{|}{\overset{R^2}{\phantom{x}}} \quad \underset{|}{\overset{R^2}{\phantom{x}}}\\ -\text{CON}- \text{ or } -\text{NCO}-,$$

R² is as defined in the foregoing, or (6) an alkylene group or an alkenylene group which may respectively be interrupted with an oxygen atom and/or a sulfur atom and which may each be substituted, and

—(A)—:

a cycloalkanediyl group, an arylene group or a pyridinediyl group, which may respectively be substituted, or a pharmaceutically acceptable salt thereof.

2. The compound according to claim 1, wherein substituents on

—(B¹)—, —(B²)— and —(A)—, when present, are one or more substituents selected from the group consisting of a halogen atom, a lower alkyl group, a halo-lower alkyl group, a lower alkoxy group, a cyano group, a nitro group, an amino group, a lower alkyl-substituted amino group, a carbamoyl group and a lower alkyl-substituted carbamoyl group, and the substituent on L, L¹ and L², when present, is a halogen atom.

3. The compound according to claim 2, wherein

—(B¹)— and —(B²)— may be the same or different from each other and each represents a phenylene group which may be substituted with one or more substituents selected from the group consisting of a halogen atom, a lower alkyl group and a halo-lower alkyl group, and L is (1) an alkylene group or an alkenylene group which may respectively be interrupted with an oxygen atom and/or a sulfur atom and which may each be substituted with one or more halogen atoms, or (2) a group represented by

wherein $L^1$ and $L^2$ may be the same or different from each other and each represents an alkylene group or an alkenylene group which may respectively be interrupted with an oxygen atom and/or a sulfur atom and may each be substituted with one or more halogen atoms and

is a cycloalkanediyl group, an arylene group or a pyridinediyl group which may each be substituted with one or more substituents selected from the group consisting of a halogen atom, a lower alkyl group, a halo-lower alkyl group, a lower alkoxy group, a cyano group, a nitro group, an amino group, a lower alkyl-substituted amino group, a carbamoyl group and a lower alkyl-substituted carbamoyl group.

4. 1,3-Bis[4-[(3,5-dioxo-1,2,4-oxadiazolidin-2-yl)methyl]phenoxy]benzene or a pharmaceutically acceptable salt thereof.

5. 1,4-Bis[4-[(3,5-dioxo-1,2,4-oxadiazolidin-2-yl)methyl]phenoxy]-2-butene or a pharmaceutically acceptable salt thereof.

6. 1,9-Bis[4-[(3,5-dioxo-1,2,4-oxadiazolidin-2-yl)methyl]phenoxy]nonane or a pharmaceutically acceptable salt thereof.

7. A pharmaceutical composition which comprises a bisoxadiazolidine dione derivative represented by the following general formula (I) or a pharmaceutically acceptable salt thereof and a pharmaceutically acceptable carrier

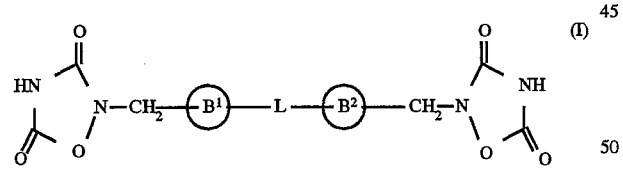

symbols in the formula represent the following meanings;

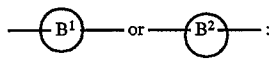

the same or different from each other and each represents a phenylene group which may be substituted,

L:

(1) an oxygen atom, (2) a group represented by the formula

(3) a group represented by the formula $-S(O)_n-$,
(4) a group represented by the formula $-CO-$,
(5) a group represented by the formula

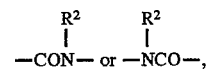

(6) an alkylene group or an alkenylene group which may respectively be interrupted with an oxygen atom and/or a sulfur atom and which may each be substituted, or
(7) a group represented by a formula

$R^1$: a hydrogen atom or a lower alkyl group,
n: 0, 1 or 2,
$R^2$: a hydrogen atom or a lower alkyl group,
$L^1$ and $L^2$: the same or different from each other and each represents
(1) an oxygen atom,
(2) a group represented by the formula

$R^1$ is as defined in the foregoing,
(3) a group represented by the formula $-S(O)_n-$, n is as defined in the foregoing,
(4) a group represented by the formula $-CO-$,
(5) a group represented by the formula

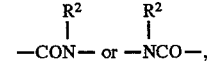

$R^2$ is as defined in the foregoing), or
(6) an alkylene group or an alkenylene group which may respectively be interrupted with an oxygen atom and/or a sulfur atom and which may each be substituted, and

a cycloalkanediyl group, an arylene group or a pyridinediyl group, which may respectively be substituted.

8. The pharmaceutical composition according to claim 7, having insulin sensitivity-increasing activity.

9. The pharmaceutical composition according to claim 7, having hypoglycemic activity.

10. The pharmaceutical composition according to claim 7, useful in the treatment of diabetes mellitus and/or the prevention and/or treatment of diabetic complications.

* * * * *